(12) United States Patent
Skerra et al.

(10) Patent No.: US 8,598,317 B2
(45) Date of Patent: Dec. 3, 2013

(54) MUTEINS OF TEAR LIPOCALIN WITH AFFINITY FOR THE T-CELL CORECEPTOR CD4

(75) Inventors: Arne Skerra, Freising (DE); Amber Nasreen, München (DE)

(73) Assignee: Technische Universitaet Muenchen, Munich (DE)

( * ) Notice: Subject to any disclaimer, the term of this patent is extended or adjusted under 35 U.S.C. 154(b) by 742 days.

(21) Appl. No.: 12/293,715

(22) PCT Filed: Mar. 20, 2007

(86) PCT No.: PCT/EP2007/052635
§ 371 (c)(1),
(2), (4) Date: Sep. 22, 2008

(87) PCT Pub. No.: WO2007/107563
PCT Pub. Date: Sep. 27, 2007

(65) Prior Publication Data
US 2010/0160612 A1   Jun. 24, 2010

Related U.S. Application Data

(60) Provisional application No. 60/783,991, filed on Mar. 20, 2006.

(51) Int. Cl.
*C07K 14/00* (2006.01)
*C12N 15/74* (2006.01)

(52) U.S. Cl.
USPC .......................................... 530/350; 435/471

(58) Field of Classification Search
None
See application file for complete search history.

(56) References Cited

U.S. PATENT DOCUMENTS 7,250,297 B1   7/2007   Beste et al.

FOREIGN PATENT DOCUMENTS

| WO | WO 99/16873 A1 | 4/1999 |
| WO | WO 2005/019256 A2 | 3/2005 |
| WO | WO 2006/056464 A2 | 6/2006 |

OTHER PUBLICATIONS

Airaksinen et al., Nucleic Acids Res 26:576-581, 1998.*
Folz et al., J. Biol. Chem. 263:2070-2078, 1988.*
International Search Report mailed on Oct. 30, 2007, in corresponding PCT/EP2007/052635, 5 pages.
International Preliminary Report on Patentability mailed on Sep. 23, 2008, in corresponding PCT/EP2007/052635, 7 pages.
Gasymov et al., "RET and Anisotropy Measurements Establish the Proximity of the Conserved Trp17 to Ile98 and Phe99 of Tear Lipocalin," Biochemistry, 2002, 41(28):8837-8848.
Shattock et al., "Inhibiting Sexual Transmission of HIV-1 Infection," Nat. Rev. Microbiol., 2003, 1(1):25-34.
Berg et al., "Immunology Provides Important Techniques with Which to Investigate Proteins," Biochemistry, 6$^{th}$ Edition, 2007, 84-85.
Beste et al., "Small antibody-like proteins with prescribed ligand specificities derived from the lipocalin fold," Proc. Natl. Acad. Sci. USA, Mar. 1999, 96:1898-1903.
Skerra, Arne, "Engineered protein scaffolds for molecular recognition," Journal of Molecular Recognition, 2000, 13:167-187.
Skerra, Arne, "Lipocalins as a scaffold," Biochimica et Biophysica Acta, 2000, 1482:337-350.

* cited by examiner

*Primary Examiner* — Suzanne M Noakes
(74) *Attorney, Agent, or Firm* — Foley & Lardner LLP

(57) ABSTRACT

The present invention relates to a mutein of human tear lipocalin, wherein the mutein comprises at least one mutated amino acid residue at any two or more of the sequence positions 24-36, 53-66, 79-84, and 102-110 (or 103-110) of the linear polypeptide sequence of the mature human tear lipocalin, and wherein the mutein binds to the extracellular region of the T-cell coreceptor CD4 with detectable affinity. The invention also relates to a method of generating such a mutein as well as to various pharmaceutical uses of such a mutein.

24 Claims, 19 Drawing Sheets

```
                    SerTyrLys                                                     Arg Gln Ala
            ........GTGCTGAAG..TC............................T..................AAC CAC ...........T...
M48                 ValLeuLys                                                     Asn His           Phe
            ........GCATTGTTC..TC............................T..................CAC TCC.......C......
M154                AlaLeuPhe                                                     His Ser           His
            ........TTGTGCGGG..TC...............................................CTC GAC..............
M23                 LeuCysGly                                                     Leu Asp
            ........TTGTCCGGG..TC...............................................CTC GAC..............
M23*                LeuSerGly                                                     Leu Asp
            ........TTGTCCGGG..TC...............................................CTC GAC..............
M23.11A             LeuSerGly                                                     Leu Asp
            ........TTGTCCGGG..TC.........................C.....................CTC GAC..............
M23.31B             LeuSerGly                                                     Leu Asp
                                                                                  Asn

457 AGGTCGCACGTGAAGGACCACTACATCTTTTACTCTGAGGGCGAGCTCCACGGGAAGCCGGTCCCAGGGGTGTGCCTCGTGGGCAGAGACCCCAAGAACAACCTGGAA 565
                ArgSerHisValLysAspHisTyrIlePheTyrSerGluGlyGluLeuHisGlyLysProValProGlyValTrpLeuValGlyArgAspProThrAsnAsnLeuGlu
                                                102        NNSNNSNNS   NNS   111  114

M25         .........................................................................TCGTGGCTG..TTC
                                                                                   SerTrpLeu  Phe
M32         .........................................................................TACTGGATC..TTA
                                                                                   TyrTrpIle  Leu
M31         .........................................................................A..TCGTTGCTG..GTG
                                                                                   Lys  SerLeuLeu  Val
M18         .........................................................................A..TGGTTGAGG..TTG
                                                                                   Lys  TrpLeuArg  Leu
M18*        .........................................................................A..TGGTTGAGG..TTG
                                                                                   Lys  TrpLeuArg  Leu
M48         .........................................................................GCGGTGCTG..TGG
                                                                                        AlaValLeu  Trp
M154        .........................................................................TGGTTCCGC..TTC
                                                                                        TrpPheArg  Phe
M23         .........................................................................A..TGGTTGGGG..TTC
                                                                                   Lys  TrpLeuGly  Phe
M23*        .........................................................................A..TGGTTGGGG..TTC
                                                                                   Lys  TrpLeuGly  Phe
M23.11A     ....G....................................................................A..TGGTTGGGG..TTC
                Gly                                                                Lys  TrpLeuGly  Phe
M23.31B     ....G....................................................................G..TGGTTGGGG..TTC
                                                                                   Glu  TrpLeuGly  Phe
```

MUTEINS OF TEAR LIPOCALIN WITH AFFINITY FOR THE T-CELL CORECEPTOR CD4

CROSS-REFERENCE TO RELATED APPLICATIONS

The present application is a National Stage application of PCT/EP2007/052635, filed Mar. 20, 2007, which claims the priority of U.S. provisional application 60/783,991, filed Mar. 20, 2006, the entire contents of which are incorporated herein in their entirety for all purposes.

SEQUENCE LISTING

The instant application contains a Sequence Listing which has been submitted in ANSI format via EFS-Web and is hereby incorporated by reference in its entirety. Said ANSI copy, created on Jun. 3, 2011, is named newseq.txt and is 63 KB in size.

FIELD OF THE INVENTION

The present invention relates to a mutein of human tear lipocalin that binds the T-cell coreceptor CD4 with detectable affinity. In some embodiments of the invention the mutein blocks the interaction between CD4 and the glycoprotein gp120 of the human immunodeficiency virus (HIV), so that the mutein of tear lipocalin can be used for the prevention and/or treatment of infection with human immunodeficiency virus. The invention also relates to a pharmaceutical composition comprising such a mutein as well as to various pharmaceutical uses of such a mutein, for example, for the prevention and/or treatment of cancer, of an auto-immune disease or of an infectious disease.

BACKGROUND OF THE INVENTION

The human T-cell co-receptor CD4 (Swiss-Prot data bank entry P01730) is the primary target for infection of lymphocytes with the human immunodeficieny viruses HIV-1 and HIV-2. Complex formation between CD4 and the viral envelope glycoprotein gp120 is the primary step which initates the subsequent membrane fusion process (Green, W et al. (2004) The brightening future of HIV therapeutics. Nat Immunol 5, 867-871). The first amino-terminal domain (named Ig-like V-type domain or D1) of altogether four extracellular domains of CD4 plays a predominant role in this process (Kwong, P. D., Wyatt, R., Robinson, J., Sweet, R. W., Sodroski, J. and Hendrickson, W. A. (1998). Structure of an HIV gp120 envelope glycoprotein in complex with the CD4 receptor and a neutralizing human antibody. Nature 393, 648-659).

Accordingly, inhibitors of this interaction have the potential to prevent or impair the infection with HIV or to prevent and/or treat AIDS (acquired immunodeficiency syndrome). For this reason, antibodies directed against CD4 and having antagonistic properties with respect to the binding of gp120 are presently of high clinical interest. One such antibodies, TNX-355, is currently subject to a phase II clinical trial carried out by Tanox Inc (Reeves, J. D. & Piefer, A. J., Emerging Drug targets for antiretroviral therapy, Drugs, 2005). TNX-355 is a humanized monoclonal antibody that binds to the second extracellular domain of CD4 (called Ig-like C2-type 1 or D2). Entry of HIV into lymphocytes is apparently prevented by inhibiting membrane fusion via a conformational mechanism after association of the CD4 molecule with gp120. According to the product information of Tanox Inc, the antibody was well tolerated in clinical phase I and II trials and showed transient but meaningful loads in HIV-1 infected patients without seeming to impair the normal immune function.

Apart from systemic administration, for example by intravenous injection, such antagonists of the CD4/gp120 interaction should also inhibit the primary event of infection, in particular for migrating CD4 positive immune cells during sexual transmission when topically applied to the vaginal mucosa. Such antagonists are therefore also referred to as "Viral Entry Inhibitors" (see Shattock, R. J. and Moore, J. P. (2003). Inhibiting sexual transmission of HIV-1 infection. Nat Rev Microbiol 1, 25-34).

However, antibodies such as TNX-355 may not be suitable for all potential applications. One limiting factor may be their rather large molecular size, which is even the case for their antigen-binding fragments such as Fab fragments. In addition, there is a large effort associated with the biotechnological production of intact antibodies, thus causing high cost of goods.

Accordingly, it would be desirable to obtain alternatives to antibodies that are able to bind the extracellular region of CD4 and to inhibit the interaction with gp120 of HIV, which can be used in pharmaceutical applications as described above. Hence, it is an objective of the present invention to provide such compounds.

SUMMARY OF THE INVENTION

In one aspect of the present invention, such a compound is a mutein of human tear lipocalin. This mutein comprises at least one mutated amino acid residue at any two or more of the sequence positions 24-36, 53-66, 79-84, and 102-110 of the linear polypeptide sequence of the mature human tear lipocalin, and the mutein binds to the extracellular region of the T-cell coreceptor CD4 with detectable affinity. In another aspect of the invention such a mutein that binds to the extracellular region of the CD4 coreceptor comprises at least one mutated amino acid residue at any two or more of the sequence positions 24-36, 53-66, 79-84, and 103-110 of the linear polypeptide sequence of the mature human tear lipocalin.

In some embodiments, the tear lipocalin mutein of the invention blocks the interaction between CD4 and gp120 of HIV in such a manner that the mutein has antagonistic properties. Typically, a tear lipocalin mutein of the present invention inhibits the interaction between the viral gp120 and the extracellular domains of CD4. By doing so, a tear lipocalin mutein of the invention is able to prevent attachment and entry of HIV into CD4 positive T-cells (i.e., T-cells that carry the CD4 receptor on their surface). For this purpose, the tear mutein of the invention can, in principle, bind to any of the four immunoglobulin-like extracellular domains of CD4. These four domains are collectively designated as extracellular region of CD4. By D1 domain (also called Ig-like V-type) is meant herein the segment that is formed by sequence positions 1 to 100 of the amino acid sequence of the mature CD4, i.e. the protein after cleavage of the signal peptide (Swiss-Prot entry P01730). By D2 domain (also called Ig-like C2-type 1) is meant herein the segment that is formed by sequence positions 101 to 178 of the amino acid sequence of CD4. By D3 domain (also called Ig-like C2-type 2) is meant herein the segment that is formed by sequence positions 179 to 292 of the amino acid sequence of CD4 and by D4 domain (also called Ig-like C2-type 3) is meant herein the segment that is formed by sequence positions 293 to 349 of the amino acid sequence of CD4.

In some embodiments, the mutein lipocalin muteins binds to either the D1 or the D2 domain of CD4 or to an "epitope" that is fomed together by the D1 and D2 domains. In other embodiments a mutein of the invention can also bind to the D3 or D4 domain or to a segment that is formed by two or more of any of the four extracellular CD4 domains. Accordingly, the present invention encompasses all tear lipocalin muteins that are able to inhibit the interaction of CD4 with gp 120 of HIV, irrespective of the segment of the extracellular region that is bound by the mutein. The segment to which the mutein binds can be deliberately chosen by presenting a predetermined part of the amino acid sequence of the extracellular region of CD4 to the expression product of a naïve nucleic acid library that encodes for a plurality of tear lipocalin muteins and by selecting cognate muteins from muteins without binding activity via physical separation. In illustrative embodiments, the segment of CD4 that is employed to select tear lipocalin muteins that are to bind CD4 can comprise the sequence positions 1 to 100 (comprising the complete D1 domain), sequence positions 1 to 100 (comprising the complete D2 domain) or sequences positions 101 to 178 (comprising the complete D1 and D2 domain) of the amino acid sequence of the mature CD4. It is of course possible to use a larger fragment, for example a fragment that includes sequence positions 1 to 184 of the mature CD4 (see Example 1). It is of course also possible to use shorter fragments that comprise only a part of the respective domain such as the D1 or D2 domain, for example, fragments that include only sequence positions 10 to 95 or sequence positions 110 to 175 of the mature CD4. Likewise, and in accordance with the above disclosure, it is further possible to use a fragment that comprises part of the D1 and part of the D2 domain, for example, sequence positions 20 to 165 of the mature CD4, for selecting tear lipocalin muteins with affinity to CD4.

In case a tear mutein of the invention is to be used for the prevention or treatment of a HIV infection (by inhibiting the interaction between the viral gp120 of HIV and the extracellular domains of CD4) the virus can belong to either of the two HIV types, HIV-1 or HIV-2. Within the HIV-1 lineage, the virus may belong to any of subgroups such as HIV subgroup A, B, C, D, E, F, G, H or O. Within the HIV-2 lineage, the virus may belong to the subgroup A or B. For a classification of HIV see Rambaut, A et al. (2004) The causes and consequences of HIV evolution Nature Reviews Genetic, January, Vol. 5, 52-60.

It is however to be noted in this context that in addition to tear lipocalin muteins that are able to block the interaction between CD4 and gp120 of HIV, the invention also encompasses tear lipocalin muteins that bind CD4 alone without inhibiting the CD4-120 interaction. Similarly as antagonistic CD4 binding muteins, such "non antagonistic" CD4 binding muteins can be used as attractive alternative to antibodies (for example the human monoclonal antibody HuMax-CD4 of GenMab A/S) for tumor therapy (for example, treatment of cutaneous or non-cutaneous T-cell lymphoma) or for treating autoimmune diseases and inflammatory diseases, including rheumatoid arthritis and psoriasis (cf. in this regard: www.genmab.com/html/2002_09_19.shtml or www.genmab.com/products_dev.asp).

In accordance with the above, the invention further relates to a method for the generation of a mutein of human tear lipocalin binding the extracellular region of CD4 with detectable affinity, comprising:

(a) subjecting a nucleic acid molecule encoding human tear lipocalin, to mutagenesis at least one codon of any of the sequence positions 24-36, 53-66, 79-84, and 102-110 (or 103-110) of the linear polypeptide sequence of human tear lipocalin, thereby obtaining a plurality of nucleic acids encoding muteins of human tear lipocalin, (b) expressing the plurality of nucleic acid molecule obtained in (a) in a suitable expression system, thereby generating a plurality of muteins of human tear lipocalin, (c) bringing the plurarity of muteins of human tear lipocalin into contact with at least a fragment of the extracellular region of the T-cell receptor CD4, and (d) enriching at least one mutein having a detectable binding affinity for the at least one fragment of the extracellular region of CD4 by means of selection and/or isolation.

In particular embodiments of this method, a nucleic acid molecule encoding human tear lipocalin mutein is subjected to (random) mutagenesis at at least 2, 5, 8, 10, 12, 14 or 16 codons of the sequence positions 24-36, 53-66, 79-84, and 102-110 (or 103 to 110) of the linear polypeptide sequence of human tear lipocalin. It is also possible to subject the nucleic acid molecule that encodes human tear lipocalin mutein to mutagenesis at at least 2, 5, 8, 10, 12, 14, 15, 16, 17, 18, 20 or 22 of the codons of sequence positions 26, 27, 28, 29, 30, 31, 32, 33, 34, 56, 57, 58, 60, 61, 62, 64, 80, 83, 102, 104, 105, 106, 107 and 108 of the mature amino acid sequence of human tear lipocalin.

BRIEF DESCRIPTION OF THE DRAWINGS

The invention is further illustrated by the following non-limiting examples and the attached drawings in which:

FIG. 1 shows the crystal structure of the T-cell co-receptor CD4;

FIG. 2 schematically shows the relevant part of the expression vectors pCD4-1 and pCD4-3 that were used for bacterial production of the two N-terminal domains of hCD4, comprising amino acid residues 1 to 184, carrying either the STREP-TAG® II (a system providing a method which allows the purification and detection of proteins by affinity chromatography) (CD4-D12-strepII) or the $His_6$-tag (CD4-D12-his6), respectively. FIG. 2 also shows the vectors for Tlc-based mutein selection and expression. pTlc26 was used for bacterial production of tear lipocalin muteins of the invention, pTlc27 was used for the construction of a phagemid library encoding human tear lipocalin muteins, and pTlc28 was used for the filer sandwich colony screening assay.

FIG. 3 depicts the result of an ELISA assay that was performed for functional analysis of the recombinant CD4 (CD4-D12-strep II);

FIG. 4 shows the three-dimensional structure of human tear lipocalin, wherein the peptide segments formed by the sequence positions 26-34, 56-58, 80 and 83, and 104-106 and 108 of the linear polypeptide sequence of the mature protein that are subjected to mutagensis are labeled #1, #2, #3, and #4;

FIG. 5 shows the three-dimensional structure of human tear lipocalin, with the 18 sequence positions that are selected in one embodiment for mutagenesis in the segments formed by the sequence positions 26-34, 56-58, 80 and 83, and 104-106 and 108 are shown with their amino acid side chain;

FIG. 6 depicts the sequence scheme for the random library that was constructed for the generation of CD4-binding muteins of tear lipocalin in comparison to the recombinant Tlc gene (SEQ ID NO: 64, amino acid translation: SEQ ID NO: 65): AN-15F (SEQ ID NO: 26), AN-10 (SEQ ID NO:

27), AN-11 (SEQ ID NO: 28), AN-12 (SEQ ID NO: 29), AN-14 (SEQ ID NO: 30), AN-21 (SEQ ID NO: 31) and AN-22F (SEQ ID NO: 32).

Figure 10:
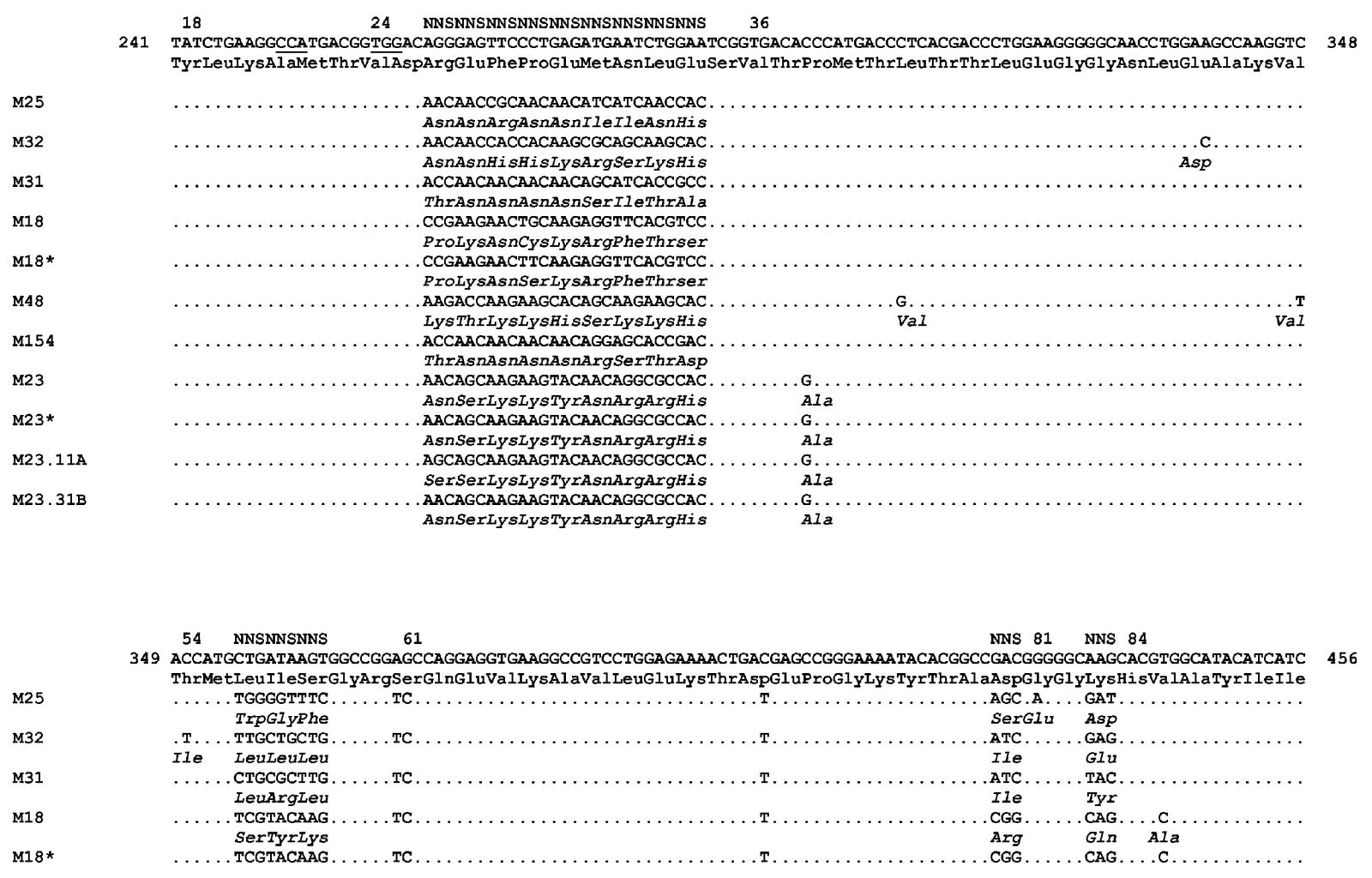

FIG. 10 shows the nucleotide (M25: SEQ ID NO: 5, M32: SEQ ID NO: 7, M31: SEQ ID NO: 9, M18: SEQ ID NO: 11, M18*: SEQ ID NO: 13, M48: SEQ ID NO: 15, M154: SEQ ID NO: 17, M23: SEQ ID NO: 19, M23*: SEQ ID NO: 21, M23.11A: SEQ ID NO: 23, M23.11B: SEQ ID NO: 25) and amino acid sequences (M25: SEQ ID NO: 4, M32: SEQ ID NO: 6, M31: SEQ ID NO: 8, M18: SEQ ID NO: 10, M18*: SEQ ID NO: 12, M48: SEQ ID NO: 14, M154: SEQ ID NO: 16, M23: SEQ ID NO: 18, M23*: SEQ ID NO: 20, M23.11A: SEQ ID NO: 22, M23.11B: SEQ ID NO: 24) of exemplary tear lipocalin muteins of the invention in comparison to the recombinant Tlc gene (SEQ ID NO: 64, amino acid translation: SEQ ID NO: 65).

Figure 11:
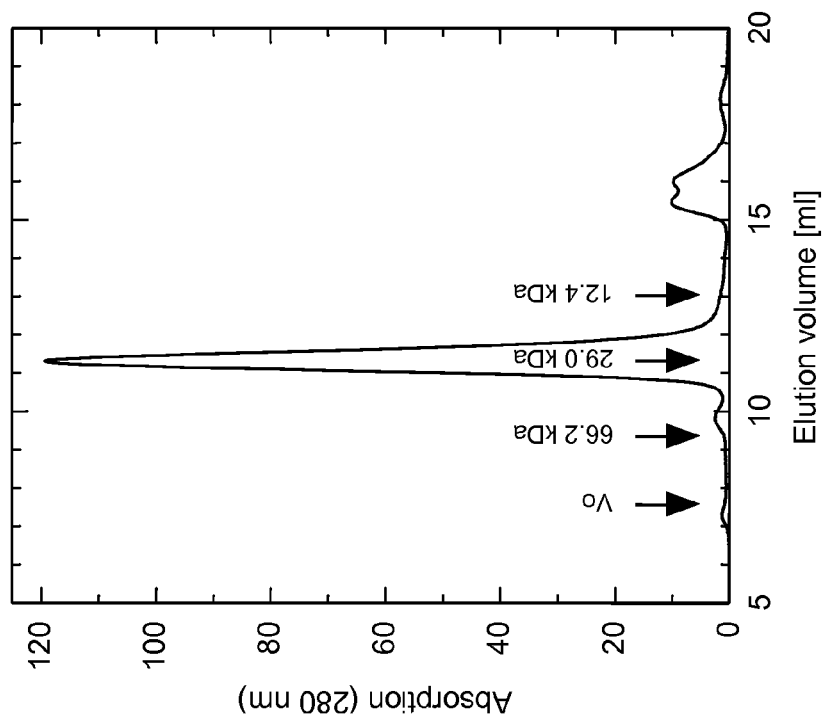
Figure 11:
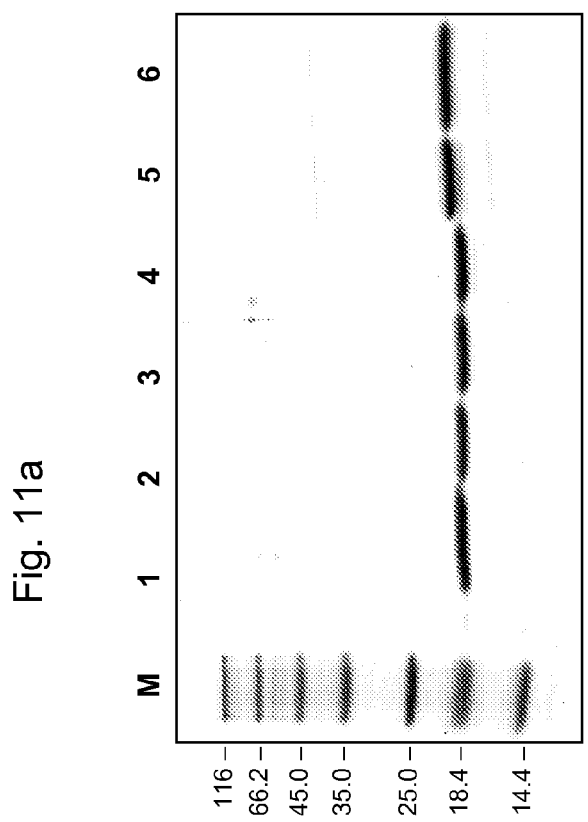
Figure 12A:
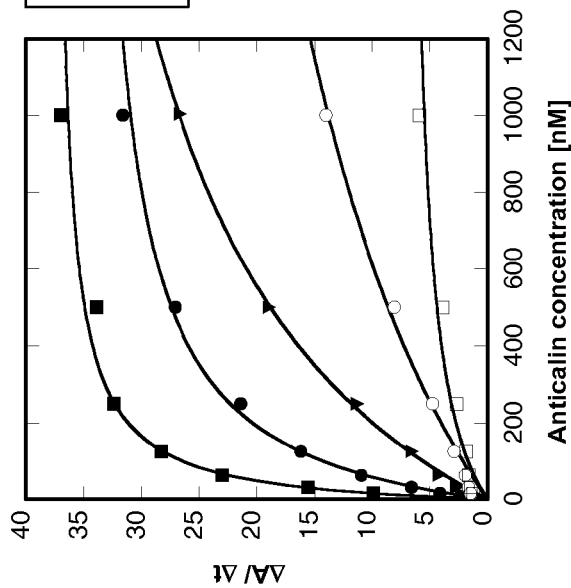
Figure 12B:
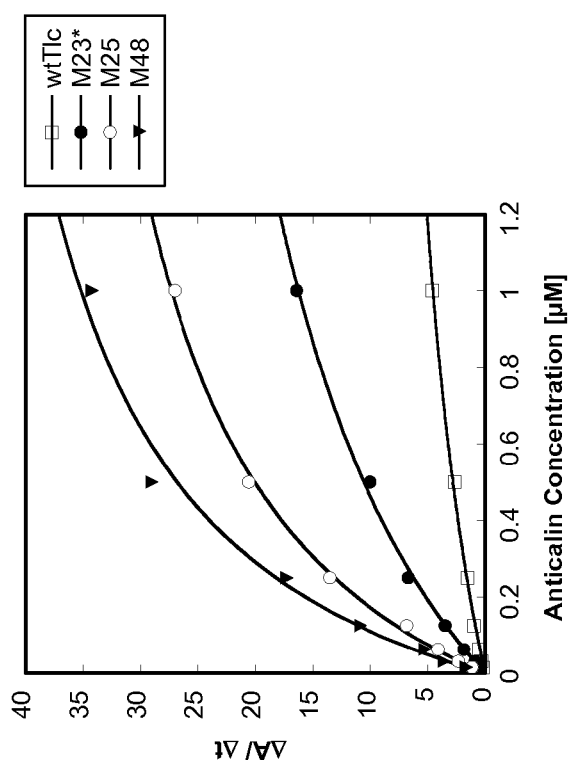
Figure 13:
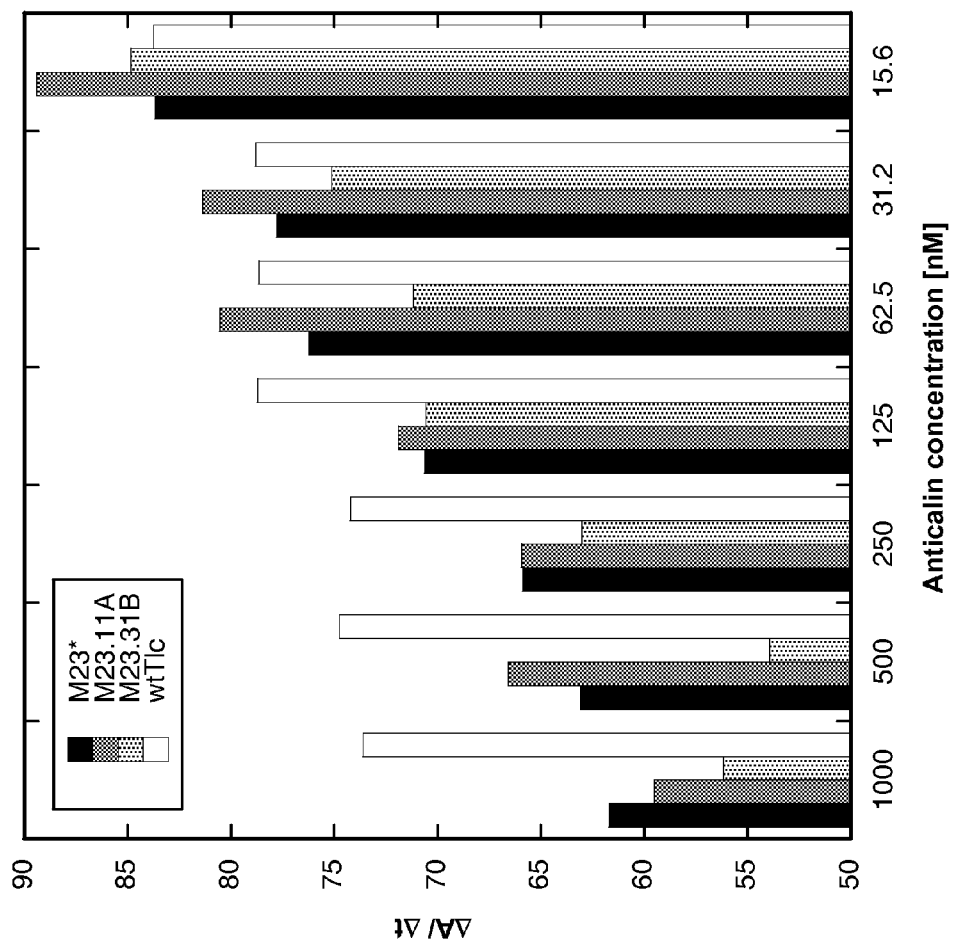
Figure 14:
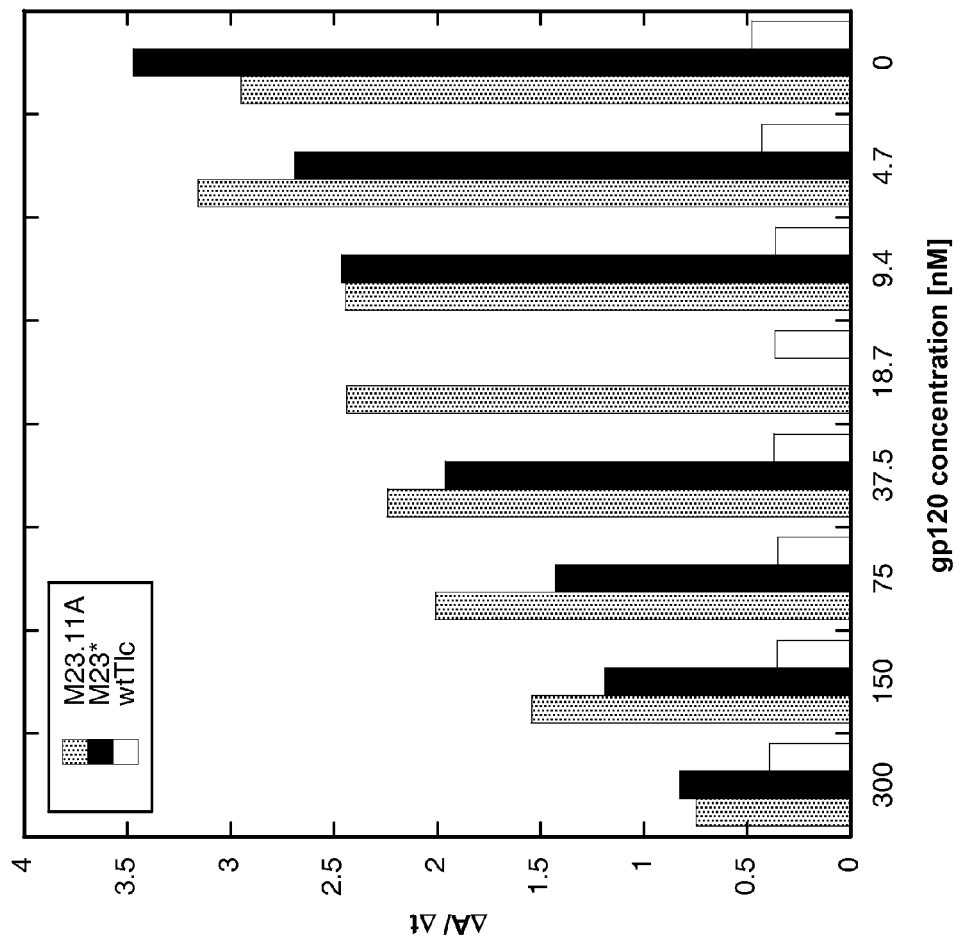
Figure 16:
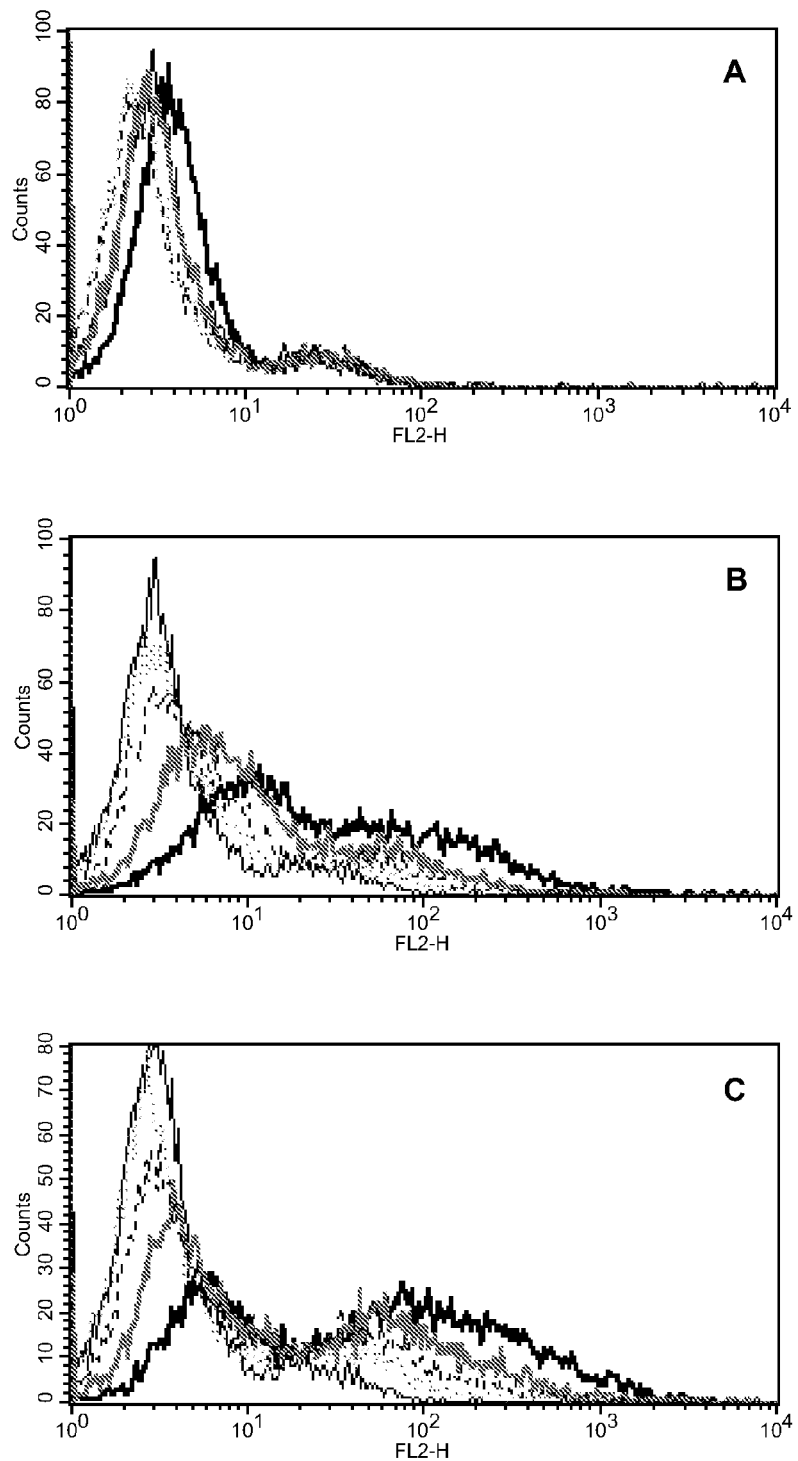
Figure 16:
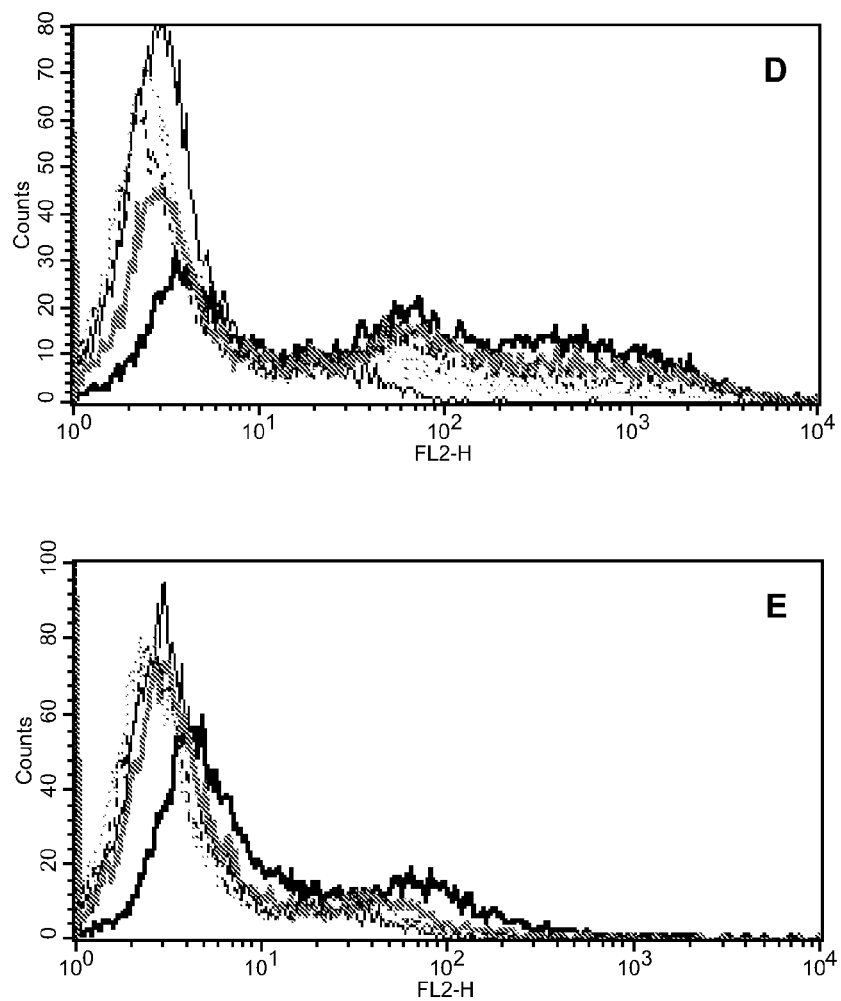

FIG. 11 shows the purification of the tear lipocalin muteins M18, M18*(Cys29Ser), M23, M23*(Cys57Ser) and M25 after production in *E. coli* JM83 (FIG. 11A: SDS PAGE, FIG. 11B: size exclusion chromatography);

FIG. 12 shows an ELISA to determine the affinity of the tear lipocalin muteins M23*, M25, M48 (FIG. 12a), M23.11A, M23*, M23.31B and M25 (FIG. 12b) for recombinant CD4;

FIG. 13 shows an ELISA in which competitive CD4-binding behaviour of the Tlc muteins M23*, M23.11A and M23.31B was tested with an epitope-specific anti-CD4 antibody;

FIG. 14 shows an ELISA in which competitive CD4-binding behaviour of the Tlc muteins M23.11A and M23* was tested with recombinant gp120;

Figure 15:
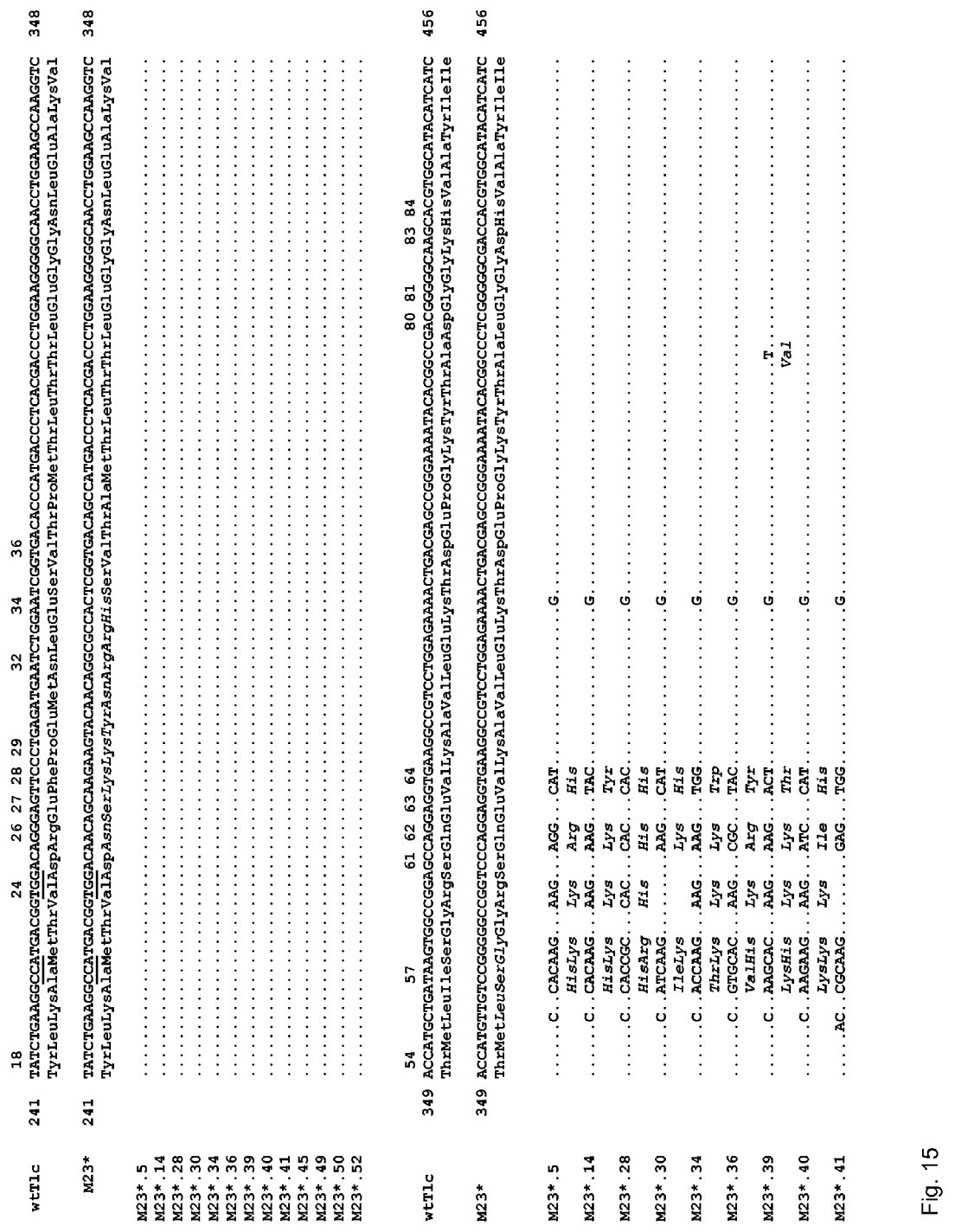
Figure 15:
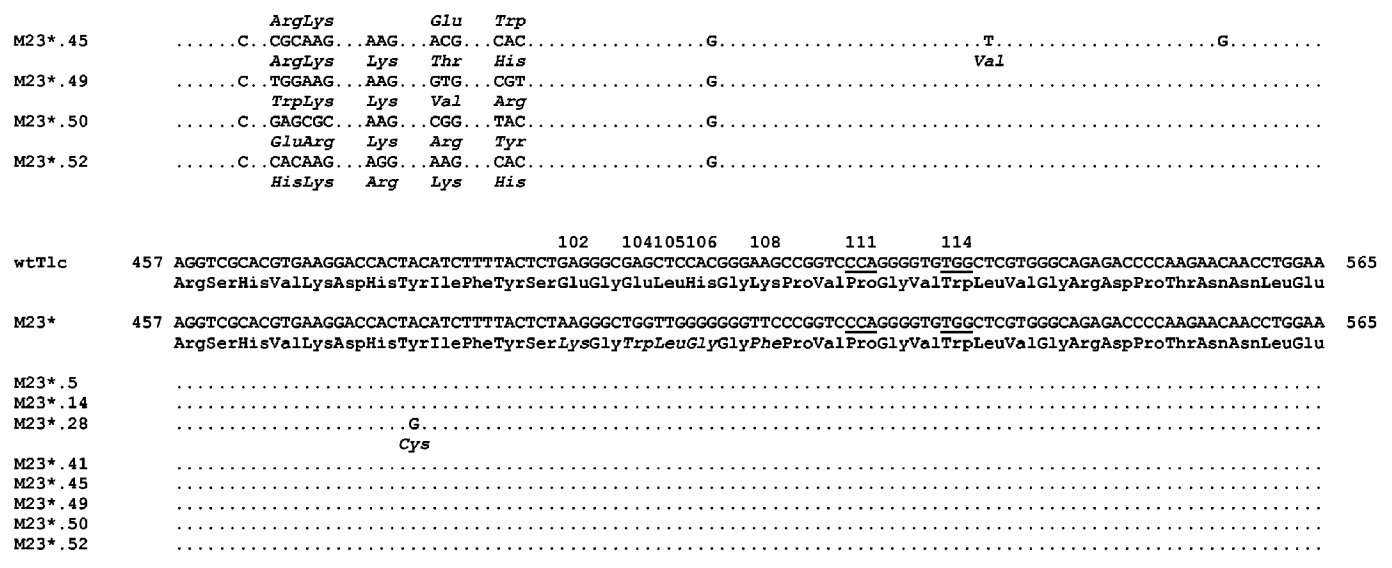

FIG. 15 shows the nucleotide and amino acid sequences of the Tlc muteins M23*.5 (SEQ ID NOs: 38 and 39), M23*.14 (SEQ ID NOs: 40 and 41), M23*.28 (SEQ ID NOs: 42 and 43), M23*.30 (SEQ ID NOs: 44 and 45), M23*.34 (SEQ ID NOs: 46 and 47), M23*36 (SEQ ID NOs: 48 and 49), M23.*39 (SEQ ID NOs: 50 and 51), M23*40 (SEQ ID NOs: 52 and 53), M23*41 (SEQ ID NOs: 54 and 55), M23*.45 (SEQ ID NOs: 56 and 57), M23*.49 (SEQ ID NOs: 58 and 59), M23*.50 (SEQ ID NOs: 60 and 61) and M23*.52 (SEQ ID NO: 62 and 63) in comparison to the recombinant Tlc gene (SEQ ID NO: 64, amino acid translation: SEQ ID NO: 65), and FIG. 16 shows the binding of Tlc muteins M23*(B), M23*.41 (C), M23*.49 (D), and M23*.39 (E) in comparison with the wild type (A) Tlc to PM1 cells expressing CD4.

DETAILED DESCRIPTION OF THE INVENTION

The term "mutagenesis" as used herein means that the experimental conditions are chosen such that the amino acid naturally occurring at a given sequence position of human tear lipocalin (Swiss-Prot data bank entry P31025) can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the invention that, for example, one amino acid at a chosen sequence position is replaced by a stretch of three random mutations, leading to an insertion of two amino acid residues compared to the length of the respective segment of the wild type protein. Such an insertion of deletion may be introduced independently from each other in any of the peptide segments that can be subjected to mutagenesis in the invention. In one exemplary embodiment of the invention, an insertion of several mutations may be introduced into the loop AB of the chosen lipocalin scaffold (cf. International Patent Application WO 2005/019256 which is incorporated by reference its entirety herein). The term "random mutagenesis" means that no predetermined single amino acid (mutation) is present at a certain sequence position but that at least two amino acids can be incorporated with a certain probability at a predefined sequence position during mutagenesis.

Such experimental conditions can, for example, be achieved by incorporating codons with a degenerate base composition into a nucleotide acid encoding the respective lipocalin employed. For example, use of the codon NNK or NNS (wherein N=adenine, guanine, cytosine or thymine; K=guanine or thymine; S=guanine or cytosine) allows incorporation of all 20 amino acids plus the amber stop codon (TAG) during mutagenesis, whereas e.g. the codon VVS (wherein V=adenine, cytosine or guanine) limits the number of possibly incorporated amino acids to 12, since it excludes the amino acids Cys, Ile, Leu, Met, Phe, Trp, Tyr, Val from being incorporated into the selected position of the polypeptide sequence; use of the codon NMS (wherein M=adenine or cytosine), for example, restricts the number of possible amino acids to 11 at a selected sequence position since it excludes the amino acids Arg, Cys, Gly, Ile, Leu, Met, Phe, Trp, Val from being incorporated. In this respect it is noted that specialized codons for non-proteinogenous/proteinaceous/natural amino acids (other than the regularly occurring set of 20 amino acids), such as selenocysteine or pyrrolysine, can also be incorporated into a nucleic acid of a mutein. It is also possible, as described by Wang, L., et al. (2001) *Science* 292, 498-500, or Wang, L., and Schultz, P. G. (2002) *Chem. Comm.* 1, 1-11, to use "artificial" codons such as UAG which are usually recognized as stop codons in order to insert other non-natural amino acids, for example o-methyl-L-tyrosine or p-aminophenylalanine.

The lipocalin muteins of the invention are able to bind the T-cell co-receptor CD4 as a prescribed/cognate target with detectable affinity, i.e. with an affinity constant of preferably at least $10^5$ M$^{-1}$. Lower affinities are not easily measurable with common methods such as ELISA and are therefore of less importance. In some embodiments lipocalin muteins are preferred which bind CD4 with an affinity of at least $10^6$ M$^{-1}$, corresponding to a dissociation constant ($K_D$) of the complex of 1 μM. In further embodiments, the tear lipocalin mutein of the invention binds human CD4 with a $K_D$ of 750 nM or less, 500 nM or less, 250 nM or less, with a $K_D$ of 100 nM or less or even with a $K_D$ of 25 nM or less. The binding affinity of a mutein to the prescribed target can be measured by a multitude of methods such as ELISA, competition ELISA, fluorescence titration or surface plasmon resonance.

It is obvious to the skilled person in the art that complex formation is dependent on many factors such as concentration of the binding partners, the presence of competitors, ionic strength of the buffer system, pH value etc. Selection and enrichment is generally performed under conditions allowing the isolation of tear lipocalin muteins having an affinity constant of at least $10^5$ M$^{-1}$ to the target. However, the washing and elution steps can be carried out with varying stringency. A selection with respect to the kinetic characteristics, instead of equilibrium conditions for complex formation, is possible as well. For example, the selection can be performed under conditions which favor complex formation of the target with muteins that show a slow dissociation from the target, or in other words a that have a low $k_{off}$ rate constant.

In line with the above disclosure, a mutein of the invention may comprise at least 2, 5, 8, 10, 12, 14, 15, 16, 18, 20 or 22 mutated amino acid residues with respect to the wild type amino acid sequence of mature human tear lipocalin at any of the sequence positions 24-36, 53-66, 79-84, and 102-110 (or 103-110) of the linear polypeptide sequence of human tear lipocalin. More particular, the mutein may comprise at least 2, 5, 8, 10, 12, 14, 15, 16, 18, 20 or 22 mutated amino acid residues amino acid with respect to the wild type amino acid sequence of mature human tear lipocalin at any of the sequence positions 26, 27, 28, 29, 30, 31, 32, 33, 34, 56, 57, 58, 60, 61, 62, 64, 80, 83, 102, 104, 105, 106, 107 and 108 of the mature amino acid sequence of human tear lipocalin. It should however be noted that not all of the amino acids of the wild-type protein must be or will necessarily be mutated in order to generate a mutein that displays affinity towards CD4. Rather, it is possible that some of the amino acid residues of the wild-type protein will be retained even in muteins that bind (a particular epitope of) CD4 with high affinity. For example, the mutein M18 carries the wild-type leucine residue at position 105 of the tear lipocalin sequence. In accordance with this, only in some embodiments the tear lipocalin mutein comprises amino mutated amino acid residues at all 24 of the sequence positions 26, 27, 28, 29, 30, 31, 32, 33, 34, 56, 57, 58, 60, 61, 62, 64, 80, 83, 102, 104, 105, 106, 107 and 108, if all these sequence positions are subjected to mutagenesis. It is however again noted in this context that not all of these 24 sequence positions have to be subjected to mutagenesis but it is also possible to subject only a subset of the sequence positions to mutagenesis, for example, the 18 sequence positions 26, 27, 28, 29, 30, 31, 32, 33, 34, 56, 57, 58, 80, 83, 104, 105, 106, and 108. It is also noted in this context that not all of the sequence positions have to be subjected to mutagenesis at the same time. Rather, it is also possible to first select a subset of sequence positions for creation of a naïve library from which CD4 binding muteins can be generated. In a second step a nucleic acid coding for a CD4 binding mutein can then be subjected to a further mutagenesis for affinity maturation using a second subset of sequence positions for the mutagenesis. See the experimental section in this regard, where first a naïve library is created by mutagenising sequence positions 26, 27, 28, 29, 30, 31, 32, 33, 34, 56, 57, 58, 80, 83, 104, 105, 106, and 108 (Example 2) and then an affinity maturation by separately mutating the coding sequence of amino acid 57, 58, 60, 61, 62, and 64 and mutating sequence positions 102, 104, 105, 106, and 107 is carried out (Example 9). As can also be seen from Example 9, it may be the case that despite mutagenesis selected muteins may retain the wild type sequence at the selected sequence positions.

In some muteins of tear lipocalin that bind CD4 the amino acid present at sequence position 27 is selected from Asn, Lys, or an amino acid having a free hydroxyl group, for example Thr or Ser. At sequence position 34 of such Tlc muteins a His, Ala, Ser or Asp can be present. In position 28 of tear lipocalin muteins Asn or a basic amino acid such as Arg, His or Lys can be present and in position 29 Asn, Ser, Cys or a basic amino acid such as His or Lys occurs In some of these muteins sequence positions 28 to 34 comprise the sequence Lys-Lys-Tyr-Asn-Arg-Arg-His (cf. FIG. 10). In other such muteins the stretch of sequence positions 28 to 34 has the amino acid sequence Asn-(Cys/Ser)-Lys-Arg-Phe-Tyr-Ser (cf. FIG. 10).

A hydrophobic amino acid such as Trp, Leu, Val or Ala can be present at sequence positon 56 of CD4 binding muteins of the invention. Alternatively, a Ser residue can be present at sequence position 56. At sequence position 57 a CD 4 binding tear lipocalin mutein may comprise a Leu, Tyr, Gly, Ser or Cys residue and at sequence position 58 a CD4 binding tear lipocalin mutein may comprise a Phe, Leu, Lys or Gly residue (cf., FIG. 10). A mutein of the invention can independently from each other also comprise a positively charged/basic amino acid at each of sequence positions 57 and 58. A positively charged amino acid may also be present at sequence positions 60 (here other than the wild type Arg 60), at sequence position 62 and also at sequence position 64.

In some embodiments of CD4 binding muteins the Asp residue present at sequence position 80 in the wildtyp tear lipocalin can be replaced by Ser, or a hydrophobic amino acid such as Ile or Leu, or a basic amino acid, e.g. Arg or His.

In some muteins that bind CD4 and preferably show antagonistic properties towards CD4 a hydrophobic amino acid is present at any of the sequence positions 104, 105, 106 and 108. Examples of hydrophobic amino acid residues at sequence positions 105 include Leu (i.e. the residue that is present in the wild type amino acid sequence at this position, see above) or Val, Trp or Tyr in case of a mutation compared to the wild type sequence.

In other muteins that bind to CD4 and preferably also inhibit the binding of gp120 to CD4 an amino acid having a free hydroxyl group occurs at sequence position 104. Examples of corresponding amino acid residues are Ser and Tyr.

It is also possible that a mutein of the invention includes a basic amino acid residue at the sequence position 106, for example His or Arg.

The tear lipocalin mutein of the invention may comprise with respect to the wild type amino acid sequence of human tear lipocalin at least 1, 2, 5, 8, 10, 12, 14, 15, 16, 17, or 18 amino acid replacements selected from the group consisting of Glu 27→Asn, Glu 27→Lys, Glu 27→Thr, Glu 27→Ser, Phe 28→His, Phe 28→Lys, Phe 28→His, Phe 28→Arg, Phe 28→Asn, Pro29→Asn, Pro29→Cys, Pro29→Ser, Pro29→Lys, Glu 30→Asn, Glu 30→His, Glu 30→Lys, Glu 30→Tyr, Met 31→Ile, Met 31→Arg, Met 31→Ser, Met 31→Asn, Asn 32→Phe, Asn 32→Ile, Asn 32→Ser, Asn 32→Arg, Leu 33→Thr, Leu 33→Lys, Leu 33→Arg, Leu 33→Asn, Glu34→Ser, Glu34→His, Glu34→Ala, Glu34→Asp, Leu 56→Ser, Leu 56→Trp, Leu 56→Ala, Leu 56→Val, Ile 57→Gly, Ile 57→Tyr, Ile 57→Ser, Ile 57→Cys, Ile 57→Leu, Ile 57→His, Ile 57→Lys, Ile 57→Val, Ile 57→Arg, Ile 57→Trp, Ile 57→Glu, Ser 58→Phe, Ser 58→Phe, Ser 58→Lys, Ser 58→Leu, Ser 58→Gly, Ser 58→Lys, Ser 58→His, Ser 58→Arg, Arg 60→Lys, Arg 60→His, Gln 62→Lys, Gln 62→Arg, Gln 62→His, Gln 62→Ile, Gln 62→Thr, Gln 64→His, Gln 64→Arg, Gln 64→Trp, Gln 64→Tyr, Asp 80→Ile, Asp 80→Leu, Asp 80→Arg, Asp 80→His, Asp 80→Ser, Glu 102→Lys, Glu 104→Ser, Glu 104→Ala, Glu 104→Leu, Glu 104→Trp, Glu 104→Tyr, Glu 104→Ile, Leu 105→Val, Leu 105→Trp, Leu 105→Phe, His 106→Gly, His 106→Leu, His 106→Ile, His 106→Arg, Lys 108→Val, Lys 108→Leu, Lys 108→Ile, Lys 108→Trp, and Lys 108→Phe.

In this context it is noted that the number of four segments (loops) that are arranged on one end of the characteristic β-barrel structure of the lipocalin and that are used for mutagenesis can vary. It is not always necessary to mutate all four of segments that comprise the sequence positions 24-36, 53-66, 79-84, and 102-110 (or 103-110) at once. Rather, it is also possible to introduce mutations only in one, two or three of these segments in order to generate a mutein having detectable affinity to the extracellular region of CD4.

The lipocalin muteins of the invention may exhibit the wild type (natural) amino acid sequence outside the mutated segments. On the other hand, the lipocalin muteins disclosed herein may also contain amino acid mutations outside the sequence positions subjected to random mutagenesis as long as those mutations do not interfere with the binding activity and the folding of the mutein. Such mutations can be accomplished very easily on the DNA level using established standard methods (Sambrook, J. et al. (1989) *Molecular Cloning: A Laboratory Manual,* 2nd Ed., Cold Spring Harbor Laboratory Press, Cold Spring Harbor, N.Y.). Possible alterations of the amino acid sequence are insertions or deletions as well as amino acid substitutions. Such substitutions may be conservative, i.e. an amino acid residue is replaced with a biochemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. However, it is also possible to introduce non-conservative alterations into the amino acid sequence as long as they do not prevent protein folding.

Such modifications of the amino acid sequence may indeed be useful and can include directed mutagenesis of single amino acid positions in order to simplify sub-cloning of the mutated lipocalin gene or its parts by incorporating cleavage sites for certain restriction enzymes. For example the mutations Arg111→Pro and Lys114→Trp may be introduced for this purpose. In addition, mutations can also be incorporated to further improve the affinity of a tear lipocalin mutein for CD4. Mutations can also be introduced in order to modulate certain characteristics of the mutein such as to improve folding stability or solubility or to reduce aggregation tendency, if necessary. Similarly, Cys residues which may occur as a result of the mutagenesis and selection of the mutein of the invention are not always crucial for the binding of the given target and may be substituted by Ser or Ala in order to prevent covalent bond formation or oxidation of the thiol group. See for example, the free Cys residue that is found at position 29 in the mutein M18, which can be replaced by a Ser residue without significantly affecting the binding to CD4. Also, the naturally occurring disulfide bridge between Cys residues 61 and 153 of tear lipocalin can, for example, be removed by substituting one or both of these amino acids by Ser, leading to the mutations Cys61→Ser and/or Cys153→Ser and thus facilitating recombinant production of a mutein of the invention because no longer an oxidizing environment is needed. On the other hand, Cys residues may also deliberately introduced, for example, into the β-barrel, into the α-helix or at the N- or C-terminus of tear lipocalin, in order to provide a reactive group, for instance, for the site-specific PEGylation of lipocalin muteins of the invention. In yet other muteins of the invention, for example the muteins M32, M18, M23, M23*, M23.11A, the residue Glu102 has been replaced by Lys.

In illustrative embodiments, a tear lipocalin mutein of the invention has an amino acid sequence selected from the group consisting of the sequences M25 (SEQ ID NO: 5), M32 (SEQ ID NO: 7), M31 (SEQ ID NO: 9), M18 (SEQ ID NO: 11), M18* (SEQ ID NO: 13), M48 (SEQ ID NO: 15), M154 (SEQ ID NO: 17), M23 (SEQ ID NO: 19), M23* (SEQ ID NO: 21), M23.11A (SEQ ID NO: 23), and M23.11B (SEQ ID NO: 25) as depicted in FIG. 10. In other illustrative embodiments, a tear lipocalin mutein of the invention has an amino acid sequence selected from the group of the sequences sequences M23*.5 (SEQ ID NO: 39), M23*.14 (SEQ ID NO: 41), M23*.28 (SEQ ID NO: 43), M23*.30 (SEQ ID NO: 45), M23*.34 (SEQ ID NO: 47), M23*.36 (SEQ ID NO: 49), M23*.39 (SEQ ID NO: 51), M23*.40 (SEQ ID NO: 53), M23*.41 (SEQ ID NO: 55), M23*.45 (SEQ ID NO: 57), M23*.49 (SEQ ID NO: 59), M23*.50 (SEQ ID NO: 61) and M23*.52 (SEQ ID NO: 63) as depicted in FIG. 15.

A tear lipocalin mutein of the invention typically exists as monomeric protein. However, it is also possible that an inventive lipocalin mutein is able to spontaneously dimerise or oligomerise. Although the use of lipocalin muteins that form stable monomers may be preferred for some applications, e.g. because of faster diffusion and better tissue penetration, the use of lipocalin muteins that form stable homodimers or multimers may be preferred in other instances. For example, such multimers can provide increased affinity and/or avidity to CD4. Furthermore, oligomeric forms of the lipocalin mutein may have slower dissociation rates or prolonged serum half-life.

For some applications, it is useful to employ the muteins of the invention in a labeled form. Accordingly, the invention is also directed to lipocalin muteins which are conjugated to a label selected from the group consisting of enzyme labels, radioactive labels, colored labels, fluorescent labels, chromogenic labels, luminescent labels, haptens, digoxigenin, biotin, metal complexes, metals, and colloidal gold. The mutein may also be conjugated to an organic molecule. The term "organic molecule" as used herein preferably denotes an organic molecule comprising at least two carbon atoms, but preferably not more than seven or 12 rotatable carbon bonds, having a molecular weight in the range between 100 and 2000 Dalton, preferably 1000 Dalton, and optionally including one or two metal atoms.

In general, it is possible to label the tear lipocalin mutein with any appropriate chemical substance or an enzyme which directly or indirectly generates a detectable compound or signal in a chemical, physical or catalytic reaction. Examples for physical reactions are the emission of fluorescence upon irradiation or the emission of γ-rays when using a radioactive label. Alkaline phosphatase, horseradish peroxidase or β-galactosidase are examples of enzyme labels that catalyze the formation of chromogenic reaction products. In general, all labels commonly used for antibodies (except those exclusively used in conjunction with with the sugar moiety in the Fc part of immunoglobulins) can also be used for conjugation to the muteins of the present invention. Furthermore, the muteins of the invention may be conjugated with another suitable therapeutically active agent for the treatment of HIV. The lipocalin muteins of the invention may also be conjugated with therapeutically active nucleic acids such as antisense nucleic acid molecules, small interfering RNAs, micro RNAs or ribozymes. Such conjugates can be produced by methods well known in the art.

As identicated above, a mutein of the invention may in some embodiments be conjugated to a moiety that extends the serum half-life of the mutein. The moiety that extends the serum half-life may be a polyalkylene glycol molecule, hydroxyethylstarch, an Fc part of an immunoglobulin, a CH3 domain of an immunoglobulin, a CH4 domain of an immunoglobulin, albumin, an albumin binding peptide, or an albumin binding protein, to name only a few. The albumin binding protein may be a bacterial albumin binding protein or a lipocalin mutein with binding activity for albumin. Accordingly, suitable conjugation partners for extending the half-life of a CTLA-4 binding lipocalin mutein of the invention include albumin (Osborn, B. L. et al. (2002) Pharmacokinetic and pharmacodynamic studies of a human serum albumin-interferon-alpha fusion protein in cynomolgus monkeys *J. Pharmacol. Exp. Ther.* 303, 540-548), or an albumin binding protein, for example, a bacterial albumin binding domain, such as the one of streptococcal protein G (König, T. and Skerra, A. (1998) Use of an albumin-binding domain for the selective immobilisation of recombinant capture antibody fragments on ELISA plates. *J. Immunol. Methods* 218, 73-83). Other examples of albumin binding peptides that can be used as conjugation partner (Dennis, M. S., Zhang, M., Meng, Y. G., Kadkhodayan, M., Kirchhofer, D., Combs, D. & Damico, L. A. (2002). Albumin binding as a general strategy for improving the pharmacokinetics of proteins. *J Biol Chem* 277, 35035-35043) are, for instance, those having a Cys-$Xaa_1$-$Xaa_2$-$Xaa_3$-$Xaa_4$-Cys consensus sequence, wherein $Xaa_1$ is Asp, Asn, Ser, Thr, or Trp; $Xaa_2$ is Asn, Gln, His, Ile, Leu, or Lys; $Xaa_3$ is Ala, Asp, Phe, Trp, or Tyr; and $Xaa_4$ is Asp, Gly, Leu, Phe, Ser, or Thr as described in U.S. patent application 2003/0069395.

If polyalkylene glycol is used as conjugation partner, the polyalkylene glycol can be substituted or unsubstituted. It can also be an activated polyalkylene derivative. Examples of suitable compounds are polyethylene glycol (PEG) molecules as described in WO 99/64016, in U.S. Pat. No. 6,177,074 or in U.S. Pat. No. 6,403,564 in relation to interferon, or as described for other proteins such as PEG-modified asparaginase, PEG-adenosine deaminase (PEG-ADA) or PEG-superoxide dismutase (see for example, Fuertges et al. (1990) The Clinical Efficacy of Poly(Ethylene Glycol)-Modified Proteins *J. Control. Release* 11, 139-148). The molecular weight of such a polymer, preferrably polyethylene glycol, may range from about 300 to about 70.000 Dalton, including, for example, polyethylene glycol with a molecular weight of about 10.000, of about 20.000, of about 30.000 or of about 40.000 Dalton. Moreover, as e.g. described in U.S. Pat. Nos. 6,500,930 or 6,620,413, carbohydrate oligo- and polymers such as starch or hydroxyethyl starch (HES) can be conjugated to a mutein of the invention for the purpose of serum half life extension.

For several applications of the muteins disclosed herein it may be advantageous to use them in the form of fusion proteins. In preferred embodiments, the inventive lipocalin mutein is fused at its N-terminus or its C-terminus to a protein, a protein domain or a peptide, for example a signal sequence and/or an affinity tag.

For pharmaceutical applications a mutein of the invention may be fused to a fusion partner that extends the in vivo serum half-life of the mutein. Similar to the conjugates described above, the fusion partner may be an Fc part of an immunoglobulin, a CH3 domain of an immunoglobulin, a CH4 domain of an immunoglubolin, albumin, an albumin binding peptide or an albumin binding protein, to name only a few. Again, the albumin binding protein may be a bacterial albumin binding protein or a lipocalin mutein with binding activity for albumin. Accordingly, suitable fusion partners for extending the half-life of a CTLA-4 binding lipocalin mutein of the invention include albumin (Osborn, B. L. et al. (2002) supra *J. Pharmacol. Exp. Ther.* 303, 540-548), or an albumin binding protein, for example, a bacterial albumin binding domain, such as the one of streptococcal protein G (König, T. and Skerra, A. (1998) supra *J. Immunol. Methods* 218, 73-83). The albumin binding peptides described in Dennis et al, supra (2002) or U.S. patent application 2003/0069395 having a Cys-$Xaa_1$-$Xaa_2$-$Xaa_3$-$Xaa_4$-Cys consensus sequence, wherein $Xaa_1$ is Asp, Asn, Ser, Thr, or Trp; $Xaa_2$ is Asn, Gln, His, Ile, Leu, or Lys; $Xaa_3$ is Ala, Asp, Phe, Trp, or Tyr; and $Xaa_4$ is Asp, Gly, Leu, Phe, Ser, or Thr can also be used as fusion partner.

The fusion partner may also confer new characteristics to the inventive lipocalin mutein such as enzymatic activity or affinity for other molecules. Examples of suitable fusion proteins are alkaline phosphatase, horseradish peroxidase, gluthation-S-transferase, the albumin-binding domain of protein G, protein A, antibody fragments, oligomerization domains, lipocalin muteins of same or different binding specificity (which results in the formation of "duocalins", cf. Schlehuber, S., and Skerra, A. (2001), Duocalins, engineered ligand-binding proteins with dual specificity derived from the lipocalin fold. *Biol. Chem.* 382, 1335-1342), or toxins.

Affinity tags such as the STREP-TAG® or STREP-TAG® II (Schmidt, T. G. M. et al. (1996) *J. Mol. Biol.* 255, 753-766 or Skerra, A. & Schmidt, T. G. M. (2000) Use of the STREP-TAG® and streptavidin for detection and purification of recombinant proteins. *Methods Enzymol.* 326A, 271-304), the myc-tag, the FLAG®-tag (a polypeptide protein tag that can be added to a protein using recombinant DNA technology), the $His_6$-tag or the HA-tag or proteins such as glutathione-S-transferase also allow easy detection and/or purification of recombinant proteins and are further examples of preferred fusion partners. Proteins with chromogenic or fluorescent properties such as the green fluorescent protein (GFP) or the yellow fluorescent protein (YFP) are suitable fusion partners for a lipocalin mutein of the invention, as well.

The present invention also relates to nucleic acid molecules (DNA and RNA) comprising nucleotide sequences coding for a CD4 binding tear lipocalin mutein as described herein. Since the degeneracy of the genetic code permits substitutions of certain codons by other codons specifying the same amino acid, the invention is not limited to a specific nucleic acid molecule encoding a mutein of the invention but includes all nucleic acid molecules comprising nucleotide sequences encoding functional CD4 binding lipocalin muteins as described herein.

In one embodiment of the invention, the nucleic acid sequences encode tear lipocalin muteins which inhbit the interaction between CD4 and gp 120 of HIV. In other embodiments, nucleic acid molecules encode muteins that bind (human) CD4 with a $K_D$ of 750 nM or less, 500 nM or less, 250 nM or less, with a $K_D$ of 100 nM or less with a $K_D$ of 25 nM or less. In some illustrative embodiments the nucleic acid molecule comprises a nucleotide sequence selected from the group of SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22 and SEQ ID NO: 24 each encoding a respective tear lipocalin mutein that has an amino acid sequence selected from the group consisting of the sequences M25, M32, M31, M18, M18*, M48, M154, M23, M23*, M23.11A, and M23.11B as depicted in FIG. 10. In some other illustrative embodiments a nucleic acid molecule comprises a nucleotide sequence selected from the group of SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60 and SEQ ID NO: 62 each encoding a respective tear lipocalin mutein having an amino acid sequence selected from the group of the sequences M23*.5, M23*.14, M23*.28, M23*.30, M23*.34, M23*36, M23.*39, M23*40, M23*41, M23*.45, M23*.49, M23*.50 and M23*.52 as depicted in FIG. 15.

The invention is also directed to a nucleic acid molecule comprising a sequence encoding a mutein according to the invention or a fusion protein thereof. The invention further includes nucleic acid molecules encoding lipocalin muteins that comprise additional nucleotide mutations at sequence positions other than those mentioned above. Such mutations are often tolerated or can even prove to be advantageous, for example, if they contribute to an improved folding efficiency, protein stability or ligand affinity of the mutein.

A nucleic acid molecule disclosed in this application may be "operably linked" to a regulatory sequence (or regulatory sequences) to allow expression of this nucleic acid molecule in a host cell or organism or even in a cell-free in vitro system.

A nucleic acid molecule, such as DNA, is referred to as "capable of expressing genetic information, giving rise to transcription and/or translation of an encoded protein," or capable "to allow expression of a nucleotide sequence" if it comprises sequence elements which contain information regarding transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions comprise a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in the initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal or leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactorily functional in a particular host cell, they may be substituted with other signals that are functional in that cell.

Therefore, a nucleic acid molecule of the invention can include a regulatory sequence, preferably a promoter sequence. In another preferred embodiment, a nucleic acid molecule of the invention comprises a promoter sequence and a transcriptional termination sequence. Suitable prokaryotic promoters are, for example, the tet promoter, the lacUV5 promoter or the T7 promoter. Examples of promoters useful for expression in eukaryotic cells are the SV40 promoter or the CMV promoter.

The nucleic acid molecule of the invention can also be part of a vector or any kind of cloning vehicle, such as a plasmid, a phagemid, a phage, baculovirus, a cosmid or an artificial chromosome. Apart from the regulatory sequences described above and the nucleic acid sequence encoding a lipocalin mutein of the invention, such cloning vehicles can include replication and control sequences derived from a species compatible with the host cell that is used for expression as well as selection markers conferring a selectable phenotype on transformed or transfected cells. Large numbers of suitable cloning vectors are known in the art and are, in many cases, commercially available.

The DNA molecule encoding a CD4 binding lipocalin mutein of the invention, and in particular a cloning vector containing the coding sequence for such a mutein, can be transfected into a host cell capable of expressing the gene. Transformation can be performed using standard techniques (Sambrook, J. et al. (1989), supra). Thus, the invention is also directed to a host cell containing a nucleic acid molecule as disclosed herein.

The transformed host cells are cultured under conditions suitable for expression of the nucleotide sequence encoding a fusion protein of the invention. Suitable host cells can be prokaryotic, such as *E. coli* or *Bacillus subtilis*, or eukaryotic, such as *Saccharomyces cerevisiae, Pichia pastoris*, SF9 or High5 insect cells, immortalized mammalian cell lines (e.g. HeLa cells or CHO cells) or primary mammalian cells.

The invention also relates to a method for the production of a CD4 binding tear lipocalin mutein of the invention, wherein the mutein, a fragment of the mutein or a fusion protein of the mutein and another polypeptide is produced starting from the nucleic acid coding for the mutein by means of genetic engineering methods. The method can be carried out in vivo, the mutein can for example be produced in a bacterial or eukaryotic host organism and then isolated from this host organism or its culture. It is also possible to produce a protein in vitro, for example by use of an in vitro translation system.

When producing the mutein in vivo a nucleic acid encoding a mutein of the invention is introduced into a suitable bacterial or eukaryotic host organism by means of recombinant DNA technology (as already outlined above). For this purpose, the host cell is transformed with a cloning vector comprising a nucleic acid molecule encoding such a mutein using established standard methods (Sambrook, J. et al. (1989), supra). The host cell is then cultured under conditions which allow expression of the heterologous DNA and thus biosynthesis of the corresponding polypeptide. Subsequently, the polypeptide is recovered either from the cell or from the cultivation medium.

In some tear lipocalin muteins of the invention, the naturally occurring disulfide bond between Cys 61 and Cys 153 is removed. Accordingly, such muteins (or any other tear lipocalin mutein that does not comprise an intramolecular disulfide bond) can be produced in a cell compartment having a reducing redox milieu, for example, in the cytoplasma of Gram-negative bacteria. In case a lipocalin mutein of the invention comprises intramolecular disulfide bonds, it is preferred to direct the nascent polypeptide to a cell compartment having an oxidizing redox milieu using an appropriate signal sequence. Such an oxidizing environment may be provided by the periplasm of Gram-negative bacteria such as *E. coli*, in the extracellular milieu of Gram-positive bacteria or in the lumen of the endoplasmatic reticulum of eukaryotic cells and usually favors the formation of structural disulfide bonds. It is, however, also possible to produce a mutein of the invention in the cytosol of a host cell, preferably *E. coli*. In this case, the polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi M, Seifert C, Hunte C. 2002 High level production of functional antibody Fab fragments in an oxidizing bacterial cytoplasm. J Mol Biol 315, 1-8).

However, a mutein of the invention may not necessarily be produced by use of genetic engineering. Rather, a lipocalin mutein can also be obtained by chemical synthesis such as Merrifield solid phase polypeptide synthesis. For example, it is also possible that promising mutations are first identified using molecular modeling and then the corresponding polypeptide is synthesized in vitro and its binding activity for CD4 is investigated. If desired, chemical synthesis of a lipocalin mutein can also be used for large scale production of the mutein, for example, for the purpose of therapeutic application. Methods for the solid phase and/or solution phase synthesis of proteins are well known in the art (reviewed, e.g., in Lloyd-Williams, P. et al. (1997) Chemical Approaches to the Synthesis of Peptides and Proteins. CRC Press, Boca Raton, Fields, G. B., and Colowick, S. P. (1997) Solid-Phase Peptide Synthesis, Academic Press, San Diego, or Bruckdorfer, T. et al. (2004) Curr. Pharm. Biotechnol. 5, 29-43).

The invention also relates to a pharmaceutical composition comprising a CD4 binding tear lipocalin mutein or a fusion protein or a conjugate thereof and a pharmaceutically acceptable excipient. A mutein of the invention can be administered via any parenteral or non-parenteral (enteral) route that is therapeutically effective for proteinaceous drugs. In one presently preferred embodiment, a pharmaceutical composition that includes a CD4 binding mutein of the invention is adapted for topical administration. The topical application of a CD4 binding tear lipocalin mutein is the route of choice if the mutein is used to prevent HIV infection via sexual transmission. For this purpose, the pharmaceutical composition can, for example, be formulated as an ointment, a lotion, a gel or a cream and be applied on the vaginal mucosa before sexual intercourse. The pharmaceutical composition can also be provided as a depot system that can, for example, be applied as subcutaneous transplant allowing a continous release of the tear lipocalin mutein over a certain period of time. The tear lipocalin can also be incorporated into a vaginal ring from which it is then steadily released after being inserted (high) into vagina. The use of vaginal rings as sustained release devices for systemic or local delivery of pharmaceuticals is well known and has become standard approach for delivery of contraceptives or for hormone therapy (see, for example Maruo, T. et al (2002) "Vaginal rings delivering progesterone and estradiol may be a new method of hormone replacement therapy," *Fertility and Sterility* 78(5): 1010-1016 or Johansson, E. D. B. and Sitruk-Ware, R (2004). "New delivery systems in contraception: Vaginal rings," *American Journal of Obstetrics and Gynecology* 190 (suppl 1): S54-S59.

For therapeutic treatment of patients that are already infected with HIV, systemic application can be achieved by parental administration, for example. Corresponding administration methods include, but are not limited to, for example, intracutaneous, subcutaneous, intramuscular or intravenous injection and infusion techniques, e.g. in the form of injection solutions, infusion solutions or tinctures as well as aerosol installation and inhalation, e.g. in the form of aerosol mixtures, sprays or powders. A combination of intravenous and subcutaneous infusion and/or injection might be most convenient in case of compounds with a relatively short serum half life. The pharmaceutical composition may be an aqueous solution, an oil-in water emulsion or a water-in-oil emulsion.

In this regard it is noted that transdermal delivery technologies, e.g. iontophoresis, sonophoresis or microneedle-enhanced delivery, as described in Meidan V M and Michniak B B 2004 Am. J. Ther. 11(4): 312-316, can also be used for transdermal delivery of the CD4 binding muteins described here. Non-parenteral delivery modes are, for instance, oral, e.g. in the form of pills, tablets, capsules, solutions or suspensions, or rectal administration, e.g. in the form of suppositories. The muteins of the invention can be administered systemically or topically in formulations containing a variety of conventional non-toxic pharmaceutically acceptable excipients or carriers, additives, and vehicles.

The dosage of the mutein applied may vary within wide limits to achieve the desired preventive effect or therapeutic response. It will, for instance, depend on the affinity of the compound for CD4 as well as on the half-life of the complex between the mutein and CD4 in vivo. Further, the optimal dosage will depend on the biodistribution of the mutein or its fusion protein or its conjugate, the mode of administration, the severity of the disease/disorder being treated as well as the medical condition of the patient. For example, when used in an ointment for topical applications, a high concentration of the tear lipocalin mutein can be used. However, if wanted, the mutein may also be given in a sustained release formulation, for example liposomal dispersions or hydrogel-based polymer microspheres, like PolyActive or OctoDEX.

Alternatively, if administered systemically, the half-life of a lipocalin mutein can be extended, for example, by fusion to the Fc region of a preferably human immunoglobulin, to the CH4 domain of human IgE, or by conjugation to a polymer such as polyalkylene glycol (substituted or unsubstituted) or an activated derivative thereof, for example, polyethylene glycol (PEG) as described above.

Once a suitable route of administration has been found, the proper choice of a therapeutically effective dosage amount of the CD4 binding mutein of the invention for a given individual is within the level of skill in the art.

In general, a dose of about 0.05 mg to 50 mg of the unmodified tear lipocalin mutein per kilogram body weight administered systemically in an appropriate schedule may be suitable. Exemplary dosage levels may range from 0.5 mg to 5 mg per kg body weight for a long-term regimen and from 5 mg to 25 mg per kg body weight for short-term treatments. In case, the mutein is modified, for example by conjugation with a PEG molecule or by fusion with an albumin binding peptide, the dosage of 0.05 mg to 50 mg mutein is adjusted (increased) accordingly to still administer the same amount of CD4 binding mutein. The inventive compound/mutein can be applied as a single dose or may be divided into several, e.g. two to four, separate administrations. Alternatively, a CD4 binding mutein as described here can also be continuously infused over a certain period of time. In case of topical administration the concentration of the mutein may relate to the size of the area of the body onto which the pharmaceutical compositions (for example gel or cream) is applied.

Accordingly, the muteins of the present invention can be formulated into compositions using pharmaceutically acceptable ingredients as well as established methods of preparation (Gennaro, A. L. and Gennaro, A. R. (2000) *Remington: The Science and Practice of Pharmacy,* 20th Ed., Lippincott Williams & Wilkins, Philadelphia, Pa.). To prepare the pharmaceutical composition, pharmaceutically inert inorganic and/or organic excipients can be used. For example, to prepare pills, powders, gelatin capsules or suppositories, for example, lactose, talcum, stearic acid as well as its salts, fats, waxes, solid or liquid polyols, natural and hardened oils can be used. Suitable excipients for the production of solutions, suspensions, emulsions, aerosol mixtures or powders for reconstitution into solutions or aerosol mixtures prior to use include water, alcohols, glycerol, polyols, and suitable mixtures thereof as well as vegetable oils.

The pharmaceutical composition may also contain additives, such as fillers, binders, wetting agents, glidants, stabilizers, preservatives, emulsifiers, and, furthermore, solvents or solubilizers or agents for achieving a depot effect. As mentioned above, for achieving a depot effect a mutein of the invention may be incorporated into slow or sustained release or targeted delivery systems, such as liposomes and microcapsules.

The formulations can be sterilized by numerous means, including filtration through a bacteria-retaining filter, or by incorporating antiseptic agents in the form of sterile solid compositions which can be dissolved or dispersed in sterile water or other sterile medium just prior to use.

As mentioned above, the invention is also directed to the generation of a mutein of human tear lipocalin that bind CD4. The generation of CD4 binding muteins of the present invention can be carried out using any suitable technique that is known in the art for generating lipocalin muteins with antibody-like properties, i.e. that have affinity towards a given target. Examples of such combinatorial methods are described in detail in the international patent applications WO 99/16873, WO 00/75308, WO 03/029471, WO 03/029462, WO 03/029463, WO 2005/019254, WO 2005/019255 or WO 2005/019256, for instance.

As described in WO 2005/019255 or WO 2005/019256, the coding sequence of human tear lipocalin (Redl, B. et al. (1992) J. Biol. Chem. 267, 20282-20287) can serve as a starting point for mutagenesis of the four peptide segments selected in the present invention. For the mutagenesis of the amino acids in one or more of the four selected peptide loops, the various known methods for site-directed mutagenesis or for mutagenesis by means of the polymerase chain reaction as described in the above PCT applications are available to the person skilled in the art. The mutagenesis method can, for example, be characterized in that mixtures of synthetic oligodeoxynucleotides, which bear a degenerate base composition at the desired amino acid positions, can be used for introduction of the mutations. The use of nucleotide building blocks with reduced base pair specificity, as for example inosine, is also an option for the introduction of mutations into the chosen sequence segment or amino acid positions. The procedure for mutagenesis of target-binding sites is simplified as compared to antibodies (which is the classical scaffold used in combinatorial biotechnology for creating molecules with a desired binding specifity), since only four instead of six sequence segments—corresponding to the CDRs of an antibody—have to be manipulated for this purpose. A further possibility is the use of so-called triplet-mutagenesis. This method uses mixtures of different nucleotide triplets, each of which codes for one amino acid, for incorporation into the coding sequence (Virnekäs B, Ge L, Plückthun A, Schneider K C, Wellnhofer G, Moroney S E. 1994 Trinucleotide phosphoramidites: ideal reagents for the synthesis of mixed oligonucleotides for random mutagenesis. Nucleic Acids Res 22, 5600-5607).

One of the various applicable methods for the introduction of mutations into the region of the four exposed peptide loops of human tear lipocalin is based on the use of four oligodeoxynucleotides, each of which is partially derived from one of the four corresponding sequence segments to be mutated. In the preparation of these oligodeoxynucleotides, the person skilled in the art can employ mixtures of nucleic acid building blocks for the synthesis of those nucleotide triplets which correspond to the amino acid positions to be mutated, such that appropriate codons or anti-codons (depending on the sense or anti-sense direction of the oligodeoxynucleotide) randomly arise for all amino acids or, according to the genetic code and to the composition of this mixture, for a subset of the desired amino acids at this position. The naïve library which encodes the tear lipocalin muteins that carry mutations in the four chosen peptide segments can, for example, be obtained using the following approach.

A first oligodeoxynucleotide is prepared that corresponds in its sequence—apart from the mutated positions—at least partially to the coding strand for the first chosen peptide loop, which is located in the polypeptide sequence of tear lipocalin at the most N-terminal position (sequence positions 24-36). Accordingly, a second oligodeoxynucleotide corresponds at least partially to the non-coding strand for the second peptide loop, which follows in the polypeptide sequence (sequence positions 53-66). A third oligodeoxynucleotide corresponds in turn at least partially to the coding strand for the third peptide loop (sequence positions 79-84). Finally, a fourth oligodeoxynucleotide corresponds at least partially to the non-coding strand for the fourth peptide loop (sequence positions 103-110 or 102-110). A polymerase chain reaction can be performed with the respective first and second oligodeoxynucleotide and separately, if needed, with the respective third and fourth oligodeoxynucleotide by using the nucleic acid which encodes the scaffold protein and/or its complementary strand as a template.

The amplification products of both of these reactions can be combined by various known methods into a nucleic acid which comprises the sequence from the first to the fourth variegated sequence segment and which bears the mutations at the desired amino acid positions. To this end, both of the products can for example be subjected to a new polymerase chain reaction using flanking oligodeoxynucleotides as primers as well as one or more mediator nucleic acid molecule that contributes the sequence between the second and the third sequence segment. In the choice of the number of the oligodeoxynucleotides used for the mutagenesis and their arrangement within the coding sequence for the tear lipocalin or its mutein, the person skilled in the art has furthermore numerous alternatives at his disposal.

The nucleic acid molecules which code for the sequence region encompassing the four exposed peptide loops of tear lipocalin and which contain mutations at the chosen positions defined above can be connected by ligation with the missing 5'- and 3'-sequences of a nucleic acid coding for tear lipocalin and/or the cloning vector and used for transformation of a known host organism. A multitude of procedures are at one's disposal for the ligation and the cloning. For example, in the course of an amplification, synthetic nucleic acid molecules with restriction endonuclease recognition sequences, which are also present at the corresponding positions in the nucleic acid sequence for tear lipocalin can be attached at both ends of the nucleic acid to be cloned so that a ligation is made possible following hydrolysis with the corresponding restriction enzyme. As an alternative to ligation, the missing 5'- and 3'-sequences of a nucleic acid coding for tear lipocalin or its muteins can also be attached to the randomized nucleic acid molecule in another PCR.

Sequence segments within the gene coding for tear lipocalin can also be subjected to random mutagenesis via known methods, for example by use of the polymerase chain reaction under conditions of increased error rate, by chemical mutagenesis or by using bacterial mutator strains (Low et al., J. Mol. Biol. 260 (1996), 359-368). Such methods can also be used for the further optimization of the target affinity or target specificity of a CD4 binding mutein that has been initially identified. Mutations which possibly occur outside the segments of the sequence positions 24-36, 53-66, 79-84, and 103-110 of, for instance, can often be tolerated or can even prove advantageous, for example if they contribute to an improved folding efficiency or folding stability of the mutein.

After having brought to expression the coding nucleic acid sequences that were subjected to mutagenesis, the plurality of clones carrying the genetic information for the respective muteins with binding activity for CD4 can be selected from the library obtained. Known expression strategies and selection strategies can be employed for the selection of such clones. Methods of this kind have also been described in the context of the production or the engineering of recombinant antibody fragments, such as the "phage display" technique (Hoess, Curr. Opin. Struct. Biol. 3 (1993), 572-579; Wells and Lowman, Curr. Opin. Struct. Biol. 2 (1992), 597-604) or "colony screening" methods (Skerra et al., Anal. Biochem. 196 (1991), 151-155) or "ribosome display" (Roberts, Curr. Opin. Chem. Biol. 3 (1999) 268-273).

An embodiment of the "phage display" technique (Hoess, supra; Wells and Lowman, supra; Kay et al., Phage Display of Peptides and Proteins—A Laboratory Manual (1996), Academic Press) is given here as an example of a selection method according to the invention for muteins with the desired binding characteristics. The various other possible embodiments of the "phage display" technique are hereby incorporated into the disclosure by reference. For the exemplary selection method, phasmids are produced which effect the expression of the mutated tear lipocalin structural gene as a fusion protein with a signal sequence at the N-terminus, preferably the OmpA-signal sequence, and with the coat protein pIII of the phage M13 (Model and Russel, in "The Bacteriophages", Vol. 2 (1988), Plenum Press, New York, 375-456) or fragments of this coat protein, which are incorporated into the phage coat, at the C-terminus. The C-terminal fragment ΔpIII of the phage coat protein, which contains only amino acids 217 to 406 of the natural coat protein pIII, is preferably used to produce the fusion proteins. Especially preferred is a C-terminal fragment from pIII in which the Cys residue at position 201 is missing or is replaced by another amino acid.

The fusion protein can also contain other components, for example an affinity tag or an epitope sequence for an antibody which allows the immobilization or purification of the fusion protein or its parts. Furthermore, a stop codon can be located between the region coding for tear lipocalin or its mutein and the gene coding for the coat protein or its fragment, which stop codon, preferably an amber stop codon, is at least partially translated into an amino acid during translation in a suitable suppressor strain.

Phasmids here denote plasmids which carry the intergenetic region of a filamentous bacterial phage, such as M13 or f1 (Beck and Zink, Gene 16 (1981), 35-58), or a functional part thereof, so that during superinfection of the bacterial cells with a helper phage, for example M13K07, VCS-M13 or R408, one strand of the circular phasmid DNA is packaged with coat proteins and is exported into the medium as so-called phagemid. On the one hand this phagemid has the tear lipocalin mutein, which is encoded by the respective phasmid, built into its surface as a fusion with the coat protein pIII or its fragment, wherein the signal sequence of the fusion protein is normally cleaved off. On the other hand it carries one or more copies of the native coat protein pIII from the helper phage and is thus capable of infecting a recipient, generally a bacterial strain carrying an F- or F'-plasmid. In this way a physical coupling is ensured between the packaged nucleic acid carrying the genetic information for the respective tear lipocalin mutein and the encoded protein which is at least partially presented in a functional form on the surface of the phagemid.

For example, the phasmid vector pTLPC7 described in WO 2005/019256 or the phasmid vector pTPLC 27, now also called pTlc27, that is described here can be used for the preparation of a phagemid library encoding human tear lipocalin muteins. The inventive nucleic acid molecules coding for the tear lipocalin muteins are inserted into the vector using the two BstXI restriction sites. After ligation a suitable host strain such as E. coli XL1-Blue is transformed with the resulting nucleic acid mixture to yield a large number of independent clones.

The resulting library is subsequently superinfected in liquid culture with an appropriate M13-helper phage in order to produce functional phagemids. The recombinant phagemid displays the lipocalin mutein on its surface as a fusion with the coat protein pIII or a fragment thereof, while the N-terminal signal sequence of the fusion protein is normally cleaved off. On the other hand, it also bears one or more copies of the native capsid protein pIII supplied by the helper phage and is thus capable of infecting a recipient, in general a bacterial strain carrying an F- or F'-plasmid. During or after infection with helper phage, gene expression of the fusion protein between the lipocalin mutein and the capsid protein pIII can be induced, for example by addition of anhydrotetracycline. The induction conditions are chosen such that a substantial fraction of the phagemids obtained displays at least one lipocalin mutein on their surface. Various methods are known for isolating the phagemids, such as precipitation with polyethylene glycol. Isolation typically occurs after an incubation period of 6-8 hours.

The isolated phasmids can then be subjected to selection by incubation with the desired target, for example a recombinant extracellular fragment of CD4, wherein the target is presented in a form allowing at least temporary immobilization of those phagemids which carry muteins with the desired binding activity as fusion proteins in their coat. Among the various embodiments known to the person skilled in the art, the target can, for example, be conjugated with a carrier protein such as serum albumin and be bound via this carrier protein to a protein binding surface, for example polystyrene. Microtiter plates suitable for ELISA techniques or so-called "immunosticks" can preferably be used for such an immobilization of the target. Alternatively, conjugates of the target with other binding groups, such as biotin, can be used. The target can then be immobilized on a surface which selectively binds this group, for example microtiter plates or paramagnetic particles coated with streptavidin, neutravidin or avidin (cf. experimental section). If the target is fused to an Fc portion of an immunoglobulin, immobilization can also be achieved with surfaces, for example microtiter plates or paramagnetic particles, which are coated with protein A or protein G.

Non-specific phagemid-binding sites present on the surfaces can be saturated with blocking solutions as they are known for ELISA methods. The phagemids are then typically brought into contact with the target immobilized on the surface in the presence of a physiological buffer. Unbound phagemids are removed by multiple washings. The phagemid particles remaining on the surface are then eluted. For elution, several methods are possible. For example, the phagemids can be eluted by addition of proteases or in the presence of acids, bases, detergents or chaotropic salts or under moderately denaturing conditions. A preferred method is the elution using buffers of pH 2.2, wherein the eluate is subsequently neutralized. Alternatively, a solution of the free target can be added in order to compete with the immobilzed target for binding to the phagemids or target-specific phagemids can be eluted by competition with immunoglobulins or natural liganding proteins which specifically bind to the target of interest.

Afterwards, E. coli cells are infected with the eluted phagemids. Alternatively, the nucleic acids can be extracted from the eluted phagemids and used for sequence analysis, amplification or transformation of cells in another manner. Starting from the E. coli clones obtained in this way, fresh phagemids are again produced by superinfection with M13 helper phages according to the method described above and the phagemids amplified in this way are once again subjected to a selection on the immobilized target. Multiple selection cycles are often necessary in order to obtain the phagemids with the muteins of the invention in sufficiently enriched form. The number of selection cycles is preferably chosen such that in the subsequent functional analysis at least 0.1% of the clones studied produce muteins with detectable affinity for the given target. Depending on the size, i.e. the complexity of the library employed, 2 to 8 cycles are typically required to this end.

For the functional analysis of the selected muteins, an *E. coli* strain is infected with the phagemids obtained from the selection cycles and the corresponding double stranded phasmid DNA is isolated. Starting from this phasmid DNA, or also from the single-stranded DNA extracted from the phagemids, the nucleic acid sequences of the selected muteins of the invention can be determined by the methods known in the art and the amino acid sequence can be deduced therefrom. The mutated region or the sequence of the entire tear lipocalin mutein can be subcloned on another expression vector and expressed in a suitable host organism. For example, the vector pTLPC 9 described in WO 2005/019256 or the vector pTPLC 26 now also called pT1c26 can be used for expression in *E. coli* strains such as *E. coli* TG1. The muteins of tear lipocalin thus produced can be purified by various biochemical methods. The tear lipocalin muteins produced, for example with pTlc26, carry the affinity peptide STREP-TAG® II (Schmidt et al., supra) at their C-termini and can therefore preferably be purified by streptavidin affinity chromatography.

The selection can also be carried out by means of other methods. Many corresponding embodiments are known to the person skilled in the art or are described in the literature. Moreover, a combination of methods can be applied. For example, clones selected or at least enriched by "phage display" can additionally be subjected to "colony screening". This procedure has the advantage that individual clones can directly be isolated with respect to the production of a tear lipocalin mutein with detectable binding affinity for a target.

In addition to the use of *E. coli* as host organism in the "phage display" technique or the "colony screening" method, other bacterial strains, yeast or also insect cells or mammalian cells can be used for this purpose. Further to the selection of a tear lipocalin mutein from a random library as described above, similar methods can also be applied in order to optimize a mutein that already possesses some binding activity for the target with respect to affinity or specificity for the target after repeated, optionally limited mutagenesis of its coding nucleic acid sequence.

Once a mutein with affinity to CD4 has been selected, it is additionally possible to subject such a mutein to another mutagenesis in order to subsequently select variants of even higher affinity or variants with improved properties such as higher thermostability, thermodynamic stability, improved solubility, improved monomeric behavior, improved resistance against thermal denaturation, chemical denaturation, proteolysis, or detergents etc. This further mutagenesis, which in case of aiming at higher affinity can be considered as in vitro "affinity maturation", can be achieved by site specific mutation based on rational design or a random mutation. Another possible approach for obtaining a higher affinity or improved properties is the use of error-prone PCR, which results in point mutations over a selected range of sequence positions of the lipocalin mutein. The error-prone PCR can be carried out in accordance with any known protocol such as the one described by Zaccolo et al. (1996) J. Mol. Biol. 255, 589-603. Other methods of random mutagenesis that are suitable for such purposes include random insertion/deletion (RED) mutagenesis as described by Murakami, H et al. (2002) Nat. Biotechnol. 20, 76-81 or nonhomologous random recombination (NRR) as described by Bittker, J. A et al. (2002) Nat. Biotechnol. 20, 1024-1029. If desired, affinity maturation can also be carried out according to the procedure described in WO 00/75308 or Schlehuber, S. et al., (2000) J. Mol. Biol. 297, 1105-1120, where muteins of the bilin-binding protein having high affinity to digoxigenin were obtained.

EXEMPLARY EMBODIMENTS OF THE INVENTION

The ribbon diagram of FIG. 1 shows a relevant fragment of gp120 and the two N-terminal domains of CD4 (Kwong et al., supra). The X-ray structure of the complex between gp120 and CD4 shows that mainly residues in the D1 domain of CD4 are involved in the interaction with the viral envelope protein gp120.

As shown in FIG. 2 the expression vector pCD4-1 encodes a fusion protein comprised of the OmpA signal sequence (OmpA), human CD4-D12 and the STREP-TAG® II affinity tag. The expression cassette begins with the XbaI restriction site and ends with the HindIII restriction site. Gene expression is under the control of the tetracycline promoter/operator ($tet^{p/o}$). Transcription is terminated at the lipoprotein transcription terminator ($t_{lpp}$). The vector further comprises an origin of replication (ori), the intergenic region of the filamentous phage fl (fl-IG), the ampicillin resistance gene (bla) coding for β-lactamase and the tetracycline repressor gene (tetR). The vector elements outside the expression cassette are identical with those of the vector pASK75, the complete nucleotide sequence of which is exhibited in the German patent publication DE 44 17 598 A.

The vector pCD4-3, also schematically illustrated in FIG. 2, is identical with pCD4-1, except that the STREP-TAG® II is replaced by a $His_6$ tag.

The vector pTlc26 for the expression of wild type tear lipocalin as well as its muteins has the same composition as pCD4-1, except that the coding region for CD4-D12 is replaced by the one for human Tlc as detailed in FIG. 6.

The phasmid vector pTlc27 shown in FIG. 2 encodes a fusion protein comprising the OmpA signal sequence (OmpA), Tlc followed by the STREP-TAG® II, and a truncated form of the M13 coat protein pIII, comprising amino acids 217 to 406 (pIII). An amber stop codon, which is partially translated to Gln in SupE amber suppressor host strain, is located between the Tlc coding region, including the STREP-TAG® II, and the coding region for the truncated phage coat protein pIII to allow soluble expression of the Tlc mutein without the M13 coat protein pIII when employing a non-suppressor *E. coli* strain. Both the BstXI-restriction sites used for the cloning of the mutated gene cassette and the restriction sites flanking the structural gene are labeled. Gene expression is under the control of the tetracycline promoter/operator ($tet^{p/o}$). Transcription is terminated at the lipoprotein transcription terminator ($t_{lpp}$). The vector further comprises an origin of replication (ori), the intergenic region of the filamentous phage fl (fl-IG), the chloramphenicol resistance gene (cat) coding for chloramphenicol acetyl transferase and the tetracycline repressor gene (tetR).

The expression vector pTlc28 codes for a fusion protein of the OmpA signal sequence, Tlc, the STREP-TAG® II, and an albumin-binding domain (ABD) of protein G from *Streptococcus* (Kraulis et al. (1996) *FEBS Lett.* 378, 190-194). The expression cassette begins with an XbaI restriction site and ends with the HindIII restriction site. The vector elements outside this region are identical with those of the vector pASK75, the complete nucleotide sequence of which is exhibited in the German patent publication DE 44 17 598 A.

FIG. 3 shows a graphical representation of the data from Example 1, in which binding against gp120-MBP-His and, thus, functionality of the recombinant human CD4-D12- strepII (rhCD4strep; circles) was determined in an ELISA and compared with a mutant of CD4 carrying the amino acid substitutions Lys35Ala, Phe43Ala, and Arg59Ala (rhCD4m1; squares). High binding signals towards gp120 were obtained for hCD4-D12-strepII whereas no significant binding signals were detectable for rhCD4m1.

Figure 4:
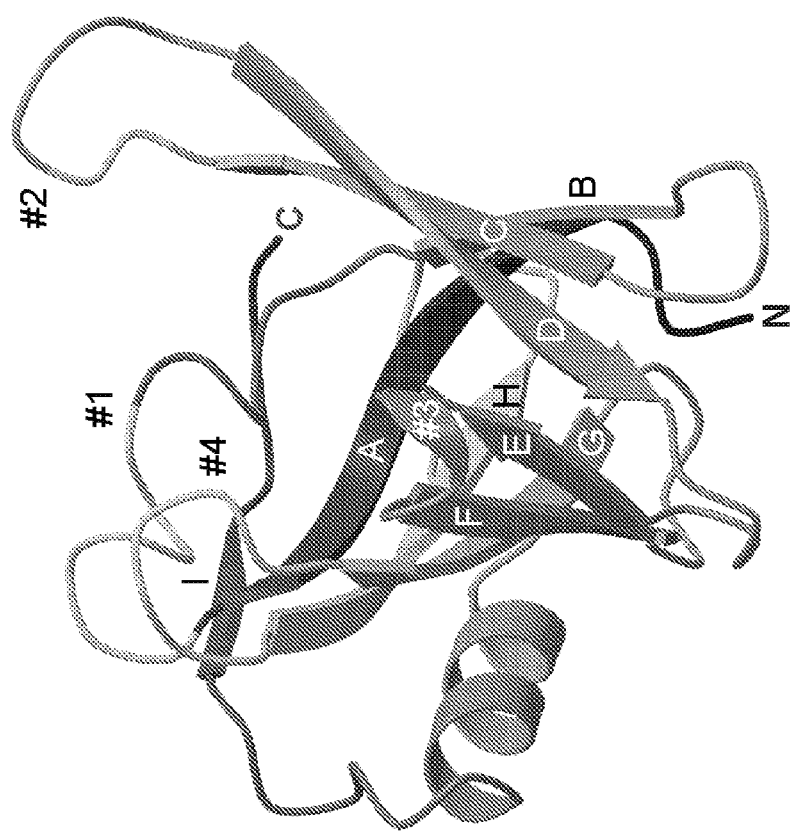

The ribbon diagram of FIG. 4 illustrates the position of the four exposed loops at the open end of the β-barrel in the three-dimensional structure of human tear lipocalin and was generated from the X-ray structural analysis as described (Breustedt, D. A., Korndörfer, I. P., Redl, B. & Skerra, A. (2005) The 1.8-Å crystal structure of human tear lipocalin reveals an extended branched cavity with capacity for multiple ligands. *J. Biol. Chem.* 280, 484-493).

Figure 5:
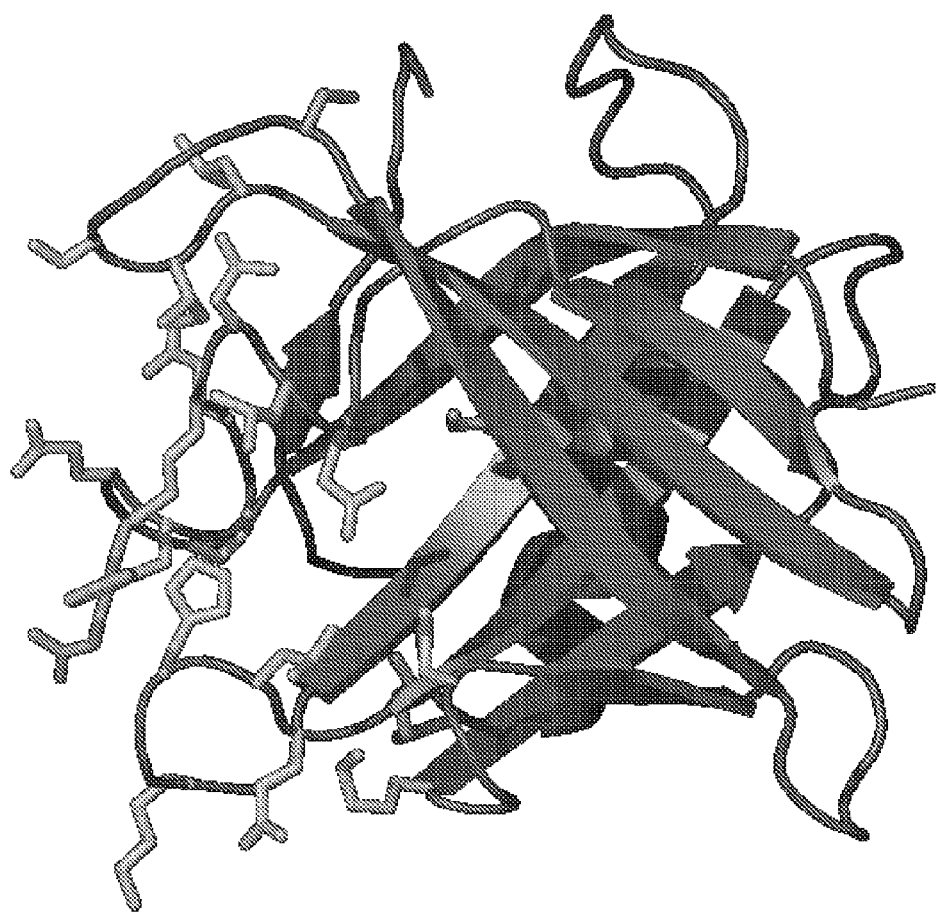

In this ribbon diagram of Tlc shown in FIG. 5, which is again based on the X-ray structure of Tlc, 18 amino acid positions chosen for mutagenesis according to Example 2, and illustrated on the gene level in FIG. 6, are depicted with their corresponding side chains.

FIG. 6 shows both the coding and the non-coding strand for the recombinant Tlc gene (SEQ ID NO: 64, corresponding to the expression cassette on pTlc26) together with the amino acid translation (SEQ ID NO: 65). PCR primers (AN-15F (SEQ ID NO: 26), AN-10 (SEQ ID NO: 27), AN-11 (SEQ ID NO: 28), AN-12 (SEQ ID NO: 29), AN-14 (SEQ ID NO: 30), AN-21 (SEQ ID NO: 31) and AN-22F (SEQ ID NO: 32)) are depicted either above (with their 5' end to the left) or below (with their 5' end to the right) the template double strand sequence. The sequence positions 26, 27, 28, 29, 30, 31, 32, 33, 34, 56, 57, 58, 80, 83, 104, 105, 106, and 108 were subjected to random mutagenesis in Example 2. The sequence positions 61, 111, 114, and 153 were modified for the ease of library construction (positions 111 and 114) or to remove the natural disulfide-bond (positions 61 and 153). The two BstXI restriction sites are underlined.

Figure 7:
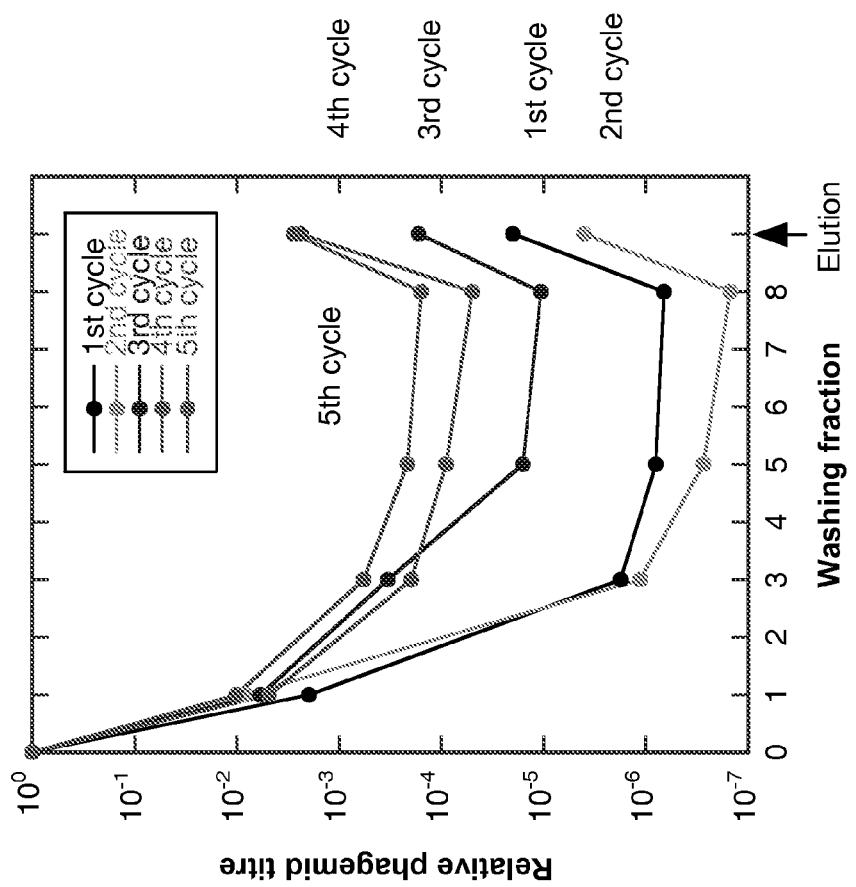
FIG. 7 shows the phagemid display selection from the tear lipocalin random library as carried out in Example 3.

The diagram of FIG. 7 shows a superposition of the elution profiles from enrichment cycles 1 to 5 during the selection of Tlc muteins from the Tlc library via phagemid display as described in Example 3. The relative fraction in each washing or elution fraction with respect to the totally applied titre of phagemids in each selection cycle is plotted against the number of washing steps.

Figure 8:
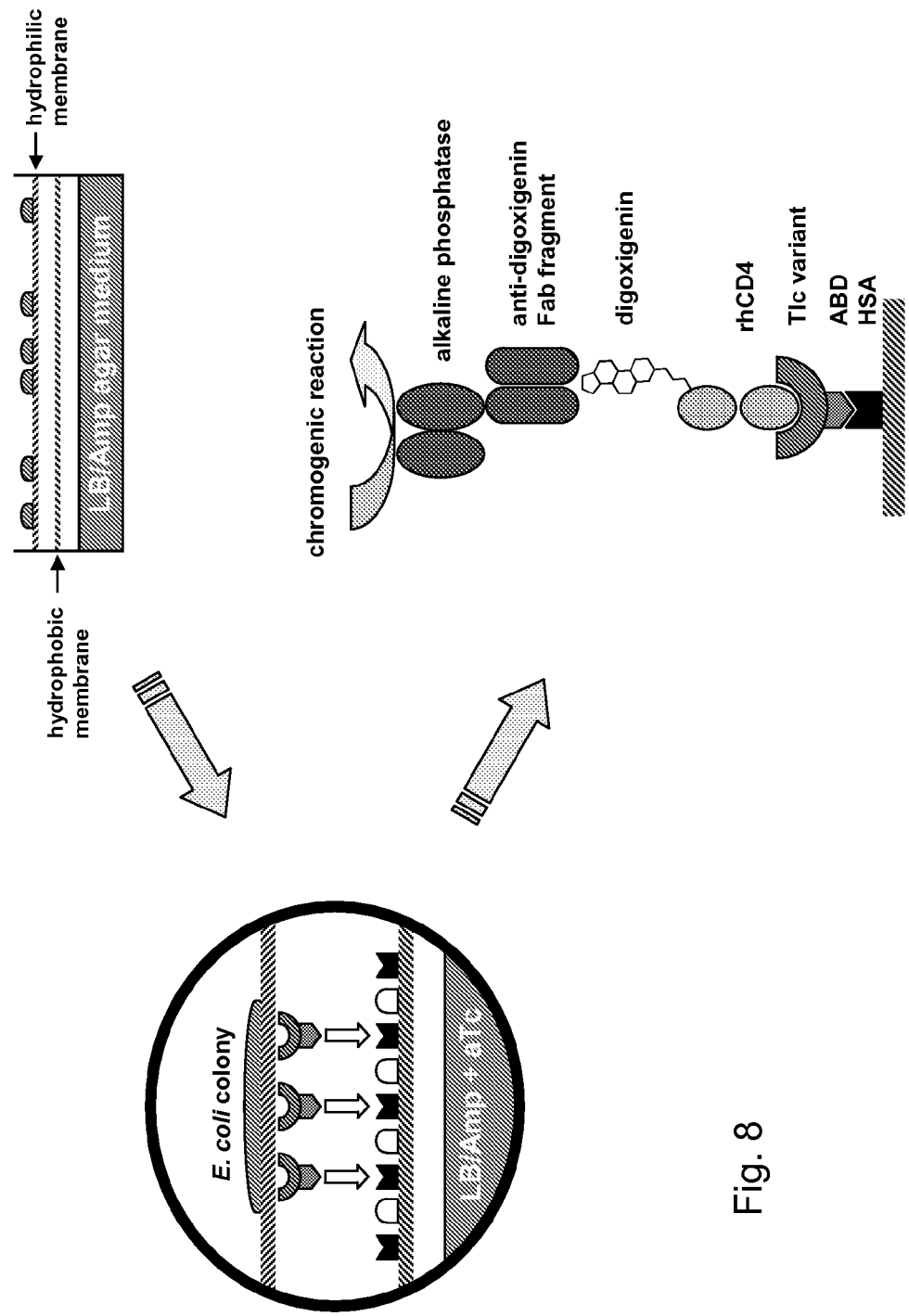
FIG. 8 shows the principle of the filter sandwich colony screening assay used in Example 4 to identify Tlc muteins with CD4-binding activity.

The general principle of the sandwich filter colony screening assay of FIG. 8 is explained in the literature (Skerra, A., Dreher, M. & Winter, G. (1991) Filter screening of antibody Fab fragments secreted from individual bacterial colonies: Specific detection of antigen binding with a two-membrane system. *Anal. Biochem.* 196, 151-155; Schmidt, T. G. M. & Skerra, A. (1993) The random peptide library-assisted engineering of a C-terminal affinity peptide, useful for the detection and purification of a functional Ig Fv fragment. *Protein Eng.* 6, 109-122; Schlehuber, S., Beste, G. & Skerra, A. (2000) A novel type of receptor protein, based on the lipocalin scaffold, with specificity for digoxigenin. *J. Mol. Biol.* 297, 1105-1120).

Figure 9:
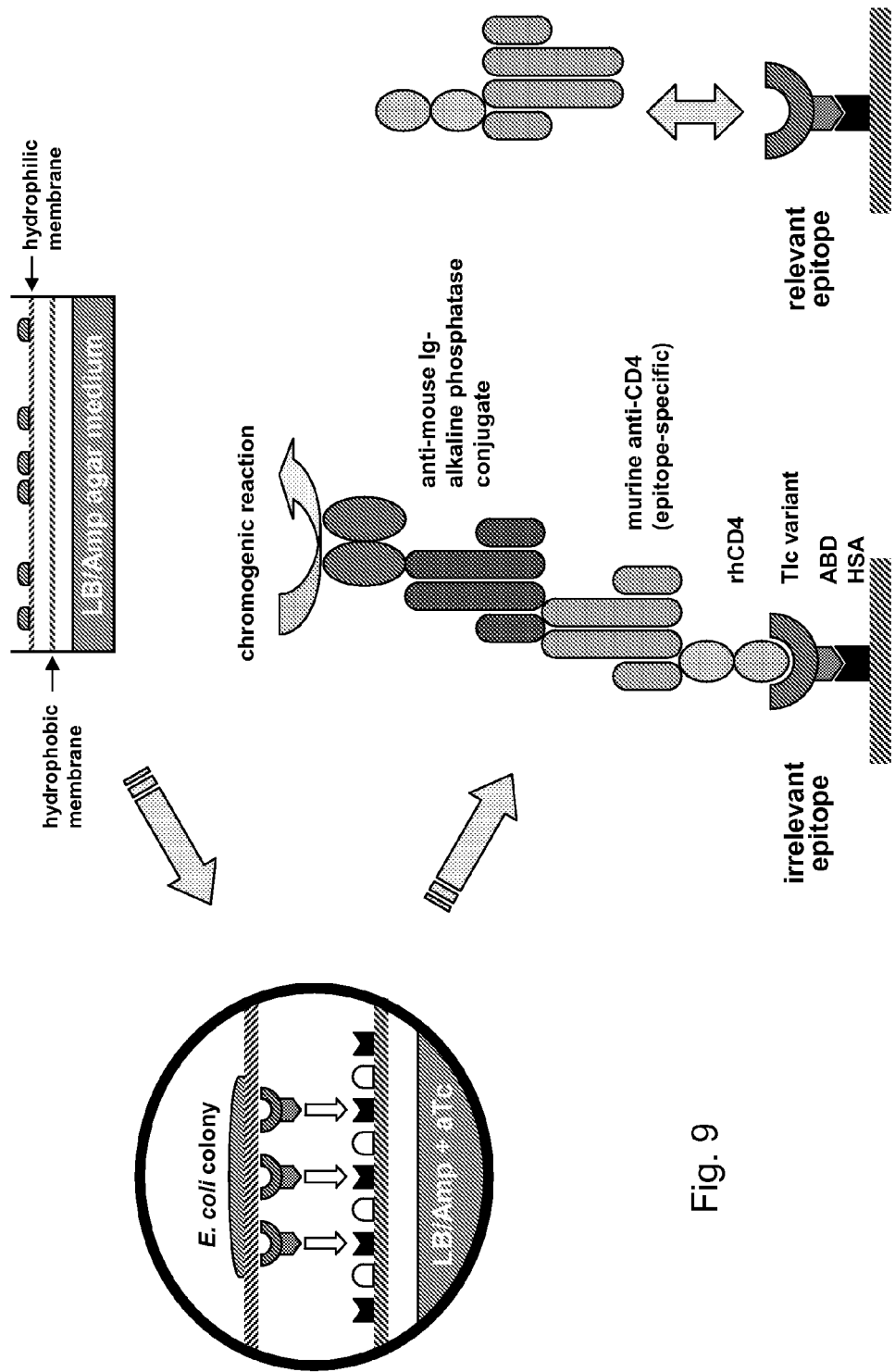
FIG. 9 shows the principle of the competitive filter sandwich colony screening assay used in Example 5 to identify Tlc muteins with epitope-specific (antagonistic) CD4 binding activity.

In the variation of the sandwich filter colony screening assay shown in FIG. 9 (cf. FIG. 8 for explanation) the competition between a CD4 epitope-specific antibody and Tlc muteins immobilized to the second filter membrane is used to identify muteins that recognize irrelevant epitopes on the CD4 target and to distinguish them from Tlc muteins with potential antagonistic binding activity.

FIG. 10 depicts the DNA sequences and corresponding amino acid for the selected Tlc muteins below the sequence of wtTlc. The sequences are shown for amino acid residues 18-125, encompassing the mutagenized part of the coding region, which is flanked by the BstXI restriction sites (CCAN$_6$TGG, underlined). Only the mutated nucleotides with respect to wtTlc and their encoded amino acids are given, whereas identical bases are represented by dots.

FIG. 11a shows SDS PAGE of Tlc muteins that were expressed from corresponding derivatives of pTlc26 and purified via the STREP-TAG® II, followed by size exclusion chromatography, as described in Example 6. Samples were analysed by 0.1% SDS 15% PAGE (Fling, S. P., and Gregerson, D. S. 1986. Peptide and protein molecular weight determination by electrophoresis using a high-molarity tris buffer system without urea. *Anal Biochem* 155: 83-88). Lanes: M, molecular size standard (as indicated in kDa units to the left); 1, wtTlc; 2, M25; 3, M23; 4, M23*; 5, M18; 6, M18*. A typical elution profile from size exclusion chromatography on a Superdex 75 HR 10/30 column for Tlc mutein M25 is shown in FIG. 11b.

The graphs of FIG. 12 depict the ELISA data from Example 7, which were performed according to Format A. All Tlc muteins bind hCD4-D 12-his6 in a concentration-dependent manner whereas no significant binding signals were detectable for wtTlc.

The graph of FIG. 13 depicts the ELISA data from Example 7, which were performed according to Format B.

The graph of FIG. 14 depicts the ELISA data from Example 7, which were performed according to Format C.

FIG. 15 shows the DNA sequences and corresponding amino acid translation from a selection experiment for improved Tlc muteins below the sequence of the mutein M23* and wtTlc. The sequences are shown for amino acid residues 18-125, encompassing the mutagenized part of the coding region, which is flanked by the BstXI restriction sites (CCAN$_6$TGG, underlined). Only the mutated nucleotides with respect to M23* and wtTlc and their encoded amino acids are given, whereas identical bases are represented by dots.

FIG. 16 shows the binding of M23* and improved Tlc muteins—applied at different concentrations—to PM1 cells expressing human CD4 in a flow cytofluorimetry assay. Bound lipocalin muteins were detected using an anti STREP-TAG® II antibody and a fluorescence-labeled secondary antibody. Panel A shows wild type Tlc (thick black line: 2000 nM, thick gray line: 1000 nM, broken line: 500 nM, dotted line: 250 nM, thin black line: 0 nM); panel B shows the mutein M23*(thick black line: 2000 nM, thick gray line: 1000 nM, broken line: 500 nM, dotted line: 250 nM, thin black line: 0 nM); panel C shows the mutein M23*.41 (thick black line: 500 nM, thick gray line: 250 nM, broken line: 125 nM, dotted line: 62.5 nM, thin black line: 0 nM); panel D shows the mutein M23*.49 (thick black line: 2000 nM, thick gray line: 1000 nM, broken line: 500 nM, dotted line: 250 nM, thin black line: 0 nM); panel E shows the mutein M23*.39 (thick black line: 1000 nM, thick gray line: 500 nM, broken line: 250 nM, dotted line: 125 nM, thin black line: 0 nM). wtTlc, mutein M23*, and improved Tlc muteins showed no binding to Raji cells (expressing no CD4, used as a control), thus indicating specific binding of all Tlc muteins.

EXAMPLES

Unless otherwise indicated, established methods of recombinant gene technology were used, for example, as described in Sambrook et al. (supra).

Example 1

Production and Characterization of the Recombinant Extracellular Region of Human CD4

As target for the selection of cognate Tlc muteins, the first two N-terminal domains, called D1 and D2 (Kwong et al., supra), were produced as a recombinant soluble protein via secretion into the periplasm of *E. coli*, where the disulfide bonds characteristic for this protein can readily form. Using a PCR-amplified human cDNA, two expression vectors were constructed: (i) pCD4-1 (FIG. 2) encoding hCD4-D12 equipped at its N-terminus with the OmpA signal sequence (which is cleaved off by signal peptidase after secretion across the inner bacterial membrane) and at its C-terminus with the STREP-TAG® II for simplified purification via streptavidin affinity chromatography; (ii) pCD4-3 (–) encoding hCD4-D12 equipped at its N-terminus again with the OmpA signal sequence and at its C-terminus with the His$_6$ tag for simplified purification via immobilized metal affinity chromatography (IMAC).

For the preparative production of hCD4-D12-strepII, *E. coli* K12 strain JM83 harbouring pCD4-1 was grown in a 2 L shake flask culture in LB-Ampicillin medium according to the protocol described in Schlehuber, S. et al. (*J. Mol. Biol.* (2000), 297, 1105-1120). When larger amounts of protein were needed, the *E. coli* K12 strain KS272 harbouring the expression vector pCD4-1 as well as the vector pTUM 4 (Breustedt, D. A., Schönfeld, D. L. and Skerra, A. (2006) *Biochim. Biophys. Acta* 1764, 161-173) was used for the periplasmatic production via bench top fermenter cultivation in an 8 l vessel based on the protocol described in Schiweck, W., and Skerra, A. *Proteins* (1995) 23, 561-565).

hCD4-D12-strepII was purified from the periplasmic fraction in a single step via streptavidin affinity chromatography using a column of appropriate bed volume according to the procedure described by Skerra, A. & Schmidt, T. G. M. (2000) (Use of the STREP-TAG® and streptavidin for detection and purification of recombinant proteins. *Methods Enzymol.* 326A, 271-304). hCD4-D12-his6 was produced from the vector pCD4-3 as described above and purified from the periplasmic fraction via IMAC following the procedure described by Skerra, A. (1994) (A general vector, pASK84, for cloning, bacterial production, and single-step purification of antibody F$_{ab}$ fragments. *Gene* 141, 79-84).

To achieve higher purity and to remove any aggregated recombinant protein, a gel filtration of hCD4-D12-strepII and of hCD4-D12-his6 was finally carried out on a Superdex 75 HR 10/30 column (24-ml bed volume, Amersham Pharmacia Biotech) in the presence of PBS buffer. The monomeric protein fractions were pooled, checked for purity by SDS-PAGE, and used for further biochemical characterization as well as target for the phage display selection. Protein concentration was determined via A$_{280}$ measurement using extinction coefficients $\epsilon_{280}$ of 24160 M$^{-1}$ for hCD4-D12-strepII and of 18470 M$^{-1}$ for hCD4-D12-his6.

The affinity of the hCD4-D12-strepII for CN54 gp120-MBP-His6 was measured in an ELISA. For this purpose, the wells of a 96 well microtiter plate (Falcon Micro Test III Flexible Assay Plates; 96 well) were coated with the gp120-MBP-His6 (20 μg/ml) for 2 h at RT. After washing three times with PBS/T, a dilution series of hCD4-D12-strepII in PBS/T was applied and incubated for 1 h at room temperature. In parallel, a dilution series of hCD4-D12ml-strepII, a mutant of CD4 carrying the amino acid substitutions Lys35Ala, Phe43Ala, and Arg59Ala in the gp120 binding site, was applied to another row of the same microtiter plate, which had also been coated with gp120-MBP-His. After washing three times with PBS/T, bound recombinant CD4 was detected by incubation with 50 μl Streptactin-alkaline phosphatase conjugate (IBA, 1:1000 in PBS/T) for 1 h. The wells were washed two times with PBS/T and PBS, and the signals were developed by addition of 100 μl of the chromogenic pNPP (AppliChem) at a concentration of 0.5 mg/ml in AP buffer (0.1 M Tris/HCl pH8.8, 0.1 M NaCl, 5 mM MgCl$_2$). The change in absorbance at 405 nm was measured in a SpectraMax 250 reader (Molecular Devices, Sunnyvale, Calif.).

The resulting data were subjected to curve fitting by nonlinear least squares regression with the help of the computer program Kaleidagraph (Synergy software) using the equation $[P \cdot L] = ([P]_t[L]_t)/(K_D+[P]_t)$. $[P]_t$ denotes the total concentration of immobilized target (in relative units), $[L]_t$ is the concentration of the applied CD4 protein, $[P \cdot L]$ is the concentration of the complex between CD4 and gp120 (measured as change in absorbance over time), and $K_D$ is the apparent dissociation constant. $[P]_t$ and $K_D$ were fitted as free parameters.

Figure 3:
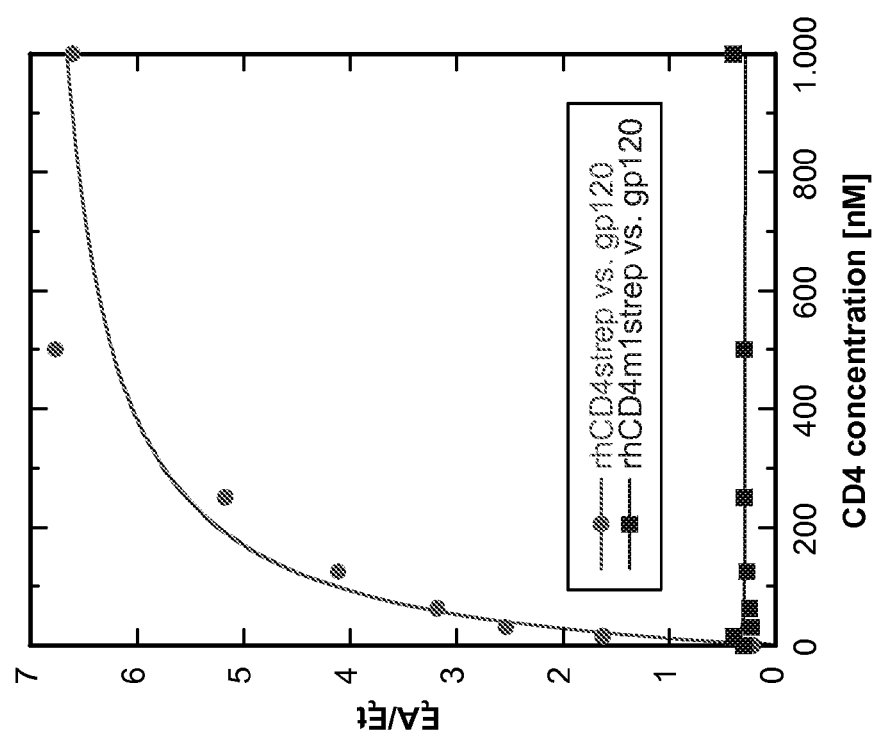

The resulting data and binding curves are depicted in FIG. 3. The value obtained for the apparent dissociation constants of the complex between hCD4-D12-strepII and gp120-MBP-His was 72±13 nM. No measurable binding activity was obtained for the control protein hCD4-D12m1-strepII.

Example 2

Generation of a Library with 2×10$^9$ Independent Tlc Muteins

A random library of TLPC with high complexity was prepared by concerted mutagenesis of the 18 selected amino acid positions 26, 27, 28, 29, 30, 31, 32, 33, 34, 56, 57, 58, 80, 83, 104, 105, 106, and 108 of the mature wild type human tear lipocalin. To this end, a gene cassette wherein the corresponding codons were randomized in a targeted fashion was assembled via polymerase chain reaction (PCR) with degenerate primer oligodeoxynucleotides in two steps according to a strategy describeded before (Skerra, A. (2001) "Anticalins": a new class of engineered-ligand-binding proteins with antibody-like properties. *J. Biotechnol.* 74, 257-275). In the first step a PCR fragment with randomized codons for the first and second exposed loop of Tlc was prepared using primers AN10 and AN11 while another PCR fragment with randomized codons for the third and fourth exposed loop of Tlc was prepared in parallel, using primers AN12 and AN21. In the second step these two PCR fragments were combined with a connecting oligodeoxynucleotide and used as templates in a PCR reaction with primers AN14 to yield the assembled randomized gene cassette.

The two PCR reactions (1a and 1b) for the first step were each performed in a volume of 50 μl using 9 ng pTlc26 plasmid DNA (FIG. 2) for each reaction as template, together with 25 pmol of each pair of primers (AN10 (SEQ ID NO: 27) and AN11 (SEQ ID NO: 28), or AN12 (SEQ ID NO: 29) and AN 21 (SEQ ID NO: 31), respectively), which were synthesized according to the conventional phosphoramidite method. In addition, the reaction mixture contained 5 μl×Taq reaction buffer (100 mM Tris/HCl pH 9.0, 500 mM KCl, 15 mM MgCl$_2$, 1% v/v Triton X-100) and 1 μl dNTP-Mix (10 mM dATP, dCTP, dGTP, dTTP). After bringing to volume with water, 2.5 u Taq DNA polymerase (5 u/μl, Promega) were added and 20 cycles of 1 minute at 94° C., 1 minute at 60° C. and 1.5 minutes at 72° C. were carried out in a programmable thermocycler with a heated lid (Eppendorf), followed by an incubation for 5 minutes at 60° C. for completion. The amplification products with the desired size of 135 bp and 133 bp, respectively, were isolated by preparative agarose gel electrophoresis using GTQ Agarose (Roth) and the Jetsorb DNA extraction kit (Genomed).

For the second PCR step a 1000 μl mixture was prepared, wherein approximately 500 fmol of both fragments from PCR reactions 1a and 1b were used as templates in the presence of 500 pmol of each of the flanking primers AN-15F and AN22-F and 10 pmol of the mediating primer AN-14. Both flanking primers carried a biotin group at their 5'-ends, thus allowing the separation of the PCR product after BstXI cleavage from incompletely digested product via streptavidin-coated paramagnetic beads. In addition, the reaction mix contained 100 µl 10× Taq buffer, 20 µl dNTP-Mix (10 mM dATP, dCTP, dGTP, dTTP), 50 u Taq DNA polymerase (5 u/µl, Promega) and water to bring the it to the final volume of 1000 µl. The mixture was divided into 100 µl aliquots and PCR was performed with 20 cycles of 1 minute at 94° C., 1 minute at 60° C., 1.5 minutes at 72° C., followed by a final incubation for 5 minutes at 60° C. The PCR product was purified using the E.Z.N.A. Cycle-Pure Kit (PeqLab).

For subsequent cloning, this fragment representing the central part of the library of Tlc muteins in nucleic acid form was first cut with the restriction enzyme BstXI (Promega) according to the instructions of the manufacturer and then purified by preparative agarose gel electrophoresis as described above, resulting in a double-stranded DNA-fragment of 303 base pairs in size.

DNA fragments not or incompletely digested were removed via their 5'-biotin tags using streptavidin-coated paramagnetic beads (Merck). To this end, 100 µl of the commercially available suspension of the streptavidin-coated paramagnetic particles (at a concentration of 10 mg/ml) was washed three times with 100 µl TE buffer (10 mM Tris/HCl pH 8.0, 1 mM EDTA). The particles were then drained with the help of a magnet and mixed with 50 pmol of the digested DNA fragment in 100 µl TE buffer for 15 minutes at room temperature. The paramagnetic particles were then collected at the wall of the Eppendorf vessel with the aid of a magnet and the supernatant containing the purified, fully digested DNA fragment was recovered for use in the following ligation reaction.

For the ligation reaction, 2.5 µg (12.5 pmol) of the PCR fragment and 39.5 µg (14 pmol) of the vector fragment (pTlc27) were incubated in the presence of 250 Weiss Units of T4 DNA ligase (Promega) in a total volume of 4300 µl (50 mM Tris/HCl pH 7.8, 10 mM MgCl$_2$, 10 mM DTT, 1 mM ATP, 50 µg/ml BSA) for 48 h at 16° C. The DNA in the ligation mixture was then precipitated 1.5 h by adding 106.8 µl yeast tRNA (10 mg/ml solution in H$_2$O (Roche)), 4300 µl 5 M ammonium acetate, and 17.1 ml ethanol. After precipitation, the DNA pellet was washed with 70% EtOH and then dried. At the end the DNA was dissolved to a final concentration of 200 µg/ml in a total volume of 400 µl of water.

The preparation of electrocompetent bacterial cells of *E. coli* strain XL1-Blue (Bullock et al., supra) was carried out according to the methods described by Tung and Chow (*Trends Genet.* 11 (1995), 128-129) and by Hengen (*Trends Biochem. Sci.* 21 (1996), 75-76). 1 l LB medium (10 g/L Bacto Tryptone, 5 g/L Bacto Yeast Extract, 5 g/L NaCl, pH 7.5) was adjusted to an optical density at 600 nm of OD$_{600}$=0.08 by addition of an overnight culture of XL1-Blue and was incubated at 140 rpm and 26° C. in a 2 l Erlenmeyer flask. After reaching an OD$_{600}$=0.6, the culture was cooled for 30 minutes on ice and subsequently centrifuged for 15 minutes at 4000 g and 4° C. The cells were washed twice with 500 ml ice-cold 10% w/v glycerol and finally re-suspended in 2 ml of ice-cold GYT-medium (10% w/v glycerol, 0.125% w/v yeast extract, 0.25% w/v tryptone). The cells were then aliquoted (200 µl), shock-frozen in liquid nitrogen and stored at −80° C.

Electroporation was performed with a Micro Pulser system (BioRad) in conjunction with cuvettes from the same vendor (electrode distance 2 mm) at 4° C. Aliquots of 10 µl of the ligated DNA solution (containing 1 µg DNA) was mixed with 100 µl of the cell suspension, first incubated for 1 minute on ice, and then transferred to the pre-chilled cuvette. Electroporation was performed using parameters of 5 ms and 12.5 kV/cm field strength and the suspension was immediately afterwards diluted in 2 ml ice-cold SOC medium (20 g/L Bacto Tryptone, 5 g/L Bacto Yeast Extract, 10 mM NaCl, 2.5 mM KCl, pH 7.5, autoclaved, before electroporation 10 ml/L 1 M MgCl$_2$ and 1 M MgSO$_4$ with 20 ml/L 20% Glucose were added), followed by incubation for 60 minutes at 37° C. and 140 rpm. After that, the culture was diluted in 2 L 2×YT medium (16 g/L Bacto Tryptone, 10 g/L Bacto Yeast Extract, 5 g/L NaCl, pH 7.5) containing 100 µg/ml chloramphenicol (2 YT/Cam), resulting in an OD$_{550}$ of 0.26. The culture was incubated at 37° C. until the OD$_{550}$ had risen again by 0.6 units.

By employing a total of 40 µg ligated DNA in 40 electroporation runs, a total of about $2.0 \times 10^9$ transformants were obtained. The transformants were further used for the preparation of phagemids coding for the library of the Tlc muteins as fusion proteins.

For preparation of the phagemid library, 400 ml of the culture from above were infected with $1.3 \times 10^{12}$ pfu VCS-M13 helper phage (Stratagene). After agitation at 37° C. for 30 min Kanamycine was added at a concentration of 70 mg/l and the incubation temperature was lowered to 26° C. After 10 min of temperature equilibration 25 µg/l anhydrotetracycline was added in order to induce gene expression for the fusion protein between the Tlc muteins and the phage coat protein. Phagemid production was allowed for 7 h at 26° C. After removal of the bacteria by centrifugation the phagemids were precipitated from the culture supernatant twice with 20% (w/v) polyethylene glycol 8000 (Fluka), 15% (w/v) NaCl and finally dissolved in PBS (4 mM KH$_2$PO$_4$, 16 mM Na$_2$HPO$_4$, 115 mM NaCl).

Example 3

Phagemid Selection of Tlc Muteins Against a Recombinant Extracellular Fragment of CD4

For selection of CD4-specific Tlc muteins, $4 \times 10^{11}$ phagemids of the library obtained from Example 2 were used. First, the freshly prepared phagemids (260 µl) were blocked with 100 µl 8% w/v bovine serum albumin (BSA; Roth) in 0.4% PBS/T for 1 h at RT and then mixed with 40 µl of 1 µM biotinylated CD4-D12-strepII from Example 1 (final conc. 100 nM). After 1 h incubation the phagemid solution was added to the pre-blocked (2% w/v bovine serum albumin and PBS containing 0.1% Tween 20) and drained streptavidin-coated paramagnetic particles (M-280 Streptavidin, Roth) and incubated for 10 min. Free binding sites on the streptavidin beads were saturated by adding 10 µl 4 mM D-Desthiobiotin (IBA) in PBS. Following 5 min incubation, uncomplexed phagemids were removed by washing of the beads—via resuspending them and collecting them with the help of a magnet—eight times with each 1 ml of PBS/T. Bound phagemids were eluted with 400 µl of 0.1 M glycine/HCl, pH 2.2 for 13 min, followed by immediate neutralization with 60 µl of 0.5 M Tris base. The eluted phagemid solution (440 µl) was used to infect 4 ml culture of *E. coli* XL1-Blue for the reamplification. Then the culture was incubated at 37° C. for 30 min under agitation. After centrifugation at 4000 rpm for 5 min, the culture was resuspended in 600 µl 2×YT mediun and plated on three big agar plates (LB/Cam, 13.5 cm). LB/Cam agar (10 g/L Bacto Tryptone, 5 g/L Bacto Yeast Extract, 5 g/L NaCl, pH 7.5, 15 g/L Bacto agar; 1:1000 chloramphenicol)

plates were incubated at 22° C. overnight. The infected cells were scraped over the agar plates using 50 ml 2×YT medium. This homogenized cell suspension was used to inoculate three times 50 ml 2×YT medium by a dilution of 1:1000. The cultures was incubated at 37° C. till the $OD_{550}$ 0.5 and then infected with the helper phages according to the protocol described in Example 2. The other two 50 ml cultures were further incubated for 7 h for the phasmid DNA isolation according to the instructions of the manufacturer employing the midiprep kit (Qiagen Midi Kit). After each cycle of selection, the titers of the phagemid input, the first, third, fifth and eighth washing fractions, and the eluted phagemids, were determined. In brief, 20 µl serial dilutions of the phagemid solution were mixed with 180 µl culture of *E. coli* XL1-Blue and incubated for 30 min at 37° C. Aliquots of the infected cells (100 µl) were plated on LB/Cam agar plates and incubated over night at 37° C. On the next day, the colonies were counted and the titers of the phagemid solutions (cfu/ml) were determined.

Another four selection cycles against CD4-D12-strep II were carried out in this way by employing the preparation of amplified phasmids from the respective previous enrichment cycle.

Example 4

Identification of CD4-specific Tlc Muteins by Colony Screening

The mutagenized central cassette of the Tlc gene was isolated from the pTlc27 phasmid preparation obtained after phage display selection against the recombinant CD4 target as described in Example 3 by cutting with BstXI, followed by purification via agarose gel electrophresis. The DNA fragment was inserted into the likewise cut vector pTlc28 (FIG. 2) which encodes a fusion protein between Tlc and a bacterial albumin-binding domain, ABD (König and Skerra, 1998, *J. Immunol. Methods*, 218, 73-83). $CaCl_2$-competent TG1/F' cells were transformed with the ligation mixture and, for subsequent filter sandwich colony screening assay (Schlehuber, S., Beste, G. & Skerra, A. (2000) A novel type of receptor protein, based on the lipocalin scaffold, with specificity for digoxigenin. *J. Mol. Biol.* 297, 1105-1120), plated on a hydrophilic membrane (GVWP, 0.22 µm, Millipore) on top of the petri dish with LB/Amp agar and incubated for 8-9 h at 37° C. In the meantime a hydrophobic membrane (Immobilon-P, 0.45 µm, Millipore) was coated with 10 mg/ml human serum albumin (HSA, Sigma) in PBS for 4 h and blocked for 2 h in PBS containing 3% w/v BSA and 0.5% v/v Tween 20. After washing twice with PBS and soaking in LB/Amp containing 200 µg/l aTc, this membrane was placed on an agar plate with LB/Amp containing 200 µg/l aTc, covered with the first membrane, supporting the colonies, and finally incubated for 12 h at 22° C. During this period the Tlc muteins fused with the ABD were released from the colonies and immobilized on the lower membrane via complex formation between HSA and ABD. The first membrane with the still viable colonies was transferred to a fresh LB/Amp agar plate and stored at 4° C.

The hydrophobic membrane was washed three times with PBS/T and incubated with a 100 nM solution of hCD4-D12-strepII, labeled with digoxigenin groups according to the protocol by Schlehuber et al., supra, for 1 h. After another three washing steps with PBS/T the membrane was incubated with an anti-digoxigenin Fab fragment conjugated with alkaline phosphatase (Roche Diagnostics) for 1 h in order to detect CD4 target protein that was bound by some of the Tlc muteins immobilized on the membrane. The membrane was washed again twice with PBS/T and twice with PBS. The signals were developed in the presence of AP buffer (100 mM Tris/HCl pH 8.8, 100 mM NaCl, 5 mM $MgCl_2$) containing 30 µl BCIP (50 mg/ml 5-bromo-4-chloro-3-indolyl phosphate, 4-toluidine salt in DMF) and 5 µl NBT (75 mg/ml nitro blue tetrazolium in 70% v/v DMF). The colonies that gave rise to the most intense signals were identified on the first membrane and propagated for further analysis.

Example 5

Identification of Epitope-specific Tlc Muteins by means of a Competitive Colony Screening Method For the competitive colony screening assay a filter carrying the Tlc muteins immobilized as ABD fusion proteins was prepared using the sandwich technique as described in Example 4. In this case colonies that had already been identified to encode CD4-specific Tlc muteins by the assay described in Example 4 were spotted in duplicate on the first membrane by using a toothpick.

First an assay was performed to assess the specificity of target recognition. To this end two different filter sandwich membranes were prepared on which preselected colonies had been parallelly spotted in defined positions (to allow later assignment of the signals). One of the resulting membranes was incubated with 100 nM digoxigenated hCD4-D12-strepII whereas the other membrane was incubated with digoxigenated ovalbumin (serving as a dummy target) and development and staining was performed as decribed in Example 4.

Colonies which gave rise to signals after incubation with the hCD4-D12-strepII but not with ovalbumin were further analysed for epitope specificity in a following filter sandwich assay, again using two membranes in parallel. In one case the second membrane was incubated with 3 µg/ml D2-specific monoclonal anti-CD4 antibody (specific for the domain 2 of human CD4, clone no. M-T441, Ancell) in the presence of 100 nM unlabelled hCD4-D12-strepII, whereas in the other case the second membrane was incubated with 3 µg/ml D1-specific anti-CD4 antibody (binds the D1 domain of human CD4 and is capable of blocking HIV-1 gp120, purified mouse anti-human monoclonal antibody, clone no. RPA-T4, BD Pharmingen) with 100 nM unlabelled hCD4-D12-strepII for 1 h.

After three times washing with PBS/T, these two membranes were incubated with anti-mouse IgG (Fc specific) conjugated with alkaline phosphatase (1:1000, Sigma) in order to detect bound anti-CD4 antibodies. The filters were washed again twice with PBS/T and twice with PBSand the signals were developed in the presence of AP buffer containing 30 Zµl BCIP and 5 µl NBT. As result signals were obtained in the first case for Tlc muteins which were capable to bind to the D1 domain of the CD4 target such that the D2-specific antibody could bind to the corresponding complex at the same time. In the second case signals were obtained for Tlc muteins which were capable to bind to the D2 domain of the CD4 target such that the D1-specific antibody could bind to the corresponding complex at the same time.

Colonies giving positive signals in these two assays were selected for sequence analysis (FIG. 10) by using the oligodeoxynucleotide F-83 as a primer on an automated Genetic Analyzer ABI-Prism A310 system (Applied Biosystems) employing the Big Dye Terminator Cycle Sequencing Kit (Applied Biosystems).

Example 6

Bacterial Production of CD4-Specific Tlc Muteins

Figure 1:
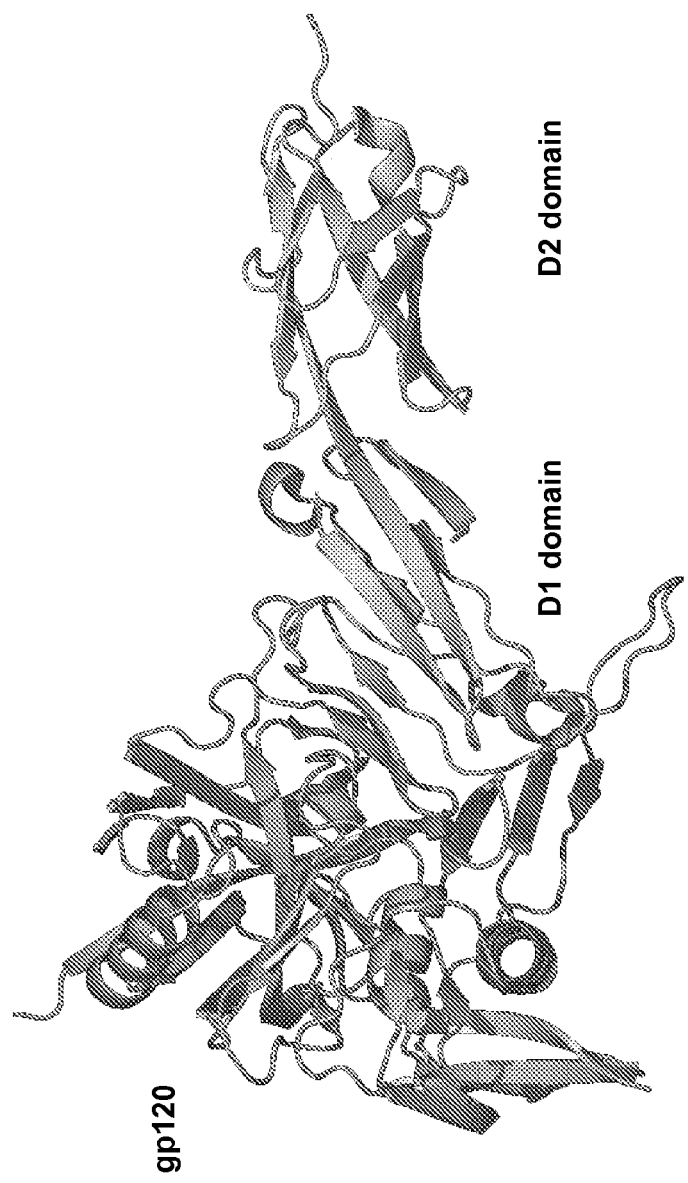
Figure 2:
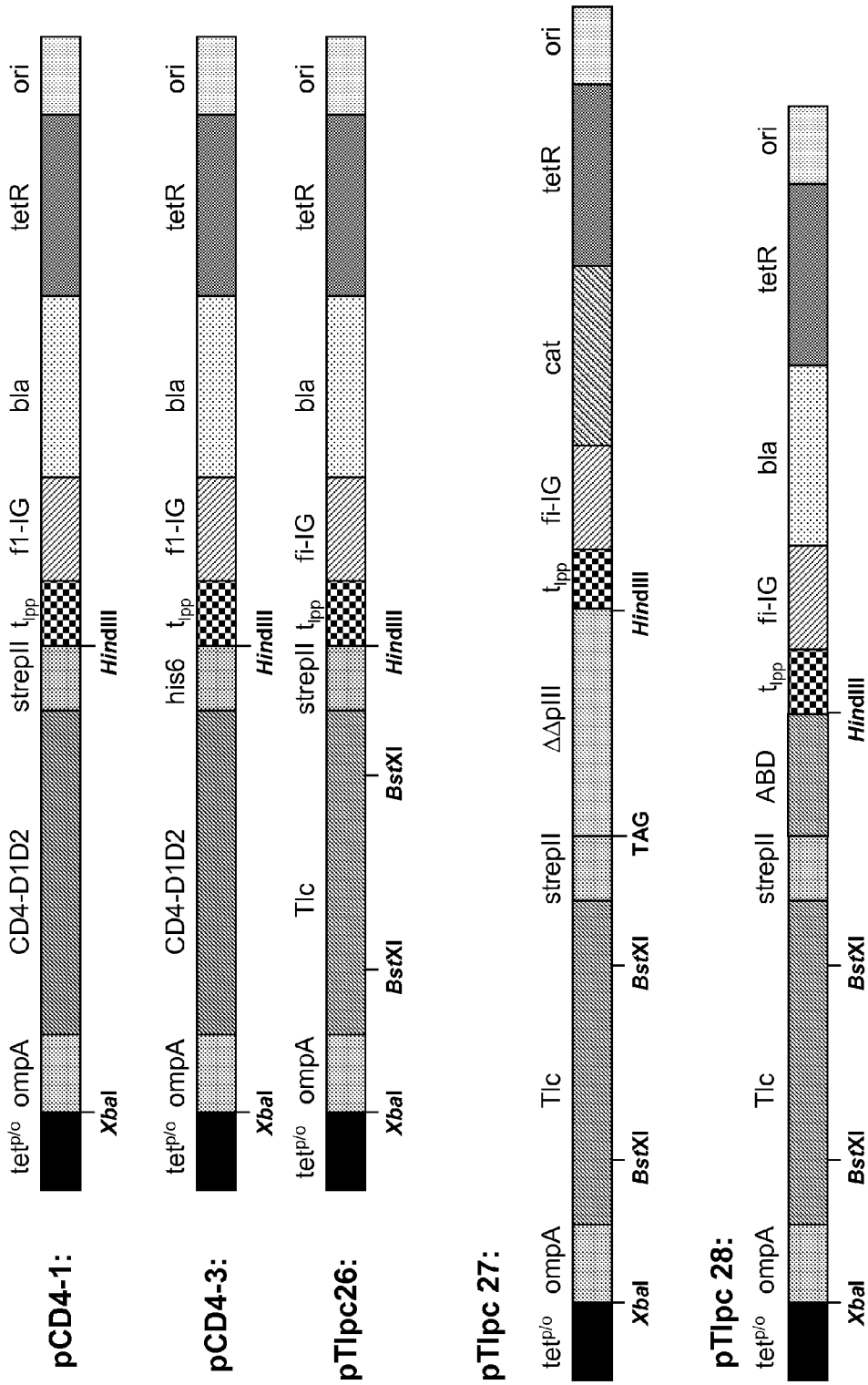

For soluble protein production, the central mutagenized coding regions for the Tlc muteins obtained from Example 5 were subcloned via the two BstXI restriction sites from the corresponding vector pTlc28 (FIG. 2) on the expression plasmid pTlc26 (FIG. 2). The resulting plasmid encodes the Tlc mutein with the OmpA signal sequence at its N-terminus and the STREP-TAG® II at the C-terminus.

The Tlc muteins M18 (AN-ksf 2-GTG AAC CTC TTG GAA TTC TTC GGG TCC ACC GTC) (SEQ ID NO: 33) and M23 (AN ksf 1-GAC CGG CCC CCG GAC AAC ATG GTG A) (SEQ ID NO: 34) each contained one Cys residue in their sequences at positions 29 and 57, respectively (FIG. 10). In order to avoid formation of protein dimers via disulfide bridges the Cys residue was replaced in both cases by a Ser residue according to the protocol described in Kunkel, T A. et al. (*Methods in Enzymology*, (1990), 204, 125-139) using appropriate deoxynucleotide primers. The resulting mutants were termed M18* (i.e. M18(Cys29Ser)) and M23* (i.e. M23 (Cys57Ser)), respectively.

*E. coli* JM83 transformed with the corresponding pTlc28 plasmid derivative coding for a Tlc mutein was used for shaker flask expression. Bacterial culture, induction of gene expression, cell harvest, periplasmic extraction as well as purification via streptavidin affinity chromatography the size exclusion chromatography (gel filtration) was performed as described for the extracellular region of CD4 in Example 1. It was found that some of the Tlc muteins eluted from the gel filtration in up to three distinct peaks, containing aggregated, dimeric, and monomeric protein respectively. In each case, only the monomeric protein fraction was used for subsequent functional analysis. Protein concentration was measured via absorption at 280 nm using an average extinction coefficient of 23470 $M^{-1}$.

Example 7

Measurement of Binding Activity Towards Recombinant CD4 for the Tlc Muteins in an ELISA The purified Tlc muteins obtained from Example 6 were tested in an ELISA for binding to the recombinant target proteins hCD4-D 12-strepII or hCD4-D 12-his6, whereby ovalbumin served as a negative control protein. Several different experimental formats were used:

Format A:
The wells of an ELISA plate (Falcon Micro Test III Flexible Assay Plates; 96 well) were coated with 50 µl of hCD4-D12-his6 (0.5 µM) or ovalbumin (0.5 µM, Sigma) for 2 h at RT. The wells were washed three times, blocked with 3% w/v BSA in PBS/T for 1 h and washed again three times with PBS/T. The Tlc muteins were applied in a dilution series in PBS/T, covering an appropriate concentration range, and incubated for 1 h at RT. After washing, bound muteins were detected by incubation with Streptactin-alkaline phosphatase conjugate (IBA) and subsequent chromogenic reaction and the resulting data were subjected to curve fitting as described in Example 1. Specific binding activity for the recombinant CD4 target was detected for all muteins listed in FIG. 10. No measurable binding activity was obtained for the control protein. Some exemplary binding curves of the lipocalin muteins M23*, M25, M48, M23.11 and M23.31B are depicted in FIG. 12a and FIG. 12b and the calculated $K_D$ values are listed in Table 1.

TABLE 1

Affinities between tear lipocalin muteins and recombinant CD4 (expressed as dissociation constants, $K_D$)

| Tear lipocalin mutein | $K_D$ [nM] hCD4-D12-his6 |
|---|---|
| M18(Cys29Ser) | 3.8 ± 0.6 |
| M23(Cys57Ser) | 148.6 ± 11.1 |
| M25 | 1559 ± 709 |
| M48 | 452 ± 0.07 |
| M23.11A | 724 ± 111 |
| M23.31B | 43.2 ± 2.2 |

Format B:
For competitive ELISA the wells of a microtiter plate (Falcon; as above) were coated with 50 µl of hCD4-D12-strepII (0.5 µM). After washing and blocking as described above, the wells were then incubated with Tlc muteins in PBS/T, in a dilution series covering an appropriate concentration range, in the presence of a D1-specific anti-CD4 antibody, which is capable of blocking gp120, at constant concentration (5 µg/ml; Catalog #24227-0.5, Polysciences). Bound anti-CD4 antibody was detected via anti-mouse IgG, Fc specific, conjugated with alkaline phosphatase (1:1000, Sigma), followed by chromogenic reaction as described in Example 1. The results of an ELISA for the Tlc muteins, M23*, M23.11A, and M23.31B as well as wtTlc are shown in FIG. 13. The data indicate that, while wild type Tlc shows almost no competition, the Tlc muteins M23*, M23.11A, and M23.31B prevent the anti-CD4 antibody from binding to the target in a concentration-dependent manner, thus indicating that they recognize the relevant epitope in the D1 domain.

Format C:
In an alternative procedure, the ELISA plate was coated with the recombinant CD4 target via capturing with an antibody specific for the D2 domain of CD4. To this end, the wells of a microtiter plate (as above) were first incubated with a D2-specific anti-CD4 antibody (5 µg/ml; Clone no. M-T441, Ancell) for 2 h and then blocked with BSA and washed with PBS/T as described above. Then, the wells were incubated with hCD4-D12-his6 (1 µM) for 1 h. After washing, the wells were incubated with Tlc muteins in PBS/T, at a constant concentration of 0.5 µM, in the presence of a dilution series of CN54 gp120-MBP-His6, covering an appropriate concentration range. The bound muteins were subsequently detected via Streptactin-alkaline phosphatase conjugate (1:1000, IBA Göttingen, Germany), followed by chromogenic reaction as described in Example 1. The resulting data (FIG. 14) show that, while wild type Tlc does not even bind to the recombinant CD4, the gp120 competes with the Tlc muteins M23* and M23.11A for binding to the CD4 target, thus indicating an antagonistic mode of action for these Tlc muteins.

TABLE 2

Sequence characteristics of selected Tlc muteins

| Pos. | Tlc | M18(29Cys/Ser) | M23 | M23* |
|---|---|---|---|---|
| 26 | Arg | Pro | Asn | Asn |
| 27 | Glu | Lys | Ser | Ser |
| 28 | Phe | Asn | Lys | Lys |
| 29 | Pro | Cys(Ser) | Lys | Lys |
| 30 | Glu | Lys | Tyr | Tyr |

TABLE 2-continued

Sequence characteristics of selected Tlc muteins

| Pos. | Tlc | M18(29Cys/Ser) | M23 | M23* |
|---|---|---|---|---|
| 31 | Met | Arg | Asn | Asn |
| 32 | Asn | Phe | Arg | Arg |
| 33 | Leu | Thr | Arg | Arg |
| 34 | Glu | Ser | His | His |
| 38 | Pro | Pro | Ala | Ala |
| 56 | Leu | Ser | Leu | Leu |
| 57 | Ile | Tyr | Cys | Ser |
| 58 | Ser | Lys | Gly | Gly |
| 80 | Asp | Ile | Leu | Leu |
| 83 | Lys | Glu | Asp | Asp |
| 102 | Glu | Lys | Lys | Lys |
| 104 | Glu | Trp | Trp | Trp |
| 105 | Leu | Leu | Leu | Leu |
| 106 | His | Arg | Gly | Gly |
| 108 | Lys | Leu | Phe | Phe |

Example 8

Generation of an Error-Prone PCR Library for the CD4-Specific Tlc Mutein M23* and Affinity Maturation The CD4-specific Tlc mutein M23* (M23(Cys57Ser)) described in Example 6 was subjected to an in vitro affinity maturation. To this end, a second generation library was prepared, based on the coding nucleic acid for the Tlc mutein M23*, by employing an error-prone PCR protocol that makes use of the deoxynucleotide analogs 8-oxodGTP and dPTP (both from TEBU-Bio) according to a method described (Zaccolo et al. (1996) *J. Mol. Biol.* 255,589-603). For the error-prone amplification reaction the 5'-biotinylated oligodeoxynucleotides AN-15F (SEQ ID NO: 26) and AN-22F (SEQ ID NO: 32) were used as primers. Since these oligodeoxynucleotides flank the two BstXI restriction sites which encompass the central gene cassette including the coding region for the four exposed loops of Tlc (FIG. 6), the PCR results in point mutations randomly distributed over this part of the Tlc mutein.

The PCR reaction was performed in a volume of 500 μl with 10 ng pTlc26-M23* plasmid DNA (FIG. 2) as template, 2.5 μl-oxo-dGTP (1mM), 2.5 μl dPTP (1mM)), together with each 10 pmol of primers AN-15F and AN-22F. In addition, the reaction mixture contained 50 μl 10× Taq reaction buffer (100 mM Tris/HCl pH 9.0, 500 mM KCl, 15 mM $MgCl_2$, 1% v/v Triton X-100) and 10 μl dNTP-Mix (10 mM dATP, dCTP, dGTP, dTTP). After bringing to volume with water, 15 u Taq DNA polymerase (5 u/μl, Promega) were added and 20 cycles of 1 minute at 94° C., 1 minute at 60° C. and 1.5 minutes at 72° C. were carried out in a programmable thermocycler with a heated lid (Eppendorf), followed by an incubation for 5 minutes at 60° C. for completion. The PCR product was purified using the E.Z.N.A. Cycle-Pure Kit (PeqLab), cut with the restriction enzyme BstXI (Promega), purified, and subcloned on the vector pTlc27 (FIG. 2) as described in Example 2.

For the ligation reaction, 5 μg (25 pmol) of the purified PCR fragment and 68 μg (23 pmol) of the BstXI-cut pTlc27 vector fragment were incubated in the presence of 500 Weiss Units of T4 DNA ligase (Promega) in a total volume of 8 ml (50 mM Tris/HCl pH 7.8, 10 mM $MgCl_2$, 10 mM DTT, 1 mM ATP, 50 μg/ml BSA) for 48 h at 16° C. The DNA was then precipitated from the ligation mixture by adding 210 μl yeast tRNA (10 mg/ml solution in $H_2O$; Roche), 8.4 ml 5 M ammonium acetate, and 33.6 ml ethanol. Further processing was performed according to Example 2 and at the end the DNA was dissolved to a final concentration of 200 μg/ml in a total volume of 400 μl of water.

The preparation and transformation of electrocompetent *E. coli* XL1-Blue was carried out according to Example 2. By employing a total of 73 μg ligated DNA about $2.0\times10^9$ transformants were obtained in altogether 40 electroporation runs. The transformants were further used for preparation of phagemids as described there.

For the selection of affinity-improved and also possibly more stable CD4-specific Tlc muteins four rounds of selection were performed with the same strategy according to the general method described in Example 3, but using more stringent conditions. Prior to the incubation with the target protein, i.e. biotinylated CD4-D 12-strep II, phagemids from the library were heated at 60° C. for 30 min and then blocked with 2% w/v BSA in PBS/T for 30 minutes at RT. Then the phagemid solution was incubated with 40 μl of 0.1 μM Bio-CD4-D12-strep II (final conc. 10 nM) for 1 h.

For the subsequent colony screening assay, the gene cassette between the two BstXI cleavage sites was subcloned from the phagemid vector pTlc27 onto pTlc28 (FIG. 2), as described in Example 4. For this purpose the plasmid DNA of the phagemid population from the 4th selection cycle was isolated. After transformation of *E. coli* K12 TG1-F cells with the ligation mixture, the filter-sandwich colony screening assay was essentially carried out as described in Example 4.

For the identification of affinity-improved CD4-specific muteins the hydrophobic membranes were screened in parallel with 3 different concentrations of digoxigenin-labelled CD4-D12-strep II (10 nM, 3 nM, and 1 nM, respectively). Bound DIG-CD4-D12-strep II was detected via anti-digoxigenin Fab fragment conjugated with alkaline phosphatase (1:1000, Roche Diagnostics).

A total of 14 clones that gave rise to the highest signal on the lowest concentration of DIG-CD4-D12-strep II were selected, propagated, and the nucleotide sequence of the respective Tlc gene cassette was determined using the oligodeoxynucleotide (F-83-AGA CAG CTA TCG CGA TTG CA) (SEQ ID NO: 35) as primer on an automated Genetic Analyzer system (Applied Biosystems) according to the instructions of the manufacturer employing the Big Dye Terminator Cycle Sequencing Kit (Applied Biosystems). 8 unique muteins containing a functional insert were identified. From these, 2 clones, M23.11A and M23.31B (FIG. 10), were selected for further characterization.

The gene cassettes were subcloned on pTlc28 and used for expression in *E. coli* JM83 in the shaker flask, followed by streptavidin affinity chromatography and size exclusion chromatography as described in Example 6. It was found that both Tlc muteins, M23.11A and M23.31B, could be eluted from the size exclusion chromatography (SEC) as monomeric proteins. The affinities of these Tlc muteins were determined in an ELISA and in a competitive ELISA as described in Example 7 (FIGS. 12, 13, and 14).

Example 9

Generation of a Targeted Loop Randomization Library for the CD4 Specific Mutein Mut23* and Affinity Maturation Loop 2 and 4 of M23* were in parallel subjected to random mutagenesis. Two separate libraries with high complexity were prepared by either concerted mutagenesis of the 5 selected amino acid positions 57, 58, 60, 61, 62, and 64 for loop 2 using the degenerated primer AN-LW2R (CGGTTC-CAGTGGTACGACNNSNNSCCGNNSAG-GNNSCTCNNSTTCCGGCAGGACCTC TTC-'5) (SEQ ID NO: 36) or concerted mutagenesis of sequence positions 102, 104, 105, 106, and 107 in loop 4 using the degenerated primer AN-LW4R (GTGATGTAGAAAATGAGANNSC-CGNNSNNSNNSNNSTTCGGCCAGGGTCCCCACACC GAGC-'5) (SEQ ID NO: 37). Generation of the libraries was carried out as described in Example 2. For selection of CD4-specific Tlc muteins, phagemids of both libraries were combined and then an aliquot of 300 µl was used as described in Example 3. Digoxigenated CD4-D12-strepII (10 nM for 1st selection round and 5 nM for the rounds 2-4) was added to the pre-blocked paramagnetic particles coated with an anti-Digoxigenin antibody (Europa Bioproducts) for 30 min. After three washes, phagemids were added for 30 min. After several washing steps, adsorbed phagemids were eluted under denaturing conditions with 0.1 M glycine/HCl pH 2.2 as described in Example 3.

Epitope-specific Tlc muteins were identified by means of the colony screening assay as described in Examples 4 and 5 and the DNA sequences of their coding regions were determined (FIG. 15). Selected affinity-improved Tlc muteins were produced as described in Example 6.

TABLE 3

Sequence characteristics of selected Tlc muteins

| pos.: | 57 | 58 | 60 | 62 | 64 | 79 | 97 |
|---|---|---|---|---|---|---|---|
| wtTlc | Ile | Ser | Arg | Gln | Val | Ala | Tyr |
| M23* | Ser | Gly | Arg | Gln | Val | Ala | Tyr |
| M23*.5 | His | Lys | Lys | Arg | His | | |
| M23*.14 | His | Lys | Lys | Lys | Tyr | | |
| M23*.28 | His | Arg | His | His | His | | Cys |
| M23*.30 | Ile | Lys | Arg | Lys | His | | |
| M23*.34 | Thr | Lys | Lys | Lys | Trp | | |
| M23*.36 | Val | His | Lys | Arg | Tyr | | |
| M23*.39 | Lys | His | Lys | Lys | Thr | Val | |
| M23*.40 | Lys | Lys | Lys | Ile | His | | |
| M23*.41 | Arg | Lys | Arg | Glu | Trp | | |
| M23*.45 | Arg | Lys | Lys | Thr | His | Val | |
| M23*.49 | Trp | Lys | Lys | Val | Arg | | |
| M23*.50 | Glu | Arg | Lys | Arg | Tyr | | |
| M23*.52 | His | Lys | Arg | Lys | His | | |

Example 10

Characterization of Binding Activity Towards the Cellular Receptor CD4 for the Tlc Muteins Using Flow Cytometry The selected Tlc muteins were tested for specific binding to a PM1 cell line expressing human CD4 in a flow cytometry assay using a FACScalibur instrument. As a control non CD4-expressing Raji cells were used.

Cell lines were detached from culture flasks with 0.2% w/v EDTA. Approximately 200000 cells (PM1 and Raji) were resuspended in 30 µl PBS containing 2% v/v FCS and incubated for 45 min at 4° C. with 2 µM, 1 µM, 0.5 µM, 0.25 µM or lower concentrations of wild type Tlc or the Tlc muteins M23*, M23*.39, M23*.41, and M23*.49, respectively, which had been prepared as soluble proteins as described in Example 6. The cells were washed twice in PBS/FCS, resuspended in 30 µl of the same buffer, and incubated with anti-STREP-TAG® II (200 ng, Qiagen #34850) for 1 h at 4° C. After two washes, anti-mIgG Fc-PE (1 µg, Dianova, #115-116-071) was added and incubated for 30 min at 4° C. The cells were washed twice with PBS/FCS prior to analysis by flow cytofluorimetry using a FACSCalibur instrument (Becton Dickinson). CD4 expression was confirmed with D2-specific anti-CD4 antibody (1 µg, Ancell #M-T441).

This cell-based assay revealed that both M23* and the affinity-improved CD4-specific muteins M23*.39, M23*.49, and, in particular, M23*.41 were capable of binding to PM1 cells, whereas no binding was detected with the Raji cells. The wild type Tlc showed no significant binding to both cell lines tested, thus indicating specific binding of the Tlc muteins to human CD4. The measured histograms are depicted in FIG. 16.

What is claimed is:

1. A mutein of human tear lipocalin, wherein the mutein comprises at least two amino acid mutations of wild type mature human tear lipocalin (SEQ ID NO: 1), and where said mutations are at two positions selected from the group consisting of positions 24-36, 53-66, 79-84, and 102-110 of said wild type mature human tear lipocalin, wherein said mutations includes at least one substitution selected from the group consisting of: Arg60→Lys, His; Gln62→Lys, Arg, His, Ile, Thr; and Gln64→His, Aro, Trp, Tyr and at least one substitution selected from Glu104→Ser, Ala, Leu, Trp, Tyr, Ile, and wherein the mutein binds to the extracellular region of the T-cell coreceptor CD4 with detectable affinity.

2. The mutein of claim 1, wherein the mutein blocks the interaction between CD4 and with the glycoprotein gp120 of human immunodeficiency virus HIV.

3. The mutein of claim 1, wherein the mutein binds to the extracellular D1 and/or D2 domain of CD4.

4. The mutein of claim 1, wherein the mutein binds human CD4 with a $K_D$ of 250 nM or less.

5. The mutein of claim 4, wherein the mutein binds CD4 with a $K_D$ of 750 nM, 500 mM, 100 nM or less.

6. The mutein of claim 5, wherein the mutein binds CD4 with a $K_D$ of 25 nM or less.

7. The mutein of claim 1, wherein the mutein comprises at least 2, 5, 8, 10, 12, 14, 15, 16, 18, 20 or 22 mutated amino acid residues at any of the sequence positions 26, 27, 28, 29, 30, 31, 32, 33, 34, 56, 57, 58, 60, 61, 62, 64, 80, 83, 102, 104, 105, 106, 107 and 108 of the linear polypeptide sequence of the mature human tear lipocalin.

8. The mutein of claim 7, wherein the mutein comprises mutated amino acid residues at all 23 of the sequence positions 26, 27, 28, 29, 30, 31, 32, 33, 34, 56, 57, 58, 60, 62, 64, 80, 83, 102, 104, 105, 106, 107 and 108.

9. The mutein of claim 1, which comprises at least one substituted hydrophobic amino acid at any of the sequence positions selected from the group consisting of 104, 105, 106, and 108.

10. The mutein of claim 9, wherein the substituted hydrophobic amino acid at sequence positions 105, 106, or 108 is selected from the group consisting of Leu, Val, Trp and Tyr.

11. The mutein of claim 1, which comprises an amino acid having a free hydroxyl group at sequence position 104.

12. The mutein of claim 11, wherein the amino acid having a free sequence hydroxyl group is Ser or Tyr.

13. The mutein of claim 1 which comprises a basic amino acid at the sequence positions 106.

14. The mutein of claim 10, wherein the basic amino acid at sequence position 106 is either Arg or His.

15. The mutein of claim 1, which comprises with respect to the amino acid sequence of mature human tear lipocalin at least two amino acid replacements selected from the group consisting of Glu 27→Asn, Lys, Thr, Ser; Phe28→His, Lys, Arg, Asn; Pro29→Asn, Cys, Ser, Lys; Glu30→Asn, His, Lys, Tyr; Met31→Ile, Arg, Ser, Asn; Asn32→Phe, Ile, Ser, Arg; Leu33→Thr, Lys, Arg, Asn; Glu34→Ser, His, Ala, Asp; Leu56→Ser, Trp, Ala, Val; Ile57→Gly, Tyr, Ser, Cys, Leu, His, Lys, Val, Arg, Trp, Glu; Ser58→Phe, Lys, Leu, Gly, His, Arg; Arg60→Lys, His; Gln62→Lys, Arg, His, Ile, Thr; Gln64→His, Arg, Trp, Tyr; Asp80→Ile, Leu, Arg, His, Ser; Glu102→Lys; Leu105→Val, Trp, Phe; His106→Gly, His, Ley, Ile, Arg; Lys108→Val, Leu, Ile, Trp, Phe.

16. The mutein of claim 1, which further comprises with respect to the amino acid sequence of mature human tear lipocalin at least one of the amino acid substitutions selected from the group consisting of Cys61→Ser, Cys153→Ser, Arg111→Pro, and Lys114→Trp.

17. The mutein claim 1, wherein the mutein has an amino acid sequence selected from the group consisting of the sequences M25 (SEQ ID NO: 5), M32 (SEQ ID NO: 7), M31 (SEQ ID NO: 9), M18 (SEQ ID NO: 11), M18*(SEQ ID NO: 13), M48 (SEQ ID NO: 15), M154 (SEQ ID NO: 17), M23 (SEQ ID NO: 19), M23*(SEQ ID NO: 21), M23.11A (SEQ ID NO: 23), and M23.11B (SEQ ID NO: 25), as depicted in FIG. 10 or selected from the group of the sequences M23*.5 (SEQ ID NO: 39), M23*.14 (SEQ ID NO: 41), M23*.28 (SEQ ID NO: 43), M23*.30 (SEQ ID NO: 45), M23*.34 (SEQ ID NO: 47), M23*36 (SEQ ID NO: 49), M23.*39 (SEQ ID NO: 51), M23*40 (SEQ ID NO: 53), M23*41 (SEQ ID NO: 55), M23*.45 (SEQ ID NO: 57), M23*.49 (SEQ ID NO: 59), M23*.50 (SEQ ID NO: 61) and M23*.52 (SEQ ID NO: 63) as depicted in FIG. 15.

18. The mutein of claim 1, wherein the mutein is conjugated to a moiety that extends the serum half-life of the mutein.

19. The mutein of claim 18, wherein the moiety that extends the serum half-life is selected from the group consisting of a polyalkylene glycol molecule, hydroxyethylstarch, an Fc part of an immunoglobulin, a CH3 domain of an immunoglobulin, a CH4 domain of an immunoglobulin, albumin, an albumin binding peptide, and an albumin binding protein.

20. The mutein of claim 1, wherein the mutein is fused at its N-terminus and/or its C-terminus to a protein, a protein domain or a peptide.

21. The mutein of claim 20, wherein the fusion partner extends the serum half-life of the mutein.

22. A pharmaceutical composition comprising at least one mutein of claim 1.

23. A method for the generation of a mutein of human tear lipocalin of claim 1, comprising:
   (a) subjecting a nucleic acid molecule encoding human tear lipocalin to mutagenesis at least two codons encoding any of the amino acid sequence positions 24-36, 53-66, 79-84, and 102-110 of the linear polypeptide sequence of wild type mature human tear lipocalin (SEQ ID NO: 1), wherein said codon mutations include at least one encoded substitution selected from the group consisting of: Arg60→Lys, His; Gln62→Lys, Arg, His, Ile, Thr; and Gln64→His, Arg, Trp, Tyr and at least one substitution selected from Glu104→Ser, Ala, Leu, Trp, Tyr, Ile, thereby obtaining a plurality of nucleic acids encoding muteins of human tear lipocalin,
   (b) expressing the plurality of nucleic acid molecules obtained in (a) in a suitable expression system, thereby generating a plurality of muteins of human tear lipocalin,
   (c) bringing the plurality of muteins of human tear lipocalin into contact with at least a fragment of the extracellular region of the T-cell receptor CD4, and
   (d) enriching at least one mutein having a detectable binding affinity for the at least one fragment of the extracellular region of CD4 by means of selection, physical separation and/or isolation.

24. The method of claim 23, wherein the fragment of CD4 comprises the extracellular domain D1 and/or domain D2 of CD4.

* * * * *

UNITED STATES PATENT AND TRADEMARK OFFICE
CERTIFICATE OF CORRECTION

PATENT NO. : 8,598,317 B2
APPLICATION NO. : 12/293715
DATED : December 3, 2013
INVENTOR(S) : Arne Skerra et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 868 days.

Signed and Sealed this
Twenty-first Day of April, 2015

Michelle K. Lee
*Director of the United States Patent and Trademark Office*

SEQUENCE LISTING

```
<160> NUMBER OF SEQ ID NOS: 65

<210> SEQ ID NO 1
<211> LENGTH: 158
<212> TYPE: PRT
<213> ORGANISM: Homo sapiens

<400> SEQUENCE: 1

His His Leu Leu Ala Ser Asp Glu Glu Ile Gln Asp Val Ser Gly Thr
```

```
1               5                   10                  15
Trp Tyr Leu Lys Ala Met Thr Val Asp Arg Glu Phe Pro Glu Met Asn
            20                  25                  30

Leu Glu Ser Val Thr Pro Met Thr Leu Thr Thr Leu Glu Gly Gly Asn
        35                  40                  45

Leu Glu Ala Lys Val Thr Met Leu Ile Ser Gly Arg Cys Gln Glu Val
    50                  55                  60

Lys Ala Val Leu Glu Lys Thr Asp Glu Pro Gly Lys Tyr Thr Ala Asp
65                  70                  75                  80

Gly Gly Lys His Val Ala Tyr Ile Ile Arg Ser His Val Lys Asp His
                85                  90                  95

Tyr Ile Phe Tyr Cys Glu Gly Glu Leu His Gly Lys Pro Val Arg Gly
            100                 105                 110

Val Lys Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly Ser Asp
145                 150                 155
```

<210> SEQ ID NO 2
<211> LENGTH: 477
<212> TYPE: DNA
<213> ORGANISM: Artificial
<220> FEATURE:
<223> OTHER INFORMATION: Human tear lipocalin mutein CDS

<400> SEQUENCE: 2

```
caccacctcc tggcctcaga cgaggagatt caggatgtgt cagggacgtg gtatctgaag    60
gccatgacgg tggacaggga gttccctgag atgaatctgg aatcggtgac acccatgacc   120
ctcacgaccc tggaaggggg caacctggaa gccaaggtca ccatgctgat aagtggccgg   180
agccaggagg tgaaggccgt cctggagaaa actgacgagc cgggaaaata cacggccgac   240
ggggcaagc acgtggcata catcatcagg tcgcacgtga aggaccacta catcttttac   300
tctgagggcg agctccacgg gaagccggtc caggggtgt ggctcgtggg cagagacccc   360
aagaacaacc tggaagcctt ggaggacttt gagaaagccg caggagcccg cggactcagc   420
acggagagca tcctcatccc caggcagagc gaaacctgct ctccagggag cgattag      477
```

<210> SEQ ID NO 3
<211> LENGTH: 158
<212> TYPE: PRT
<213> ORGANISM: Artificial
<220> FEATURE:
<223> OTHER INFORMATION: Human tear lipocalin mutein

<400> SEQUENCE: 3

```
His His Leu Leu Ala Ser Asp Glu Glu Ile Gln Asp Val Ser Gly Thr
1               5                   10                  15

Trp Tyr Leu Lys Ala Met Thr Val Asp Arg Glu Phe Pro Glu Met Asn
            20                  25                  30

Leu Glu Ser Val Thr Pro Met Thr Leu Thr Thr Leu Glu Gly Gly Asn
        35                  40                  45

Leu Glu Ala Lys Val Thr Met Leu Ile Ser Gly Arg Ser Gln Glu Val
    50                  55                  60

Lys Ala Val Leu Glu Lys Thr Asp Glu Pro Gly Lys Tyr Thr Ala Asp
65                  70                  75                  80
```

```
Gly Gly Lys His Val Ala Tyr Ile Ile Arg Ser His Val Lys Asp His
                85                  90                  95

Tyr Ile Phe Tyr Ser Glu Gly Glu Leu His Gly Lys Pro Val Pro Gly
            100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly Ser Asp
145                 150                 155
```

<210> SEQ ID NO 4
<211> LENGTH: 477
<212> TYPE: DNA
<213> ORGANISM: Artificial
<220> FEATURE:
<223> OTHER INFORMATION: Human tear lipocalin mutein M25 CDS

<400> SEQUENCE: 4

```
caccacctcc tggcctcaga cgaggagatt caggatgtgt cagggacgtg gtatctgaag    60
gccatgacgg tggacaacaa ccgcaacaac atcatcaacc actcggtgac acccatgacc   120
ctcacgaccc tggaaggggg caacctggaa gccaaggtca ccatgtgggg tttcggccgg   180
tcccaggagg tgaaggccgt cctggagaaa actgatgagc cgggaaaata cacgccagc    240
gagggcgatc acgtggcata catcatcagg tcgcacgtga aggaccacta catcttttac   300
tctgagggct cgtggctggg gttcccggtc caggggtgt ggctcgtggg cagagacccc    360
aagaacaacc tggaagcctt ggaggacttt gagaaagccg caggagcccg cggactcagc   420
acggagagca tcctcatccc caggcagagc gaaacctgct ctccagggag cgattag     477
```

<210> SEQ ID NO 5
<211> LENGTH: 158
<212> TYPE: PRT
<213> ORGANISM: Artificial
<220> FEATURE:
<223> OTHER INFORMATION: Human tear lipocalin mutein M25

<400> SEQUENCE: 5

```
His His Leu Leu Ala Ser Asp Glu Glu Ile Gln Asp Val Ser Gly Thr
1               5                   10                  15

Trp Tyr Leu Lys Ala Met Thr Val Asp Asn Asn Arg Asn Asn Ile Ile
            20                  25                  30

Asn His Ser Val Thr Pro Met Thr Leu Thr Thr Leu Glu Gly Gly Asn
        35                  40                  45

Leu Glu Ala Lys Val Thr Met Trp Gly Phe Gly Arg Ser Gln Glu Val
50                  55                  60

Lys Ala Val Leu Glu Lys Thr Asp Glu Pro Gly Lys Tyr Thr Ala Ser
65                  70                  75                  80

Glu Gly Asp His Val Ala Tyr Ile Ile Arg Ser His Val Lys Asp His
                85                  90                  95

Tyr Ile Phe Tyr Ser Glu Gly Ser Trp Leu Gly Phe Pro Val Pro Gly
            100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly Ser Asp
145                 150                 155
```

<210> SEQ ID NO 6
<211> LENGTH: 477
<212> TYPE: DNA
<213> ORGANISM: Artificial
<220> FEATURE:
<223> OTHER INFORMATION: Human tear lipocalin mutein M32 CDS

<400> SEQUENCE: 6

```
caccacctcc tggcctcaga cgaggagatt caggatgtgt cagggacgtg gtatctgaag      60
gccatgacgg tggacaacaa ccaccacaag cgcagcaagc actcggtgac acccatgacc     120
ctcacgaccc tggaaggggg caacctggac gccaaggtca tcatgttgct gctgggccgg     180
tcccaggagg tgaaggccgt cctggagaaa actgatgagc cgggaaaata cacggccatc     240
gggggcgagc acgtggcata catcatcagg tcgcacgtga aggaccacta catcttttac     300
tctaagggct actggatcgg gttaccggtc caggggtgt ggctcgtggg cagagacccc      360
aagaacaacc tggaagcctt ggaggacttt gagaaagccg caggagcccg cggactcagc     420
acggagagca tcctcatccc caggcagagc gaaacctgct ctccagggag cgattag        477
```

<210> SEQ ID NO 7
<211> LENGTH: 158
<212> TYPE: PRT
<213> ORGANISM: Artificial
<220> FEATURE:
<223> OTHER INFORMATION: Human tear lipocalin mutein M32

<400> SEQUENCE: 7

```
His His Leu Leu Ala Ser Asp Glu Glu Ile Gln Asp Val Ser Gly Thr
 1               5                  10                  15

Trp Tyr Leu Lys Ala Met Thr Val Asp Asn Asn His His Lys Arg Ser
            20                  25                  30

Lys His Ser Val Thr Pro Met Thr Leu Thr Thr Leu Glu Gly Gly Asn
        35                  40                  45

Leu Asp Ala Lys Val Ile Met Leu Leu Leu Gly Arg Ser Gln Glu Val
    50                  55                  60

Lys Ala Val Leu Glu Lys Thr Asp Glu Pro Gly Lys Tyr Thr Ala Ile
65                  70                  75                  80

Gly Gly Glu His Val Ala Tyr Ile Ile Arg Ser His Val Lys Asp His
                85                  90                  95

Tyr Ile Phe Tyr Ser Lys Gly Tyr Trp Ile Gly Leu Pro Val Pro Gly
            100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly Ser Asp
145                 150                 155
```

<210> SEQ ID NO 8
<211> LENGTH: 477
<212> TYPE: DNA
<213> ORGANISM: Artificial
<220> FEATURE:
<223> OTHER INFORMATION: Human tear lipocalin mutein M31 CDS

<400> SEQUENCE: 8

```
caccacctcc tggcctcaga cgaggagatt caggatgtgt cagggacgtg gtatctgaag      60
gccatgacgg tggacaccaa caacaacaac agcatcaccg cctcggtgac acccatgacc     120
```

```
ctcacgaccc tggaagggggg caacctggaa gccaaggtca ccatgctgcg cttgggccgg      180
tcccaggagg tgaaggccgt cctggagaaa actgatgagc cgggaaaata cacggccatc      240 ggggctacc acgtggcata catcatcagg tcgcacgtga aggaccacta catcttttac       300
tctgagagct cgttgctggg ggtgccggtc caggggtgt ggctcgtggg cagagacccc       360
aagaacaacc tggaagcctt ggaggacttt gagaaagccg caggagcccg cggactcagc      420
acggagagca tcctcatccc caggcagagc gaaacctgct ctccagggag cgattag         477
```

```
<210> SEQ ID NO 9
<211> LENGTH: 158
<212> TYPE: PRT
<213> ORGANISM: Artificial
<220> FEATURE:
<223> OTHER INFORMATION: Human tear lipocalin mutein M31

<400> SEQUENCE: 9
```

```
His His Leu Leu Ala Ser Asp Glu Glu Ile Gln Asp Val Ser Gly Thr
  1               5                  10                  15

Trp Tyr Leu Lys Ala Met Thr Val Asp Thr Asn Asn Asn Asn Ser Ile
             20                  25                  30

Thr Ala Ser Val Thr Pro Met Thr Leu Thr Thr Leu Glu Gly Gly Asn
         35                  40                  45

Leu Glu Ala Lys Val Thr Met Leu Arg Leu Gly Arg Ser Gln Glu Val
     50                  55                  60

Lys Ala Val Leu Glu Lys Thr Asp Glu Pro Gly Lys Tyr Thr Ala Ile
 65                  70                  75                  80

Gly Gly Tyr His Val Ala Tyr Ile Ile Arg Ser His Val Lys Asp His
                 85                  90                  95

Tyr Ile Phe Tyr Ser Glu Ser Ser Leu Leu Gly Val Pro Val Pro Gly
            100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly Ser Asp
145                 150                 155
```

```
<210> SEQ ID NO 10
<211> LENGTH: 477
<212> TYPE: DNA
<213> ORGANISM: Artificial
<220> FEATURE:
<223> OTHER INFORMATION: Human tear lipocalin mutein M18 CDS

<400> SEQUENCE: 10
caccacctcc tggcctcaga cgaggagatt caggatgtgt cagggacgtg gtatctgaag      60
gccatgacgg tggacccgaa gaactgcaag aggttcacgt cctcggtgac acccatgacc     120
ctcacgaccc tggaagggggg caacctggaa gccaaggtca ccatgtcgta caagggccgg    180
tcccaggagg tgaaggccgt cctggagaaa actgatgagc cgggaaaata cacggcccgg    240 ggggccagc acgcggcata catcatcagg tcgcacgtga aggaccacta catcttttac      300
tctaagggct ggttgagggg gttgccggtc caggggtgt ggctcgtggg cagagacccc     360
aagaacaacc tggaagcctt ggaggacttt gagaaagccg caggagcccg cggactcagc     420
acggagagca tcctcatccc caggcagagc gaaacctgct ctccagggag cgattag        477
```

```
<210> SEQ ID NO 11
<211> LENGTH: 158
<212> TYPE: PRT
<213> ORGANISM: Artificial
<220> FEATURE:
<223> OTHER INFORMATION: Human tear lipocalin mutein M18

<400> SEQUENCE: 11

His His Leu Leu Ala Ser Asp Glu Glu Ile Gln Asp Val Ser Gly Thr
1               5                   10                  15

Trp Tyr Leu Lys Ala Met Thr Val Asp Pro Lys Asn Cys Lys Arg Phe
            20                  25                  30

Thr Ser Ser Val Thr Pro Met Thr Leu Thr Thr Leu Glu Gly Gly Asn
        35                  40                  45

Leu Glu Ala Lys Val Thr Met Ser Tyr Lys Gly Arg Ser Gln Glu Val
    50                  55                  60

Lys Ala Val Leu Glu Lys Thr Asp Glu Pro Gly Lys Tyr Thr Ala Arg
65                  70                  75                  80

Gly Gly Gln His Ala Ala Tyr Ile Ile Arg Ser His Val Lys Asp His
                85                  90                  95

Tyr Ile Phe Tyr Ser Lys Gly Trp Leu Arg Gly Leu Pro Val Pro Gly
            100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly Ser Asp
145                 150                 155

<210> SEQ ID NO 12
<211> LENGTH: 477
<212> TYPE: DNA
<213> ORGANISM: Artificial
<220> FEATURE:
<223> OTHER INFORMATION: Human tear lipocalin mutein M18* CDS

<400> SEQUENCE: 12
caccacctcc tggcctcaga cgaggagatt caggatgtgt cagggacgtg gtatctgaag     60
gccatgacgg tggacccgaa gaactccaag aggttcacgt cctcggtgac acccatgacc    120
ctcacgaccc tggaaggggg caacctggaa gccaaggtca ccatgtcgta caagggccgg    180
tcccaggagg tgaaggccgt cctggagaaa actgatgagc cgggaaaata cacggcccgg    240
gggggccagc acgcggcata tcatcaggt cgcacgtga aggaccacta catcttttac     300
tctaagggct ggttgagggg gttgccggtc ccaggggtgt ggctcgtggg cagagacccc    360
aagaacaacc tggaagcctt ggaggacttt gagaaagccg caggagcccg cggactcagc    420
acggagagca tcctcatccc caggcagagc gaaacctgct ctccagggag cgattag        477

<210> SEQ ID NO 13
<211> LENGTH: 158
<212> TYPE: PRT
<213> ORGANISM: Artificial
<220> FEATURE:
<223> OTHER INFORMATION: Human tear lipocalin mutein M18*

<400> SEQUENCE: 13

His His Leu Leu Ala Ser Asp Glu Glu Ile Gln Asp Val Ser Gly Thr
1               5                   10                  15

Trp Tyr Leu Lys Ala Met Thr Val Asp Pro Lys Asn Ser Lys Arg Phe
            20                  25                  30
```

Thr Ser Ser Val Thr Pro Met Thr Leu Thr Thr Leu Glu Gly Gly Asn
        35                  40                  45

Leu Glu Ala Lys Val Thr Met Ser Tyr Lys Gly Arg Ser Gln Glu Val
 50                  55                  60

Lys Ala Val Leu Glu Lys Thr Asp Glu Pro Gly Lys Tyr Thr Ala Arg
 65                  70                  75                  80

Gly Gly Gln His Ala Ala Tyr Ile Ile Arg Ser His Val Lys Asp His
                 85                  90                  95

Tyr Ile Phe Tyr Ser Lys Gly Trp Leu Arg Gly Leu Pro Val Pro Gly
                100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
        130                 135                 140

Leu Ile Pro Arg Gln Ser Glu Thr Cys Ser Pro Gly Ser Asp
145                 150                 155

<210> SEQ ID NO 14
<211> LENGTH: 477
<212> TYPE: DNA
<213> ORGANISM: Artificial
<220> FEATURE:
<223> OTHER INFORMATION: Human tear lipocalin mutein M48 CDS

<400> SEQUENCE: 14
caccacctcc tggcctcaga cgaggagatt caggatgtgt cagggacgtg gtatctgaag      60
gccatgacgg tggacaagac caagaagcac agcaagaagc actcggtgac acccatgacc     120
gtcacgaccc tggaaggggg caacctggaa gccaaggtta ccatggtgct gaagggccgg     180
tcccaggagg tgaaggccgt cctggagaaa actgatgagc cgggaaaata cacggccaac     240
gggggccacc acgtggcata cttcatcagg tcgcacgtga aggaccacta tcttttac     300 tctgagggcg cggtgctggg gtggccggtc ccaggggtgt ggctcgtggg cagagacccc     360
aagaacaacc tggaagcctt ggaggacttt gagaaagccg caggagcccg cggactcagc     420
acggagagca tcctcatccc caggcagagc gaaacctgct ctccagggag cgattag         477

<210> SEQ ID NO 15
<211> LENGTH: 158
<212> TYPE: PRT
<213> ORGANISM: Artificial
<220> FEATURE:
<223> OTHER INFORMATION: Human tear lipocalin mutein M48

<400> SEQUENCE: 15

His His Leu Leu Ala Ser Asp Glu Glu Ile Gln Asp Val Ser Gly Thr
  1               5                  10                  15

Trp Tyr Leu Lys Ala Met Thr Val Asp Lys Thr Lys Lys His Ser Lys
                 20                  25                  30

Lys His Ser Val Thr Pro Met Thr Val Thr Thr Leu Glu Gly Gly Asn
                 35                  40                  45

Leu Glu Ala Lys Val Thr Met Val Leu Lys Gly Arg Ser Gln Glu Val
 50                  55                  60

Lys Ala Val Leu Glu Lys Thr Asp Glu Pro Gly Lys Tyr Thr Ala Asn
 65                  70                  75                  80

Gly Gly His His Val Ala Tyr Phe Ile Arg Ser His Val Lys Asp His
                 85                  90                  95

Tyr Ile Phe Tyr Ser Glu Gly Ala Val Leu Gly Trp Pro Val Pro Gly

Val Trp Leu Val Gly Arg Asp Pro Lys Asn Asn Leu Glu Ala Leu Glu
            115                 120                 125

Asp Phe Glu Lys Ala Ala Gly Ala Arg Gly Leu Ser Thr Glu Ser Ile
        130                 135                 140

Leu Ile Pro Arg Gln Ser Glu Thr Cys Ser Pro Gly Ser Asp
145                 150                 155

<210> SEQ ID NO 16
<211> LENGTH: 477
<212> TYPE: DNA
<213> ORGANISM: Artificial
<220> FEATURE:
<223> OTHER INFORMATION: Human tear lipocalin mutein M154 CDS

<400> SEQUENCE: 16

```
caccacctcc tggcctcaga cgaggagatt caggatgtgt cagggacgtg gtatctgaag      60
gccatgacgg tggacaccaa caacaacaac aggagcaccg actcggtgac acccatgacc     120
ctcacgaccc tggaaggggg caacctggaa gccaaggtca ccatggcatt gttcggccgg     180
tcccaggagg tgaaggccgt cctggagaaa actgatgagc cgggaaaata cacggcccac     240
gggggctccc acgtggcaca tcatcagg tcgcacgtga aggaccacta tcttttac        300
tctgagggct ggttccgcgg gttcccggtc caggggtgt ggctcgtggg cagagacccc      360
aagaacaacc tggaagcctt ggaggacttt gagaagccg caggagcccg cggactcagc      420
acggagagca tcctcatccc caggcagagc gaaacctgct ctccagggag cgattag       477
```

<210> SEQ ID NO 17
<211> LENGTH: 158
<212> TYPE: PRT
<213> ORGANISM: Artificial
<220> FEATURE:
<223> OTHER INFORMATION: Human tear lipocalin mutein M154

<400> SEQUENCE: 17

His His Leu Leu Ala Ser Asp Glu Glu Ile Gln Asp Val Ser Gly Thr
1               5                   10                  15

Trp Tyr Leu Lys Ala Met Thr Val Asp Thr Asn Asn Asn Asn Arg Ser
            20                  25                  30

Thr Asp Ser Val Thr Pro Met Thr Leu Thr Thr Leu Glu Gly Gly Asn
        35                  40                  45

Leu Glu Ala Lys Val Thr Met Ala Leu Phe Gly Arg Ser Gln Glu Val
    50                  55                  60

Lys Ala Val Leu Glu Lys Thr Asp Glu Pro Gly Lys Tyr Thr Ala His
65                  70                  75                  80

Gly Gly Ser His Val Ala His Ile Ile Arg Ser His Val Lys Asp His
                85                  90                  95

Tyr Ile Phe Tyr Ser Glu Gly Trp Phe Arg Gly Phe Pro Val Pro Gly
            100                 105                 110

Val Trp Leu Val Gly Arg Asp Pro Lys Asn Asn Leu Glu Ala Leu Glu
            115                 120                 125

Asp Phe Glu Lys Ala Ala Gly Ala Arg Gly Leu Ser Thr Glu Ser Ile
        130                 135                 140

Leu Ile Pro Arg Gln Ser Glu Thr Cys Ser Pro Gly Ser Asp
145                 150                 155

<210> SEQ ID NO 18
<211> LENGTH: 477

```
<212> TYPE: DNA
<213> ORGANISM: Artificial
<220> FEATURE:
<223> OTHER INFORMATION: Human tear lipocalin mutein M23 CDS

<400> SEQUENCE: 18
caccacctcc tggcctcaga cgaggagatt caggatgtgt cagggacgtg gtatctgaag      60
gccatgacgg tggacaacag caagaagtac aacaggcgcc actcggtgac agccatgacc     120
ctcacgaccc tggaaggggg caacctggaa gccaaggtca ccatgttgtg cggggggccgg    180 tcccaggagg tgaaggccgt cctggagaaa actgacgagc cgggaaaata cacggccctc    240
gggggcgacc acgtggcata catcatcagg tcgcacgtga aggaccacta catcttttac    300
tctaagggct ggttgggggg gttcccggtc ccagggtgt ggctcgtggg cagagacccc     360
aagaacaacc tggaagcctt ggaggacttt gagaaagccg caggagcccg cggactcagc    420
acggagagca tcctcatccc caggcagagc gaaacctgct ctccagggag cgattag       477

<210> SEQ ID NO 19
<211> LENGTH: 158
<212> TYPE: PRT
<213> ORGANISM: Artificial
<220> FEATURE:
<223> OTHER INFORMATION: Human tear lipocalin mutein M23

<400> SEQUENCE: 19

His His Leu Leu Ala Ser Asp Glu Glu Ile Gln Asp Val Ser Gly Thr
1               5                   10                  15

Trp Tyr Leu Lys Ala Met Thr Val Asp Asn Ser Lys Lys Tyr Asn Arg
            20                  25                  30

Arg His Ser Val Thr Ala Met Thr Leu Thr Thr Leu Glu Gly Gly Asn
        35                  40                  45

Leu Glu Ala Lys Val Thr Met Leu Cys Gly Gly Arg Ser Gln Glu Val
    50                  55                  60

Lys Ala Val Leu Glu Lys Thr Asp Glu Pro Gly Lys Tyr Thr Ala Leu
65                  70                  75                  80

Gly Gly Asp His Val Ala Tyr Ile Ile Arg Ser His Val Lys Asp His
                85                  90                  95

Tyr Ile Phe Tyr Ser Lys Gly Trp Leu Gly Gly Phe Pro Val Pro Gly
            100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly Ser Asp
145                 150                 155

<210> SEQ ID NO 20
<211> LENGTH: 477
<212> TYPE: DNA
<213> ORGANISM: Artificial
<220> FEATURE:
<223> OTHER INFORMATION: Human tear lipocalin mutein M23* CDS

<400> SEQUENCE: 20
caccacctcc tggcctcaga cgaggagatt caggatgtgt cagggacgtg gtatctgaag      60
gccatgacgg tggacaacag caagaagtac aacaggcgcc actcggtgac agccatgacc     120
ctcacgaccc tggaaggggg caacctggaa gccaaggtca ccatgttgtc cggggggccgg    180 tcccaggagg tgaaggccgt cctggagaaa actgacgagc cgggaaaata cacggccctc    240
```

```
ggggggcgacc acgtggcata catcatcagg tcgcacgtga aggaccacta catcttttac    300
tctaagggct ggttgggggg gttcccggtc cagggggtgt ggctcgtggg cagagacccc    360
aagaacaacc tggaagcctt ggaggacttt gagaaagccg caggagcccg cggactcagc    420
acggagagca tcctcatccc caggcagagc gaaacctgct ctccagggag cgattag      477
```

<210> SEQ ID NO 21
<211> LENGTH: 158
<212> TYPE: PRT
<213> ORGANISM: Artificial
<220> FEATURE:
<223> OTHER INFORMATION: Human tear lipocalin mutein M23*

<400> SEQUENCE: 21

```
His His Leu Leu Ala Ser Asp Glu Glu Ile Gln Asp Val Ser Gly Thr
1               5                  10                  15

Trp Tyr Leu Lys Ala Met Thr Val Asp Asn Ser Lys Lys Tyr Asn Arg
            20                  25                  30

Arg His Ser Val Thr Ala Met Thr Leu Thr Thr Leu Glu Gly Gly Asn
        35                  40                  45

Leu Glu Ala Lys Val Thr Met Leu Ser Gly Gly Arg Ser Gln Glu Val
    50                  55                  60

Lys Ala Val Leu Glu Lys Thr Asp Glu Pro Gly Lys Tyr Thr Ala Leu
65                  70                  75                  80

Gly Gly Asp His Val Ala Tyr Ile Ile Arg Ser His Val Lys Asp His
                85                  90                  95

Tyr Ile Phe Tyr Ser Lys Gly Trp Leu Gly Gly Phe Pro Val Pro Gly
            100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly Ser Asp
145                 150                 155
```

<210> SEQ ID NO 22
<211> LENGTH: 477
<212> TYPE: DNA
<213> ORGANISM: Artificial
<220> FEATURE:
<223> OTHER INFORMATION: Human tear lipocalin mutein M23.11A CDS

<400> SEQUENCE: 22

```
caccacctcc tggcctcaga cgaggagatt caggatgtgt cagggacgtg gtatctgaag    60
gccatgacgg tggacagcag caagaagtac aacaggcgcc actcggtgac agccatgacc    120
ctcacgaccc tggaaggggg caacctggaa gccaaggtca ccatgttgtc cgggggccgg    180
tcccaggagg tgaaggccgt cctggagaaa actgacgagc cgggaaaata cacggccctc    240 ggggcgacc acgtggcata catcatcggg tcgcacgtga aggaccacta cattttttac    300
tctaagggct ggttgggggg gttcccggtc cagggggtgt ggctcgtggg cagagacccc    360
aagaacaacc tggaagcctt ggaggacttt gagaaagccg caggagcccg cggactcagc    420
acggagagca tcctcatccc caggcagagc gaaacctgct ctccagggag cgattag      477
```

<210> SEQ ID NO 23
<211> LENGTH: 158
<212> TYPE: PRT
<213> ORGANISM: Artificial

```
<220> FEATURE:
<223> OTHER INFORMATION: Human tear lipocalin mutein M23.11a

<400> SEQUENCE: 23

His His Leu Leu Ala Ser Asp Glu Glu Ile Gln Asp Val Ser Gly Thr
1               5                   10                  15

Trp Tyr Leu Lys Ala Met Thr Val Asp Ser Ser Lys Lys Tyr Asn Arg
                20                  25                  30

Arg His Ser Val Thr Ala Met Thr Leu Thr Thr Leu Glu Gly Gly Asn
            35                  40                  45

Leu Glu Ala Lys Val Thr Met Leu Ser Gly Gly Arg Ser Gln Glu Val
        50                  55                  60

Lys Ala Val Leu Glu Lys Thr Asp Glu Pro Gly Lys Tyr Thr Ala Leu
65                  70                  75                  80

Gly Gly Asp His Val Ala Tyr Ile Ile Gly Ser His Val Lys Asp His
                85                  90                  95

Tyr Ile Phe Tyr Ser Lys Gly Trp Leu Gly Gly Phe Pro Val Pro Gly
                100                 105                 110

Val Trp Leu Val Gly Arg Asp Pro Lys Asn Asn Leu Glu Ala Leu Glu
            115                 120                 125

Asp Phe Glu Lys Ala Ala Gly Ala Arg Gly Leu Ser Thr Glu Ser Ile
        130                 135                 140

Leu Ile Pro Arg Gln Ser Glu Thr Cys Ser Pro Gly Ser Asp
145                 150                 155

<210> SEQ ID NO 24
<211> LENGTH: 477
<212> TYPE: DNA
<213> ORGANISM: Artificial
<220> FEATURE:
<223> OTHER INFORMATION: Human tear lipocalin mutein M23.11b CDS

<400> SEQUENCE: 24
caccacctcc tggcctcaga cgaggagatt caggatgtgt cagggacgtg gtatctgaag     60
gccatgacgg tggacaacag caagaagtac aacaggcgcc actcggtgac agccatgacc    120
ctcacgaccc tggaaggggg caacctggaa gccaaggtca ccatgttgtc cggggggccgg   180 tcccaggagg tgaaggccgt cctggagaaa actgacgagc cgggaacata cacgccctc    240 ggggcgacc acgtggcata catcatcagg tcgcacgtga aggaccacta catcttttac    300
tctgagggct ggttgggggg gttcccggtc ccagggtgt ggctcgtggg cagagacccc    360
aagaacaacc tggaagcctt ggaggacttt gagaaagccg caggagcccg cggactcagc    420
acggagagca tcctcatccc caggcagagc gaaacctgct ctccagggag cgattag       477

<210> SEQ ID NO 25
<211> LENGTH: 158
<212> TYPE: PRT
<213> ORGANISM: Artificial
<220> FEATURE:
<223> OTHER INFORMATION: Human tear lipocalin mutein M23.11b

<400> SEQUENCE: 25

His His Leu Leu Ala Ser Asp Glu Glu Ile Gln Asp Val Ser Gly Thr
1               5                   10                  15

Trp Tyr Leu Lys Ala Met Thr Val Asp Asn Ser Lys Lys Tyr Asn Arg
                20                  25                  30

Arg His Ser Val Thr Ala Met Thr Leu Thr Thr Leu Glu Gly Gly Asn
            35                  40                  45
```

```
Leu Glu Ala Lys Val Thr Met Leu Ser Gly Gly Arg Ser Gln Glu Val
 50                  55                  60

Lys Ala Val Leu Glu Lys Thr Asp Glu Pro Gly Asn Tyr Thr Ala Leu
 65                  70                  75                  80

Gly Gly Asp His Val Ala Tyr Ile Ile Arg Ser His Val Lys Asp His
                 85                  90                  95

Tyr Ile Phe Tyr Ser Glu Gly Trp Leu Gly Gly Phe Pro Val Pro Gly
            100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly Ser Asp
145                 150                 155

<210> SEQ ID NO 26
<211> LENGTH: 24
<212> TYPE: DNA
<213> ORGANISM: Artificial
<220> FEATURE:
<223> OTHER INFORMATION: Oligonucleotide Primer AN-15F

<400> SEQUENCE: 26
tatctgaagg ccatgacggt ggac                                            24

<210> SEQ ID NO 27
<211> LENGTH: 63
<212> TYPE: DNA
<213> ORGANISM: Artificial
<220> FEATURE:
<223> OTHER INFORMATION: Oligonucleotide Primer AN-10
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t

<400> SEQUENCE: 27
aaggccatga cggtggacnn snnsnnsnns nnsnnsnnsn nsnnstcggt gacacccatg   60
``` acc                                                                          63

<210> SEQ ID NO 28
<211> LENGTH: 45
<212> TYPE: DNA
<213> ORGANISM: Artificial
<220> FEATURE:
<223> OTHER INFORMATION: Oligonucleotide Primer AN-11
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t

<400> SEQUENCE: 28
cacctcctgg gaccggccsn nsnnsnncat ggtgaccttg gcttc           45

<210> SEQ ID NO 29
<211> LENGTH: 54
<212> TYPE: DNA
<213> ORGANISM: Artificial
<220> FEATURE:
<223> OTHER INFORMATION: Oligonucleotide Primer AN-12
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t

<400> SEQUENCE: 29
gacgagccgg gaaaatacac ggccnnsggg ggcnnscacg tggcatacat catc           54

<210> SEQ ID NO 30
<211> LENGTH: 56
<212> TYPE: DNA
<213> ORGANISM: Artificial
<220> FEATURE:
<223> OTHER INFORMATION: Oligonucleotide Primer AN-14

<400> SEQUENCE: 30
gtattttccc ggctcatcag ttttctccag gacggccttc acctcctggg accggc           56

<210> SEQ ID NO 31
<211> LENGTH: 56
<212> TYPE: DNA
<213> ORGANISM: Artificial
<220> FEATURE:
<223> OTHER INFORMATION: Oligonucleotide Primer AN-21
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature

```
<222> LOCATION: (36)..(37)
<223> OTHER INFORMATION: n is a, c, g, or t

<400> SEQUENCE: 31
cgagccacac ccctgggacc ggsnncccsn nsnnsnngcc ctcagagtaa aagatg      56

<210> SEQ ID NO 32
<211> LENGTH: 24
<212> TYPE: DNA
<213> ORGANISM: Artificial
<220> FEATURE:
<223> OTHER INFORMATION: Oligonucleotide Primer AN-22F

<400> SEQUENCE: 32
tgcccacgag ccacacccct ggga                                         24

<210> SEQ ID NO 33
<211> LENGTH: 33
<212> TYPE: DNA
<213> ORGANISM: Artificial
<220> FEATURE:
<223> OTHER INFORMATION: Oligonucleotide Primer AN-ksf2

<400> SEQUENCE: 33
gtgaacctct tggaattctt cgggtccacc gtc                               33

<210> SEQ ID NO 34
<211> LENGTH: 25
<212> TYPE: DNA
<213> ORGANISM: Artificial
<220> FEATURE:
<223> OTHER INFORMATION: Oligonucleotide Primer AN-ksf1

<400> SEQUENCE: 34
gaccggcccc cggacaacat ggtga                                        25

<210> SEQ ID NO 35
<211> LENGTH: 20
<212> TYPE: DNA
<213> ORGANISM: Artificial
<220> FEATURE:
<223> OTHER INFORMATION: Oligonucleotide Primer F83

<400> SEQUENCE: 35
agacagctat cgcgattgca                                              20

<210> SEQ ID NO 36
<211> LENGTH: 60
<212> TYPE: DNA
<213> ORGANISM: Artificial
<220> FEATURE:
<223> OTHER INFORMATION: Oligonucleotide Primer AN-LW2R
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
```

<222> LOCATION: (41)..(42)
<223> OTHER INFORMATION: n is a, c, g, or t

<400> SEQUENCE: 36
cttctccagg acggccttsn nctcsnngga snngccsnns nncagcatgg tgaccttggc    60

<210> SEQ ID NO 37
<211> LENGTH: 61
<212> TYPE: DNA
<213> ORGANISM: Artificial
<220> FEATURE:
<223> OTHER INFORMATION: Oligonucleotide Primer AN-LW4R
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t

<400> SEQUENCE: 37
cgagccacac ccctgggacc ggcttsnnsn nsnnsnngcc snnagagtaa aagatgtagt    60
g                                                                   61

<210> SEQ ID NO 38
<211> LENGTH: 477
<212> TYPE: DNA
<213> ORGANISM: Artificial
<220> FEATURE:
<223> OTHER INFORMATION: Human tear lipocalin mutein M23*.5 CDS

<400> SEQUENCE: 38
caccacctcc tggcctcaga cgaggagatt caggatgtgt cagggacgtg gtatctgaag    60
gccatgacgg tggacaacag caagaagtac aacaggcgcc actcggtgac agccatgacc   120
ctcacgaccc tggaaggggg caacctggaa gccaaggtca ccatgctgca caagggcaag   180
tccagggagc ataaggccgt cctggagaag actgacgagc cgggaaaata cacggccctc   240
gggggcgacc acgtggcata catcatcagg tcgcacgtga aggaccacta catcttttac   300
tctaagggct ggttgggggg gttcccggtc ccaggggtgt ggctcgtggg cagagacccc   360
aagaacaacc tggaagcctt ggaggacttt gagaaagccg caggagcccg cggactcagc   420
acggagagca tcctcatccc caggcagagc gaaacctgct ctccagggag cgattag      477

<210> SEQ ID NO 39
<211> LENGTH: 158
<212> TYPE: PRT
<213> ORGANISM: Artificial
<220> FEATURE:
<223> OTHER INFORMATION: Human tear lipocalin mutein M23*.5

<400> SEQUENCE: 39

His His Leu Leu Ala Ser Asp Glu Glu Ile Gln Asp Val Ser Gly Thr
1               5                   10                  15

```
Trp Tyr Leu Lys Ala Met Thr Val Asp Asn Ser Lys Lys Tyr Asn Arg
            20                  25                  30

Arg His Ser Val Thr Ala Met Thr Leu Thr Thr Leu Glu Gly Gly Asn
        35                  40                  45

Leu Glu Ala Lys Val Thr Met Leu His Lys Gly Lys Ser Arg Glu His
50                  55                  60

Lys Ala Val Leu Glu Lys Thr Asp Glu Pro Gly Lys Tyr Thr Ala Leu
65                  70                  75                  80

Gly Gly Asp His Val Ala Tyr Ile Ile Arg Ser His Val Lys Asp His
                85                  90                  95

Tyr Ile Phe Tyr Ser Lys Gly Trp Leu Gly Gly Phe Pro Val Pro Gly
            100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
130                 135                 140

Leu Ile Pro Arg Gln Ser Glu Thr Cys Ser Pro Gly Ser Asp
145                 150                 155

<210> SEQ ID NO 40
<211> LENGTH: 477
<212> TYPE: DNA
<213> ORGANISM: Artificial
<220> FEATURE:
<223> OTHER INFORMATION: Human tear lipocalin mutein M23*.14 CDS

<400> SEQUENCE: 40
caccacctcc tggcctcaga cgaggagatt caggatgtgt cagggacgtg gtatctgaag      60
gccatgacgg tggacaacag caagaagtac aacaggcgcc actcggtgac agccatgacc     120
ctcacgaccc tggaaggggg caacctggaa gccaaggtca ccatgctgca caagggcaag     180
tccaaggagt acaaggccgt cctggagaag actgacgagc cgggaaaata cacggccctc     240
gggggcgacc acgtggcata catcatcagg tcgcacgtga aggaccacta catcttttac     300
tctaagggct ggttgggggg gttcccggtc ccaggggtgt ggctcgtggg cagagacccc     360
aagaacaacc tggaagcctt ggaggacttt gagaaagccg caggagcccg cggactcagc     420
acggagagca tcctcatccc caggcagagc gaaacctgct ctccagggag cgattag        477

<210> SEQ ID NO 41
<211> LENGTH: 158
<212> TYPE: PRT
<213> ORGANISM: Artificial
<220> FEATURE:
<223> OTHER INFORMATION: Human tear lipocalin mutein M23*.14

<400> SEQUENCE: 41

His His Leu Leu Ala Ser Asp Glu Glu Ile Gln Asp Val Ser Gly Thr
1               5                   10                  15

Trp Tyr Leu Lys Ala Met Thr Val Asp Asn Ser Lys Lys Tyr Asn Arg
            20                  25                  30

Arg His Ser Val Thr Ala Met Thr Leu Thr Thr Leu Glu Gly Gly Asn
        35                  40                  45

Leu Glu Ala Lys Val Thr Met Leu His Lys Gly Lys Ser Lys Glu Tyr
50                  55                  60

Lys Ala Val Leu Glu Lys Thr Asp Glu Pro Gly Lys Tyr Thr Ala Leu
65                  70                  75                  80

Gly Gly Asp His Val Ala Tyr Ile Ile Arg Ser His Val Lys Asp His
                85                  90                  95
```

Tyr Ile Phe Tyr Ser Lys Gly Trp Leu Gly Gly Phe Pro Val Pro Gly
                100                 105                 110

Val Trp Leu Val Gly Arg Asp Pro Lys Asn Asn Leu Glu Ala Leu Glu
            115                 120                 125

Asp Phe Glu Lys Ala Ala Gly Ala Arg Gly Leu Ser Thr Glu Ser Ile
        130                 135                 140

Leu Ile Pro Arg Gln Ser Glu Thr Cys Ser Pro Gly Ser Asp
145                 150                 155

<210> SEQ ID NO 42
<211> LENGTH: 477
<212> TYPE: DNA
<213> ORGANISM: Artificial
<220> FEATURE:
<223> OTHER INFORMATION: Human tear lipocalin mutein M23*.28 CDS

<400> SEQUENCE: 42
caccacctcc tggcctcaga cgaggagatt caggatgtgt cagggacgtg gtatctgaag      60
gccatgacgg tggacaacag caagaagtac aacaggcgcc actcggtgac agccatgacc     120
ctcacgaccc tggaagggg caacctggaa gccaaggtca ccatgctgca ccgcggccac      180
tcccacgagc acaaggccgt cctggagaag actgacgagc cgggaaaata cacggccctc     240
gggggcgacc acgtggcata catcatcagg tcgcacgtga aggaccactg catcttttac     300
tctaagggct ggttgggggg gttcccggtc caggggtgt ggctcgtggg cagagacccc      360
aagaacaacc tggaagcctt ggaggacttt gagaaagccg caggagcccg cggactcagc     420
acggagagca tcctcatccc caggcagagc gaaacctgct ctccagggag cgattag        477

<210> SEQ ID NO 43
<211> LENGTH: 158
<212> TYPE: PRT
<213> ORGANISM: Artificial
<220> FEATURE:
<223> OTHER INFORMATION: Human tear lipocalin mutein M23*.28

<400> SEQUENCE: 43

His His Leu Leu Ala Ser Asp Glu Glu Ile Gln Asp Val Ser Gly Thr
1               5                   10                  15

Trp Tyr Leu Lys Ala Met Thr Val Asp Asn Ser Lys Lys Tyr Asn Arg
            20                  25                  30

Arg His Ser Val Thr Ala Met Thr Leu Thr Thr Leu Glu Gly Gly Asn
        35                  40                  45

Leu Glu Ala Lys Val Thr Met Leu His Arg Gly His Ser His Glu His
    50                  55                  60

Lys Ala Val Leu Glu Lys Thr Asp Glu Pro Gly Lys Tyr Thr Ala Leu
65                  70                  75                  80

Gly Gly Asp His Val Ala Tyr Ile Ile Arg Ser His Val Lys Asp His
                85                  90                  95

Cys Ile Phe Tyr Ser Lys Gly Trp Leu Gly Gly Phe Pro Val Pro Gly
                100                 105                 110

Val Trp Leu Val Gly Arg Asp Pro Lys Asn Asn Leu Glu Ala Leu Glu
            115                 120                 125

Asp Phe Glu Lys Ala Ala Gly Ala Arg Gly Leu Ser Thr Glu Ser Ile
        130                 135                 140

Leu Ile Pro Arg Gln Ser Glu Thr Cys Ser Pro Gly Ser Asp
145                 150                 155

<210> SEQ ID NO 44
<211> LENGTH: 477
<212> TYPE: DNA
<213> ORGANISM: Artificial
<220> FEATURE:
<223> OTHER INFORMATION: Human tear lipocalin mutein M23*.30 CDS

<400> SEQUENCE: 44

```
caccacctcc tggcctcaga cgaggagatt caggatgtgt cagggacgtg gtatctgaag      60
gccatgacgg tggacaacag caagaagtac aacaggcgcc actcggtgac agccatgacc     120
ctcacgaccc tggaagggggg caacctggaa gccaaggtca ccatgctgat caagggccgg    180
tccaaggagc ataaggccgt cctggagaag actgacgagc cgggaaaata cacggccctc    240
gggggcgacc acgtggcata catcatcagg tcgcacgtga aggaccacta catcttttac    300
tctaagggct ggttgggggg gttcccggtc caggggtgt ggctcgtggg cagagacccc    360
aagaacaacc tggaagcctt ggaggacttt gagaaagccg caggagcccg cggactcagc    420
acggagagca tcctcatccc caggcagagc gaaacctgct ctccagggag cgattag      477
```

<210> SEQ ID NO 45
<211> LENGTH: 158
<212> TYPE: PRT
<213> ORGANISM: Artificial
<220> FEATURE:
<223> OTHER INFORMATION: Human tear lipocalin mutein M23*.30

<400> SEQUENCE: 45

```
His His Leu Leu Ala Ser Asp Glu Glu Ile Gln Asp Val Ser Gly Thr
1               5                   10                  15

Trp Tyr Leu Lys Ala Met Thr Val Asp Asn Ser Lys Lys Tyr Asn Arg
            20                  25                  30

Arg His Ser Val Thr Ala Met Thr Leu Thr Thr Leu Glu Gly Gly Asn
        35                  40                  45

Leu Glu Ala Lys Val Thr Met Leu Ile Lys Gly Arg Ser Lys Glu His
    50                  55                  60

Lys Ala Val Leu Glu Lys Thr Asp Glu Pro Gly Lys Tyr Thr Ala Leu
65                  70                  75                  80

Gly Gly Asp His Val Ala Tyr Ile Ile Arg Ser His Val Lys Asp His
                85                  90                  95

Tyr Ile Phe Tyr Ser Lys Gly Trp Leu Gly Gly Phe Pro Val Pro Gly
            100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly Ser Asp
145                 150                 155
```

<210> SEQ ID NO 46
<211> LENGTH: 477
<212> TYPE: DNA
<213> ORGANISM: Artificial
<220> FEATURE:
<223> OTHER INFORMATION: Human tear lipocalin mutein M23*.34 CDS

<400> SEQUENCE: 46

```
caccacctcc tggcctcaga cgaggagatt caggatgtgt cagggacgtg gtatctgaag      60
gccatgacgg tggacaacag caagaagtac aacaggcgcc actcggtgac agccatgacc     120
ctcacgaccc tggaagggggg caacctggaa gccaaggtca ccatgctgac caagggcaag    180
```

```
tccaaggagt ggaaggccgt cctggagaag actgacgagc cgggaaaata cacggccctc    240
gggggcgacc acgtggcata catcatcagg tcgcacgtga aggaccacta catcttttac    300
tctaagggct ggttgggggg gttcccggtc ccagggtgt ggctcgtggg cagagacccc    360
aagaacaacc tggaagcctt ggaggacttt gagaaagccg caggagcccg cggactcagc    420
acggagagca tcctcatccc caggcagagc gaaacctgct ctccagggag cgattag      477
```

<210> SEQ ID NO 47
<211> LENGTH: 158
<212> TYPE: PRT
<213> ORGANISM: Artificial
<220> FEATURE:
<223> OTHER INFORMATION: Human tear lipocalin mutein M23*.34

<400> SEQUENCE: 47

```
His His Leu Leu Ala Ser Asp Glu Glu Ile Gln Asp Val Ser Gly Thr
1               5                   10                  15

Trp Tyr Leu Lys Ala Met Thr Val Asp Asn Ser Lys Lys Tyr Asn Arg
            20                  25                  30

Arg His Ser Val Thr Ala Met Thr Leu Thr Thr Leu Glu Gly Gly Asn
        35                  40                  45

Leu Glu Ala Lys Val Thr Met Leu Thr Lys Gly Lys Ser Lys Glu Trp
    50                  55                  60

Lys Ala Val Leu Glu Lys Thr Asp Glu Pro Gly Lys Tyr Thr Ala Leu
65                  70                  75                  80

Gly Gly Asp His Val Ala Tyr Ile Ile Arg Ser His Val Lys Asp His
                85                  90                  95

Tyr Ile Phe Tyr Ser Lys Gly Trp Leu Gly Gly Phe Pro Val Pro Gly
            100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly Ser Asp
145                 150                 155
```

<210> SEQ ID NO 48
<211> LENGTH: 477
<212> TYPE: DNA
<213> ORGANISM: Artificial
<220> FEATURE:
<223> OTHER INFORMATION: Human tear lipocalin mutein M23*.36 CDS

<400> SEQUENCE: 48

```
caccacctcc tggcctcaga cgaggagatt caggatgtgt cagggacgtg gtatctgaag    60
gccatgacgg tggacaacag caagaagtac aacaggcgcc actcggtgac agccatgacc   120
ctcacgaccc tggaaggggg caacctggaa gccaaggtca ccatgctggt gcacggcaag   180
tcccgcgagt acaaggccgt cctggagaag actgacgagc cgggaaaata cacggccctc   240
gggggcgacc acgtggcata catcatcagg tcgcacgtga aggaccacta catcttttac   300
tctaagggct ggttgggggg gttcccggtc ccagggtgt ggctcgtggg cagagacccc   360
aagaacaacc tggaagcctt ggaggacttt gagaaagccg caggagcccg cggactcagc   420
acggagagca tcctcatccc caggcagagc gaaacctgct ctccagggag cgattag     477
```

<210> SEQ ID NO 49
<211> LENGTH: 158

```
<212> TYPE: PRT
<213> ORGANISM: Artificial
<220> FEATURE:
<223> OTHER INFORMATION: Human tear lipocalin mutein M23*.36

<400> SEQUENCE: 49

His His Leu Leu Ala Ser Asp Glu Glu Ile Gln Asp Val Ser Gly Thr
1               5                   10                  15

Trp Tyr Leu Lys Ala Met Thr Val Asp Asn Ser Lys Lys Tyr Asn Arg
            20                  25                  30

Arg His Ser Val Thr Ala Met Thr Leu Thr Thr Leu Glu Gly Gly Asn
        35                  40                  45

Leu Glu Ala Lys Val Thr Met Leu Val His Gly Lys Ser Arg Glu Tyr
    50                  55                  60

Lys Ala Val Leu Glu Lys Thr Asp Glu Pro Gly Lys Tyr Thr Ala Leu
65                  70                  75                  80

Gly Gly Asp His Val Ala Tyr Ile Ile Arg Ser His Val Lys Asp His
                85                  90                  95

Tyr Ile Phe Tyr Ser Lys Gly Trp Leu Gly Gly Phe Pro Val Pro Gly
            100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
130                 135                 140

Leu Ile Pro Arg Gln Ser Glu Thr Cys Ser Pro Gly Ser Asp
145                 150                 155

<210> SEQ ID NO 50
<211> LENGTH: 477
<212> TYPE: DNA
<213> ORGANISM: Artificial
<220> FEATURE:
<223> OTHER INFORMATION: Human tear lipocalin mutein M23*.39 CDS

<400> SEQUENCE: 50
caccacctcc tggcctcaga cgaggagatt caggatgtgt cagggacgtg gtatctgaag      60
gccatgacgg tggacaacag caagaagtac aacaggcgcc actcggtgac agccatgacc     120
ctcacgaccc tggaagggggg caacctggaa gccaaggtca ccatgctgaa gcacggcaag    180
tccaaggaga ctaaggccgt cctggagaag actgacgagc cgggaaaata cacggtcctc    240 ggggggcgacc acgtggcata catcatcagg tcgcacgtga aggaccacta catctttttac   300 tctaagggct ggttgggggg gttcccggtc ccaggggtgt ggctcgtggg cagagacccc    360
aagaacaacc tggaagcctt ggaggacttt gagaaagccg caggagcccg cggactcagc    420
acggagagca tcctcatccc caggcagagc gaaacctgct ctccagggag cgattag        477

<210> SEQ ID NO 51
<211> LENGTH: 158
<212> TYPE: PRT
<213> ORGANISM: Artificial
<220> FEATURE:
<223> OTHER INFORMATION: Human tear lipocalin mutein M23*.39

<400> SEQUENCE: 51

His His Leu Leu Ala Ser Asp Glu Glu Ile Gln Asp Val Ser Gly Thr
1               5                   10                  15

Trp Tyr Leu Lys Ala Met Thr Val Asp Asn Ser Lys Lys Tyr Asn Arg
            20                  25                  30

Arg His Ser Val Thr Ala Met Thr Leu Thr Thr Leu Glu Gly Gly Asn
```

```
                    35                    40                    45

Leu Glu Ala Lys Val Thr Met Leu Lys His Gly Lys Ser Lys Glu Thr
 50                  55                  60

Lys Ala Val Leu Glu Lys Thr Asp Glu Pro Gly Lys Tyr Thr Val Leu
 65                  70                  75                  80

Gly Gly Asp His Val Ala Tyr Ile Ile Arg Ser His Val Lys Asp His
                 85                  90                  95

Tyr Ile Phe Tyr Ser Lys Gly Trp Leu Gly Phe Pro Val Pro Gly
                100                 105                 110

Val Trp Leu Val Gly Arg Asp Pro Lys Asn Asn Leu Glu Ala Leu Glu
            115                 120                 125

Asp Phe Glu Lys Ala Ala Gly Ala Arg Gly Leu Ser Thr Glu Ser Ile
130                 135                 140

Leu Ile Pro Arg Gln Ser Glu Thr Cys Ser Pro Gly Ser Asp
145                 150                 155

<210> SEQ ID NO 52
<211> LENGTH: 477
<212> TYPE: DNA
<213> ORGANISM: Artificial
<220> FEATURE:
<223> OTHER INFORMATION: Human tear lipocalin mutein M23*40 CDS

<400> SEQUENCE: 52
caccacctcc tggcctcaga cgaggagatt caggatgtgt cagggacgtg gtatctgaag      60
gccatgacgg tggacaacag caagaagtac aacaggcgcc actcggtgac agccatgacc     120
ctcacgaccc tggaaggggg caacctggaa gccaaggtca ccatgctgaa gaagggcaag     180
tccatcgagc ataaggccgt cctggagaag actgacgagc cgggaaaata cacggccctc     240
gggggcgacc acgtggcata catcatcagg tcgcacgtga aggaccacta tatctttac      300 tctaagggct ggttgggggg gttcccggtc ccagggtgt ggctcgtggg cagagacccc      360
aagaacaacc tggaagcctt ggaggacttt gagaaagccg caggagcccg cggactcagc     420
acggagagca tcctcatccc caggcagagc gaaacctgct ctccagggag cgattag        477

<210> SEQ ID NO 53
<211> LENGTH: 158
<212> TYPE: PRT
<213> ORGANISM: Artificial
<220> FEATURE:
<223> OTHER INFORMATION: Human tear lipocalin mutein M23*.40

<400> SEQUENCE: 53

His His Leu Leu Ala Ser Asp Glu Glu Ile Gln Asp Val Ser Gly Thr
  1               5                  10                  15

Trp Tyr Leu Lys Ala Met Thr Val Asp Asn Ser Lys Lys Tyr Asn Arg
                 20                  25                  30

Arg His Ser Val Thr Ala Met Thr Leu Thr Thr Leu Glu Gly Gly Asn
             35                  40                  45

Leu Glu Ala Lys Val Thr Met Leu Lys Lys Gly Lys Ser Ile Glu His
 50                  55                  60

Lys Ala Val Leu Glu Lys Thr Asp Glu Pro Gly Lys Tyr Thr Ala Leu
 65                  70                  75                  80

Gly Gly Asp His Val Ala Tyr Ile Ile Arg Ser His Val Lys Asp His
                 85                  90                  95

Tyr Ile Phe Tyr Ser Lys Gly Trp Leu Gly Phe Pro Val Pro Gly
                100                 105                 110
```

-continued

```
Val Trp Leu Val Gly Arg Asp Pro Lys Asn Asn Leu Glu Ala Leu Glu
            115                 120                 125
Asp Phe Glu Lys Ala Ala Gly Ala Arg Gly Leu Ser Thr Glu Ser Ile
        130                 135                 140
Leu Ile Pro Arg Gln Ser Glu Thr Cys Ser Pro Gly Ser Asp
145                 150                 155
```

<210> SEQ ID NO 54
<211> LENGTH: 477
<212> TYPE: DNA
<213> ORGANISM: Artificial
<220> FEATURE:
<223> OTHER INFORMATION: Human tear lipocalin mutein M23*.41 CDS

<400> SEQUENCE: 54

```
caccacctcc tggcctcaga cgaggagatt caggatgtgt cagggacgtg gtatctgaag      60
gccatgacgg tggacaacag caagaagtac aacaggcgcc actcggtgac agccatgacc     120
ctcacgaccc tggaaggggg caacctggaa gccaaggtca ccatactgcg caagggccgg     180
tccgaggagt ggaaggccgt cctggagaag actgacgagc cgggaaaata cacggccctc     240
ggggcgacc acgtggcata catcatcagg tcgcacgtga aggaccacta catcttttac     300
tctaagggct ggttgggggg gttcccggtc caggggtgt ggctcgtggg cagagacccc     360
aagaacaacc tggaagcctt ggaggacttt gagaaagccg caggagcccg cggactcagc     420
acggagagca tcctcatccc caggcagagc gaaacctgct ctccagggag cgattag        477
```

<210> SEQ ID NO 55
<211> LENGTH: 158
<212> TYPE: PRT
<213> ORGANISM: Artificial
<220> FEATURE:
<223> OTHER INFORMATION: Human tear lipocalin mutein M23*.41

<400> SEQUENCE: 55

```
His His Leu Leu Ala Ser Asp Glu Glu Ile Gln Asp Val Ser Gly Thr
1               5                   10                  15
Trp Tyr Leu Lys Ala Met Thr Val Asp Asn Ser Lys Lys Tyr Asn Arg
            20                  25                  30
Arg His Ser Val Thr Ala Met Thr Leu Thr Thr Leu Glu Gly Gly Asn
        35                  40                  45
Leu Glu Ala Lys Val Thr Ile Leu Arg Lys Gly Arg Ser Glu Glu Trp
    50                  55                  60
Lys Ala Val Leu Glu Lys Thr Asp Glu Pro Gly Lys Tyr Thr Ala Leu
65                  70                  75                  80
Gly Gly Asp His Val Ala Tyr Ile Ile Arg Ser His Val Lys Asp His
                85                  90                  95
Tyr Ile Phe Tyr Ser Lys Gly Trp Leu Gly Gly Phe Pro Val Pro Gly
            100                 105                 110
Val Trp Leu Val Gly Arg Asp Pro Lys Asn Asn Leu Glu Ala Leu Glu
        115                 120                 125
Asp Phe Glu Lys Ala Ala Gly Ala Arg Gly Leu Ser Thr Glu Ser Ile
    130                 135                 140
Leu Ile Pro Arg Gln Ser Glu Thr Cys Ser Pro Gly Ser Asp
145                 150                 155
```

<210> SEQ ID NO 56
<211> LENGTH: 477
<212> TYPE: DNA
<213> ORGANISM: Artificial

<220> FEATURE:
<223> OTHER INFORMATION: Human tear lipocalin mutein M23*.45 CDS

<400> SEQUENCE: 56

```
caccacctcc tggcctcaga cgaggagatt caggatgtgt cagggacgtg gtatctgaag    60
gccatgacgg tggacaacag caagaagtac aacaggcgcc actcggtgac agccatgacc   120
ctcacgaccc tggaaggggg caacctggaa gccaaggtca ccatgctgcg caagggcaag   180
tccacggagc acaaggccgt cctggagaag actgacgagc cgggaaaata cacggtcctc   240
ggggcgacc acgtggcgta catcatcagg tcgcacgtga aggaccacta catcttttac    300
tctaagggct ggttgggggg gttcccggtc ccaggggtgt ggctcgtggg cagagacccc   360
aagaacaacc tggaagcctt ggaggacttt gagaaagccg caggagcccg cggactcagc   420
acggagagca tcctcatccc caggcagagc gaaacctgct ctccagggag cgattag      477
```

<210> SEQ ID NO 57
<211> LENGTH: 158
<212> TYPE: PRT
<213> ORGANISM: Artificial
<220> FEATURE:
<223> OTHER INFORMATION: Human tear lipocalin mutein M23*.45

<400> SEQUENCE: 57

```
His His Leu Leu Ala Ser Asp Glu Glu Ile Gln Asp Val Ser Gly Thr
  1               5                  10                  15

Trp Tyr Leu Lys Ala Met Thr Val Asp Asn Ser Lys Lys Tyr Asn Arg
             20                  25                  30

Arg His Ser Val Thr Ala Met Thr Leu Thr Thr Leu Glu Gly Gly Asn
         35                  40                  45

Leu Glu Ala Lys Val Thr Met Leu Arg Lys Gly Lys Ser Thr Glu His
     50                  55                  60

Lys Ala Val Leu Glu Lys Thr Asp Glu Pro Gly Lys Tyr Thr Val Leu
 65                  70                  75                  80

Gly Gly Asp His Val Ala Tyr Ile Ile Arg Ser His Val Lys Asp His
                 85                  90                  95

Tyr Ile Phe Tyr Ser Lys Gly Trp Leu Gly Gly Phe Pro Val Pro Gly
            100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly Ser Asp
145                 150                 155
```

<210> SEQ ID NO 58
<211> LENGTH: 477
<212> TYPE: DNA
<213> ORGANISM: Artificial
<220> FEATURE:
<223> OTHER INFORMATION: Human tear lipocalin mutein M23*.49 CDS

<400> SEQUENCE: 58

```
caccacctcc tggcctcaga cgaggagatt caggatgtgt cagggacgtg gtatctgaag    60
gccatgacgg tggacaacag caagaagtac aacaggcgcc actcggtgac agccatgacc   120
ctcacgaccc tggaaggggg caacctggaa gccaaggtca ccatgctgtg aagggcaag    180
tccgtggagc gtaaggccgt cctggagaag actgacgagc cgggaaaata cacggccctc   240
ggggcgacc acgtggcata catcatcagg tcgcacgtga aggaccacta catcttttac    300
```

```
tctaagggct ggttgggggg gttcccggtc ccaggggtgt ggctcgtggg cagagacccc    360
aagaacaacc tggaagcctt ggaggacttt gagaaagccg caggagcccg cggactcagc    420
acggagagca tcctcatccc caggcagagc gaaacctgct ctccagggag cgattag      477
```

```
<210> SEQ ID NO 59
<211> LENGTH: 158
<212> TYPE: PRT
<213> ORGANISM: Artificial
<220> FEATURE:
<223> OTHER INFORMATION: Human tear lipocalin mutein M23*.49

<400> SEQUENCE: 59
```

His His Leu Leu Ala Ser Asp Glu Glu Ile Gln Asp Val Ser Gly Thr
1               5                   10                  15

Trp Tyr Leu Lys Ala Met Thr Val Asp Asn Ser Lys Lys Tyr Asn Arg
            20                  25                  30

Arg His Ser Val Thr Ala Met Thr Leu Thr Leu Glu Gly Gly Asn
        35                  40                  45

Leu Glu Ala Lys Val Thr Met Leu Trp Lys Gly Lys Ser Val Glu Arg
    50                  55                  60

Lys Ala Val Leu Glu Lys Thr Asp Glu Pro Gly Lys Tyr Thr Ala Leu
65                  70                  75                  80

Gly Gly Asp His Val Ala Tyr Ile Ile Arg Ser His Val Lys Asp His
                85                  90                  95

Tyr Ile Phe Tyr Ser Lys Gly Trp Leu Gly Gly Phe Pro Val Pro Gly
            100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly Ser Asp
145                 150                 155

```
<210> SEQ ID NO 60
<211> LENGTH: 477
<212> TYPE: DNA
<213> ORGANISM: Artificial
<220> FEATURE:
<223> OTHER INFORMATION: Human tear lipocalin mutein M23*.50 CDS

<400> SEQUENCE: 60
caccacctcc tggcctcaga cgaggagatt caggatgtgt cagggacgtg gtatctgaag    60
gccatgacgg tggacaacag caagaagtac aacaggcgcc actcggtgac agccatgacc   120
ctcacgaccc tggaaggggg caacctggaa gccaaggtca ccatgctgga gcgcggcaag   180
tcccgggagt acaaggccgt cctggagaag actgacgagc cgggaaaata cacggccctc   240 ggggcgacc acgtggcata catcatcagg tcgcacgtga aggaccacta catcttttac   300
tctaagggct ggttgggggg gttcccggtc ccaggggtgt ggctcgtggg cagagacccc   360
aagaacaacc tggaagcctt ggaggacttt gagaaagccg caggagcccg cggactcagc   420
acggagagca tcctcatccc caggcagagc gaaacctgct ctccagggag cgattag      477
```

```
<210> SEQ ID NO 61
<211> LENGTH: 158
<212> TYPE: PRT
<213> ORGANISM: Artificial
<220> FEATURE:
<223> OTHER INFORMATION: Human tear lipocalin mutein M23*.50
```

<400> SEQUENCE: 61

His His Leu Leu Ala Ser Asp Glu Glu Ile Gln Asp Val Ser Gly Thr
1               5                   10                  15

Trp Tyr Leu Lys Ala Met Thr Val Asp Asn Ser Lys Lys Tyr Asn Arg
            20                  25                  30

Arg His Ser Val Thr Ala Met Thr Leu Thr Thr Leu Glu Gly Gly Asn
        35                  40                  45

Leu Glu Ala Lys Val Thr Met Leu Glu Arg Gly Lys Ser Arg Glu Tyr
    50                  55                  60

Lys Ala Val Leu Glu Lys Thr Asp Glu Pro Gly Lys Tyr Thr Ala Leu
65                  70                  75                  80

Gly Gly Asp His Val Ala Tyr Ile Ile Arg Ser His Val Lys Asp His
                85                  90                  95

Tyr Ile Phe Tyr Ser Lys Gly Trp Leu Gly Gly Phe Pro Val Pro Gly
            100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
130                 135                 140

Leu Ile Pro Arg Gln Ser Glu Thr Cys Ser Pro Gly Ser Asp
145                 150                 155

<210> SEQ ID NO 62
<211> LENGTH: 477
<212> TYPE: DNA
<213> ORGANISM: Artificial
<220> FEATURE:
<223> OTHER INFORMATION: Human tear lipocalin mutein M23*.52 CDS

<400> SEQUENCE: 62

```
caccacctcc tggcctcaga cgaggagatt caggatgtgt cagggacgtg gtatctgaag    60
gccatgacgg tggacaacag caagaagtac aacaggcgcc actcggtgac agccatgacc   120
ctcacgaccc tggaaggggg caacctggaa gccaaggtca ccatgctgca aagggcagg    180
tccaaggagc acaaggccgt cctggagaag actgacgagc cgggaaaata cacggccctc   240
gggggcgacc acgtggcata tcatcagg tcgcacgtga aggaccacta catcttttac   300
tctaagggct ggttgggggg gttcccggtc ccaggggtgt ggctcgtggg cagagacccc   360
aagaacaacc tggaagcctt ggaggacttt gagaaagccg caggagcccg cggactcagc   420
acggagagca tcctcatccc caggcagagc gaaacctgct ctccagggag cgattag      477
```

<210> SEQ ID NO 63
<211> LENGTH: 158
<212> TYPE: PRT
<213> ORGANISM: Artificial
<220> FEATURE:
<223> OTHER INFORMATION: Human tear lipocalin mutein M23*.52

<400> SEQUENCE: 63

His His Leu Leu Ala Ser Asp Glu Glu Ile Gln Asp Val Ser Gly Thr
1               5                   10                  15

Trp Tyr Leu Lys Ala Met Thr Val Asp Asn Ser Lys Lys Tyr Asn Arg
            20                  25                  30

Arg His Ser Val Thr Ala Met Thr Leu Thr Thr Leu Glu Gly Gly Asn
        35                  40                  45

Leu Glu Ala Lys Val Thr Met Leu His Lys Gly Arg Ser Lys Glu His
    50                  55                  60

Lys Ala Val Leu Glu Lys Thr Asp Glu Pro Gly Lys Tyr Thr Ala Leu
65                  70                  75                  80

Gly Gly Asp His Val Ala Tyr Ile Ile Arg Ser His Val Lys Asp His
                85                  90                  95

Tyr Ile Phe Tyr Ser Lys Gly Trp Leu Gly Gly Phe Pro Val Pro Gly
            100                 105                 110

Val Trp Leu Val Gly Arg Asp Pro Lys Asn Asn Leu Glu Ala Leu Glu
        115                 120                 125

Asp Phe Glu Lys Ala Ala Gly Ala Arg Gly Leu Ser Thr Glu Ser Ile
    130                 135                 140

Leu Ile Pro Arg Gln Ser Glu Thr Cys Ser Pro Gly Ser Asp
145                 150                 155

<210> SEQ ID NO 64
<211> LENGTH: 603
<212> TYPE: DNA
<213> ORGANISM: Artificial
<220> FEATURE:
<223> OTHER INFORMATION: recombinant human tear lipocalin gene,
      positions 118-720

<400> SEQUENCE: 64
tctagataac gagggcaaaa aatgaaaaag acagctatcg cgattgcagt ggcactggct      60
ggtttcgcta ccgtagcgca ggccgcctca gacgaggaga ttcaggatgt gtcagggacg     120
tggtatctga aggccatgac ggtggacagg gagttccctg agatgaatct ggaatcggtg     180
acacccatga ccctcacgac cctggaaggg gcaacctgg aagccaaggt caccatgctg      240
ataagtggcc ggagccagga ggtgaaggcc gtcctggaga aaactgacga gccgggaaaa     300
tacacggccg acggggggcaa gcacgtggca tacatcatca ggtcgcacgt gaaggaccac    360
tacatctttt actctgaggg cgagctccac gggaagccgg tcccagggt gtggctcgtg     420 ggcagagacc ccaagaacaa cctggaagcc ttggaggact tgagaaagc cgcaggagcc     480 cgcggactca gcacggagag catcctcatc cccaggcaga gcgaaaccag ctctccaggg    540
agcgcttggt ctcacccgca gttcgaaaaa taataagctt gacctgtgaa gtgaaaatg     600 gcg                                                                  603

<210> SEQ ID NO 65
<211> LENGTH: 183
<212> TYPE: PRT
<213> ORGANISM: Artificial
<220> FEATURE:
<223> OTHER INFORMATION: recombinant human tear lipocalin with signal
      sequence

<400> SEQUENCE: 65

Met Lys Lys Thr Ala Ile Ala Ile Ala Val Ala Leu Ala Gly Phe Ala
1               5                   10                  15

Thr Val Ala Gln Ala Ala Ser Asp Glu Glu Ile Gln Asp Val Ser Gly
            20                  25                  30

Thr Trp Tyr Leu Lys Ala Met Thr Val Asp Arg Glu Phe Pro Glu Met
        35                  40                  45

Asn Leu Glu Ser Val Thr Pro Met Thr Leu Thr Thr Leu Glu Gly Gly
    50                  55                  60

Asn Leu Glu Ala Lys Val Thr Met Leu Ile Ser Gly Arg Ser Gln Glu
65                  70                  75                  80

Val Lys Ala Val Leu Glu Lys Thr Asp Glu Pro Gly Lys Tyr Thr Ala
                85                  90                  95

```
Asp Gly Gly Lys His Val Ala Tyr Ile Ile Arg Ser His Val Lys Asp
            100                 105                 110

His Tyr Ile Phe Tyr Ser Glu Gly Glu Leu His Gly Lys Pro Val Pro
        115                 120                 125

Gly Val Trp Leu Val Gly Arg Asp Pro Thr Asn Asn Leu Glu Ala Leu
        130                 135                 140

Glu Asp Phe Glu Lys Ala Ala Gly Ala Arg Gly Leu Ser Thr Glu Ser
145                 150                 155                 160

Ile Leu Ile Pro Arg Gln Ser Glu Thr Ser Ser Pro Gly Ser Ala Trp
                165                 170                 175

Ser His Pro Gln Phe Glu Lys
            180
```